US006462036B1

(12) United States Patent
Doyle et al.

(10) Patent No.: US 6,462,036 B1
(45) Date of Patent: Oct. 8, 2002

(54) TRICYCLIC PYRAZOLE DERIVATIVES

(75) Inventors: Kevin J. Doyle; Paul Rafferty; Robert W. Steele; David J. Wilkins, all of Nottingham (GB); Lee D. Arnold, Westborough, MA (US); Michael Hockley, Nottingham (GB); Anna M. Ericsson, Shrewsbury, MA (US); Nobuhiko Iwasaki; Nobuo Ogawa, both of Katsuyama Fukui (JP)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/573,366

(22) Filed: May 17, 2000

Related U.S. Application Data

(63) Continuation-in-part of application No. PCT/US99/26105, filed on Nov. 4, 1999.
(60) Provisional application No. 60/107,467, filed on Nov. 6, 1998.

(51) Int. Cl.$^7$ ...................... A61K 31/55; C07D 243/08; C07D 403/00; C07D 211/68; C07D 231/54
(52) U.S. Cl. ............... 514/218; 514/232.8; 514/252.19; 514/253.09; 514/254.06; 514/316; 514/318; 514/321; 514/322; 514/323; 514/338; 514/393; 540/575; 544/115; 544/295; 544/360; 544/371; 546/187; 546/193; 546/194; 546/199; 546/275.7; 548/359.1; 548/359.5
(58) Field of Search ............................... 514/218, 232.8, 514/252.19, 253.09, 254.06, 316, 318, 321, 322, 323, 338, 393; 540/575; 544/115, 295, 360, 371; 546/187, 193, 194, 199, 275.7; 548/359.1, 359.5

(56) References Cited

U.S. PATENT DOCUMENTS 3,843,664 A * 10/1974 Coombs
3,843,665 A * 10/1974 Coombs
3,843,666 A * 10/1974 Coombs
3,932,430 A * 1/1976 Babeck
3,957,816 A * 5/1976 Habke
3,959,308 A * 5/1976 Coombs
5,686,480 A   11/1997 Collins et al. ............... 514/403

FOREIGN PATENT DOCUMENTS

| JP | 60 130521 | 7/1985 |
| WO | 9410162 | * 5/1994 |
| WO | WO 97/15308 | 5/1997 |
| WO | WO 99/17769 | 4/1999 |
| WO | WO 99/17770 | 4/1999 |
| WO | WO 99/54308 A1 | 10/1999 |
| WO | WO 00/27822 A2 | 5/2000 |
| WO | WO 00/59901 A1 | 10/2000 |

OTHER PUBLICATIONS

CA 90:180034, Lemke, 1978.*
CA 131:58670, Somogyi, 1999.*
CA 126:27896, Povey, 1996.*
CA 102:62009, Gatta, 1984.*
Mosher, W.A., et al., "3–Cycloalkyl—and 3–Heterocyclic Substituted Indeno [1,2–c]pyrazol–4(1H) ones," *J. Heterocyclic Chem.*, 8:855–859 (1971).

* cited by examiner

*Primary Examiner*—D. Margaret Seaman
(74) *Attorney, Agent, or Firm*—John D. Conway

(57) ABSTRACT

This invention relates to certain 3-aryl or 3-heteroaryl pyrazoles with 4,5(3,4)-bicyclic ring fusion which are inhibitors of protein kinase activity, of which some are novel compounds, to pharmaceutical compositions containing these pyrazoles and to processes for preparing these pyrazoles.

55 Claims, No Drawings

TRICYCLIC PYRAZOLE DERIVATIVES

RELATED APPLICATIONS

This application is a Continuation-in-Part of and claims priority to International Application No.: PCT/US99/26105, which designates the United States, filed Nov. 4, 1999 which claims the benefit of U.S. Provisional Application No. 60/107,467, filed Nov. 6, 1998, the entire teachings of which are incorporated herein by reference.

This invention relates to certain 3-aryl or 3-heteroaryl pyrazoles with 4,5(3,4)-bicyclic ring fusion which are inhibitors of protein kinases, particularly tyrosine kinases and serine/threonine kinases, of which some are novel compounds, to pharmaceutical compositions containing these pyrazoles and to processes for preparing these pyrazoles.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383–391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor transphosphorylation. Binding sites are thereby created for intracellular signal transduction molecules and lead to the formation of complexes with a spectrum of cytoplasmic signaling molecules that facilitate the appropriate cellular response (e.g., cell division, differentiation, metabolic effects, changes in the extracellular microenvironment); see Schlessinger and Ullrich, 1992, *Neuron* 9:1–20.

Proteins with SH2 (src homology-2) or phosphotyrosine binding (PTB) domains bind activated tyrosine kinase receptors and their substrates with high affinity to propagate signals into cells. Both of the domains recognize phosphotyrosine (Fantl, et al., 1992, *Cell* 69:413–423; Songyang, et al., 1994, *Mol. Cell. Biol.* 14:2777–2785; Songyang, et al., 1993, *Cell* 72:767–778; and Koch, et al., 1991, *Science* 252:668–678; Shoelson, *Curr. Opin. Chem. Biol.* (1997), 1(2), 227–234; Cowburn, *Curr. Opin. Struct. Biol.* (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang, et al., 1993, *Cell* 72:767–778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang, et al., 1993, *Cell* 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signalling pathways recruited by specific growth factor receptors, as well as differentiation factor receptors.

Several receptor tyrosine kinases, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman, et al., *Oncogene* 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs, et al, *Oncogene* 8(1): 11–15, 1993). DNAs encoding mouse, rat and human FLK-1 have been isolated, and the nucleotide and encoded amino acid sequences reported (Matthews, et al., *Proc. Natl. Acad. Sci. USA,* 88:9026–30, 1991; Terman, et al., 1991, supra; Terman, et al.,*Biochem. Biophys. Res. Comm.* 187:1579–86, 1992; Sarzani, et al., supra; and Millauer, et al., *Cell* 72:835–846, 1993). Numerous studies such as those reported in Millauer, et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fins-like tyrosine kinase-1" (Flt-1) is related to FLK-1/KDR (DeVries, et al. *Science* 255;989–991, 1992; Shibuya, et al., *Oncogene* 5:519–524, 1990). An alternative designation for Flt-1 is "vascular endothelial cell growth factor receptor 1" (VEGFR-1). To date, members of the FLK-1/KDR/VEGFR-2 and flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine & Growth Factor Reviews* 7: 259–270, 1996). Vascular endothelial cell growth factor (VEGF) binds to Flt-1 with higher affinity than to FLK-1/KDR and is mitogenic toward vascular endothelial cells (Terman, et al., 1992, supra; Mustonen, et al. supra; DeVries, et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in adult organs such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman, et al., *Endocrinology* 133: 848–859, 1993; Kolch, et al., *Breast Cancer Research and Treatment* 36:139–155, 1995; Ferrara, et al., *Endocrine Reviews* 18(1):4–25, 1997; Ferrara, et al., *Regulation of Angiogenesis* (ed. L. D. Goldberg and E. M. Rosen), 209–232, 1997). In addition, VEGF has been implicated in the control and enhancement of vascular permeability (Connolly, et al., *J. Biol. Chem.* 264:20017–20024, 1989; Brown, et al., *Regulation of Angiogenesis* (ed. L. D. Goldberg and E. M. Rosen), 233–269, 1997).

Different forms of VEGF arising from alternative splicing of mRNA have been reported, including the four species described by Ferrara, et al. (*J. Cell. Biochem.* 47:211–218, 1991). Both secreted and predominantly cell-associated species of VEGF have been identified by Ferrara, et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.,* 159–164, 1998 and references cited therein).

Placenta growth factor (PlGF) has an amino acid sequence that exhibits significant homology to the VEGF sequence (Park, et al., *J. Biol. Chem.* 269:25646–54, 1994; Maglione, et al. *Oncogene* 8:925–31, 1993). As with VEGF, different species of PlGF arise from alternative splicing of mRNA, and the protein exists in dimeric form (Park, et al., supra). PlGF-1 and PlGF-2 bind to Flt-1 with high affinity, and PlGF-2 also avidly binds to neuropilin-1 (Migdal, et al, *J. Biol. Chem.* 273(35):22272–22278), but neither binds to FLK-1/KDR (Park, et al., supra). PlGF has been reported to potentiate both the vascular permeability and mitogenic effect of VEGF on endothelial cells when VEGF is present at low concentrations (purportedly due to heterodimer formation) (Park, et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper, et al, *Proc. Natl. Acad. Sci. U.S.A.* (1998), 95(20): 11709–11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki, et al,*Am. J. Pathol.* (1998), 153(2):395–403; Witzenbichler, et al, *Am. J. Pathol.* (1998), 153(2): 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki, et al, *J. Biol. Chem.* (1998), 273(14): 8413–8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen, et al, *Proc. Natl. Acad. Sci. U.S.A.* (1998), 95(2):548–553 and references therein).

VEGF-C and VEGF-D have been claimed to induce increases in vascular permeability in vivo in a Miles assay when injected into cutaneous tissue (PCT/US97/14696; WO98/07832, Witzenbichler, et al., supra). The physiological role and significance of these ligands in modulating vascular hyperpermeability and endothelial responses in tissues where they are expressed remains uncertain.

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler, et al., supra). Also, recent reports suggest neuropilin-1 (Migdal, et al, supra) or VEGFR-3/Flt-4 (Witzenbichler, et al., supra), or receptors other than KDR/VEGFR-2 may be responsible for the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118–120 (1997)). Until now, no direct evidence for the essential role of KDR in VEGF-mediated vascular hyperpermeability has been disclosed.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, *Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Application No. WO 94/10202; Kendall & Thomas, 1994, *Proc. Natl. Acad. Sci* 90:10705–09; Kim, et al., 1993, *Nature* 362:841–844), RNA ligands (Jellinek, et al., *Biochemistry* 33:10450–56; Takano, et al., 1993, *Mol. Bio. Cell* 4:358A; Kinsella, et al. 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475–478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. In particular, bis(indolylmaleimide) compounds have been described as inhibiting particular PKC serine/threonine kinase isoforms whose dysfunction is associated with altered vascular permeability in VEGF-related diseases (PCT WO97/40830; PCT WO97/4083 1).

The identification of effective small compounds which specifically inhibit signal transduction by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention provides a method of inhibiting the kinase activity of tyrosine kinases and serine/threonine kinases comprising the administration of a compound represented by formula (I):

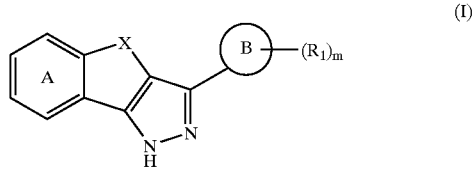

the racemic mixtures, racemic-diastereomeric mixtures, tautomers and optical isomers of said compounds and the pharmaceutically acceptable salts and the prodrugs thereof, wherein:

m is an integer from 1 to 10;

X represents a) an optionally substituted group of the formula —(CH$_2$)$_n$— in which n is 1, 2 or 3, b) carbonyl, c) oxygen, d) a group of the formula —C=NOR$_{10}$, in which R$_{10}$ is a C$_{1-4}$ alkyl group, e) a group of the formula NR$_{11}$, in which R$_{11}$ is —H, an optionally substituted C$_{1-4}$ alkyl group or an optionally substituted phenyl, or f) a group of formula S(O)$_p$ in which p is 0, 1 or 2;

B represents an alkyl, a cycloalkyl, an aryl, a pyridyl, a thienyl, a furyl or a pyrrolyl;

R$_1$ is —H; a halo; hydroxy; nitro; cyano; hydroxyamidino; aminomethyl; formanidomethyl; an optionally substituted alkenyloxy; an optionally substituted C$_{2-4}$ alkenyl; an optionally substituted C$_{2-4}$ alkynyl; or a group represented by the formula —Y—W;

Y is absent or a C$_{1-6}$ alkyl, C$_{1-6}$ alkoxy, —O—, —S— or —C(O)—;

W is —H, hydroxy, optionally substituted phenyl, C$_{1-6}$ alkoxy, or —NR$_2$R$_3$;

provided that when B is phenyl and R$_1$ is —Y—W and W is —NR$_2$R$_3$, R$_2$ and R$_3$ are each, independently, a) —H; b) a substituted C$_{1-6}$ alkyl group, provided that the substituent is not —NR$_6$R$_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with —NR$_9$(CH$_2$)$_{1-6}$OR$_4$, —NR$_9$(CH$_2$)$_{1-6}$CO$_2$R$_4$, —NR$_9$(CH$_2$)$_{1-6}$NR$_4$R$_5$, or an optionally substituted heterocycloalkyl; or when B is phenyl and R$_1$ is —Y—W and W is —NR$_2$R$_3$, R$_2$ and R$_3$, together with the nitrogen atom to which they are attached, can represent an optionally substituted heterocycloalkyl or an optionally substituted heteroaryl;

when B is not phenyl, R$_2$ and R$_3$ are each, independently, —H, an optionally substituted C$_{1-6}$ alkyl group, —NH(CH$_2$)$_{1-6}$NR$_4$R$_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, $R_2$ and $R_3$ together with the nitrogen atom to which they are attached represent an optionally substituted heterocycloalkyl or an optionally substituted heteroaryl;

$R_4$, $R_5$ and $R_9$ are for each occurrence, independently, —H or a $C_{1-6}$ alkyl; and ring A is optionally substituted with one or more substituents selected from the group consisting of a) a halo; b) a $C_{1-6}$ alkyl group optionally substituted with one or more substituents selected from the group consisting of hydroxy, halo, and —$NR_6R_7$; c) a $C_{1-6}$ alkoxy group optionally substituted with one or more substituents selected from the group consisting of hydroxy, halo, —$NR_6R_7$, an optionally substituted phenyl, and —$NR_{17}C(O)R_{19}$, provided that the substituents are not attached to the carbon which is attached to the oxygen of the alkoxy group; d) an optionally substituted phenoxy; e) hydroxy; f) a group of the formula —$C(O)R_{12}$ in which $R_{12}$ is a hydroxy, a $C_{1-6}$ alkoxy or —$NR_{13}R_{14}$; g) a group of the formula —$NR_{17}R_{18}$; h) a group of the formula —$NR_{17}C(O)R_{19}$; i) nitro; j) optionally substituted aralkyl; k) cyano; and l) a $C_{2-4}$ alkenyl group or a $C_{2-4}$ alkynyl group each of which is optionally substituted with one or more substituents selected from the group consisting of a $C_{1-6}$ alkyl group, a $C_{1-6}$ alkoxy group and a halo;

$R_6$ and $R_7$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_6$ and $R_7$ together with the nitrogen atom to which they are attached represent an optionally substituted heterocycloalkyl or an optionally substituted hetroaryl;

$R_{13}$ and $R_{14}$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_{13}$ and $R_{14}$ together with the nitrogen atom to which they are attached represent an optionally substituted heterocycloalkyl or an optionally substituted hetroaryl;

$R_{17}$ and $R_{18}$ are each, independently, selected from the group consisting of —H, a $C_{1-12}$ alkyl group, a $C_{3-12}$ cycloalkyl group, and phenyl; and $R_{19}$ is —H, an optionally substituted $C_{1-12}$ alkyl group, an optionally substituted $C_{3-12}$ cycloalkyl group, an optionally substituted phenyl or an optionally substituted aralkyl.

Certain compounds of formula I are known in the literature. Compounds of formula I in which X represents methylene, ethylene, trimethylene, vinylene, substituted methylene are disclosed in U.S. Pat. Nos. 3,932,430, 3,843,665 and 3,848,666. Compounds in which X represents carbonyl are disclosed in JP 60-130521. Compounds in which X represents O, ring A is unsubstituted and B is phenyl, 2,4-dimethylphenyl, 2-thienyl, 3-thienyl and 2-pyrrolyl are disclosed in *J. Het. Chem.* 1984, 21 (4) 937–943, *J. Org. Chem.* 1972, 37 (15) 2402 and *J Het Chem.* 1971, 855–859. A compound in which X represents S and ring A is unsubstituted and B is 2,4-dichlorophenyl is disclosed in *Monatsh Chem.* 1974, 105, 869. A compound of formula I in which X represents $SO_2$, ring A is unsubstituted and B is phenyl is disclosed in Liebigs Ann. Chem. 1974, 1248.

WO97/15308 discloses that 3-(4-methylphenyl)indeno[1,2-c]pyrazol-4(1H)-one oxime may be used to treat bone deficit conditions. 3-(3,4-Dimethoxyphenyl)-indeno[1,2-c]pyrazol-4(1H)-one oxime is commercially available.

Certain fused pyrazoles of formula I are commercially available but no pharmacological activity has been disclosed for these compounds. Compounds which are commercially available are as follows: 3-(2-thienyl)indeno[1,2-c]pyrazol-4(1H)-one and 3-phenyl-1H-benzofuro[3,2-c]-pyrazole.

Preferably, the protein kinase which is inhibited by the method of the invention is a tyrosine kinase. The tyrosine kinase can be a receptor tyrosine kinase or a non-receptor tyrosine kinase. The tryrosine kinases inhibited by the method of the invention can be selected from KDR, flt-1, TIE-2, Lck, Src, fyn or yes.

In another embodiment, the present invention provides a method of affecting angiogenesis in a mammal. The method involves administering to the mammal a compound represented by formula (I).

In another embodiment, the present invention provides a method of inhibiting the progression of a disease state in a mammal. The method involves administering to the mammal a compound represented by formula (I). The disease states which can be inhibited by the method are cancer, arthritis, atherosclerosis, psoriasis, hemangioma, myocardial angiogenesis, coronary and cerebral collateral vascularization, ischemic limb angiogenesis, corneal disease, rubeosis, neovascular glaucoma, macular degeneration, retinopathy of prematurity, wound healing, ulcers, Helicobacter related diseases, fractures, endometriosis, diabetic retinopathy, cat scratch fever, and thyroid hyperplasia, burns, trauma, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, sepsis, adult respiratory distress syndrome, multiple-organ dysfunction, ascites and tumor-associated effusions and edema.

In another embodiment, the present invention provides a method of inhibiting hyperpermeability or the production of edema in a mammal. The method involves administering to the mammal a compound represented by formula (I).

In another embodiment, the present invention involves inhibiting fertility or inducing abortifacient effects in a mammal. The method involves administering a compound represented by formula (I), provided that when $R_1$ is —H, an unsubstituted $C_{1-6}$ alkyl, an unsubstituted $C_{1-6}$ alkoxy, a halogen, or trifluoromethyl, ring A is substituted with at least one substituent that is not a halo, an optionally substituted $C_{1-6}$ alkyl or an optionally substituted $C_{1-6}$ alkoxy.

Another embodiment of the invention relates to compounds which inhibit the kinase activity of tyrosine kinases and serine/threonine kinases. The compounds can be represented by formula (I), provided that when $R_1$ is —H, an unsubstituted $C_{1-6}$ alkyl, an unsubstituted $C_{1-6}$ alkoxy, a halogen, or trifluoromethyl, ring A is substituted with at least one substituent that is not a halo, an optionally substituted $C_{1-6}$ alkyl or an optionally substituted $C_{1-6}$ alkoxy.

As used herein, alkyl groups include straight chained or branched $C_{1-8}$ hydrocarbons which are completely saturated. Preferably, alkyl groups have form 1–6 carbon atoms.

Cycloalkyl groups, as used herein, include $C_{3-8}$ hydrocarbons which are completely saturated.

A cycloalkylalkyl, as used herein, is a cycloalkyl that is linked to a compound by an alkyl group having from one to about six carbon atoms.

An aryl group, as used herein, includes carbocyclic aromatic rings systems such as phenyl and naphthyl.

Heteroaryl groups, as used herein, include heteroaryl ring systems (e.g., thienyl, pyridyl, pyrazolyl, isoxazolyl, thiadiazolyl, oxadiazolyl, indazolyl, furyl, pyrrolyl, imidazolyl, pyrazolyl, triazolyl, pyrimidinyl, pyridazinyl, pyrazinyl, thiazolyl, isoxazolyl, isothiazolyl, tetrazolyl, or oxadiazolyl) and heteroaryl ring systems in which a carbocyclic aromatic ring, carbocyclic non-aromatic ring or heteroaryl ring is fused to one or more other heteroaryl rings (e.g., benzo(b)thienyl, benzimidazole, benoxazolyl, benzofuryl, benzothiazolyl, indolyl, indolizinyl, tetrahydroindolyl, azaindolyl, indazolyl, quinolyl, isoquinolyl, imidazopyridinyl, purinyl, pyrrolo[2,3-d]pyrimidinyl, pyrazolo[3,4-d]pyrimidinyl) and their N-oxides.

An aralkyl group, as used herein, is an aryl that is linked to a compound by an alkyl group having from one to about six carbon atoms.

An heteroaralkyl group, as used herein, is a hetaryl that is linked to a compound by an alkyl group having from one to about six carbon atoms.

A heterocycloalkyl group, as used herein, is a non-aromatic ring system that has 3 to 9 atoms and includes at least one heteroatom, such as nitrogen, oxygen, or sulfur. Examples of heterocycloalkyl groups include piperazinyl, piperidinyl, homopiperazinyl, quinuclidinyl, azetidinyl, morpholinyl, thiomorpholinyl, thiazolidinyl, 8-azabicyclo[3.2.1]octanyl and 9-azabicyclo[3.3.1]nonyl.

The term "heterocycloalkylalkyl," as used herein, is a heterocycloalkyl that is linked to a compound by an alkyl group having from one to about six carbon atoms.

The term "heterocycle," as used herein, refers to heteroaryl groups and heterocycloalkyl groups.

The term "optionally substituted," unless otherwise defined herein, means substituted by one or more of the following a) a halo; b) a $C_{1-6}$ alkyl group optionally substituted with one or more substituents selected from the group consisting of hydroxy, halo, and —$NR_6R_7$; c) a $C_{1-6}$ alkoxy group optionally substituted with one or more substituents selected from the group consisting of hydroxy, halo, —$NR_6R_7$, an optionally substituted phenyl, and —$NR_{17}C(O)R_{19}$, provided that the substituents are not attached to the carbon which is attached to the oxygen of the alkoxy group; d) an optionally substituted phenoxy; e) hydroxy; f) a group of the formula —$C(O)R_{12}$ in which $R_{12}$ is a hydroxy, a $C_{1-6}$ alkoxy or —$NR_{13}R_{14}$; g) a group of the formula —$NR_{17}R_{18}$; h) a group of the formula —$NR_{17}C(O)R_{19}$; i) nitro; j) optionally substituted aralkyl; k) cyano; and l) a $C_{2-4}$ alkenyl group or a $C_{2-4}$ alkynyl group each of which is optionally substituted with one or more substituents selected from the group consisting of a $C_{1-6}$ alkyl group, a $C_{1-6}$ alkoxy group and a halo.

Preferably, the term "optionally substituted" as used herein means substituted by one or more of the following:

a) halo,
b) a $C_{1-6}$ alkyl group optionally substituted by one or more of the following: hydroxy, halo or an amino group of formula $NR_hR_j$ wherein $R_h$ and $R_j$ are as defined below,
c) a $C_{1-6}$ alkoxy group optionally substituted by one or more of the following: hydroxy, COOH, an amino group of formula $NR_hR_j$, or an amide of the formula $CONR_hR_j$, wherein $R_h$ and $R_j$ are as defined below provided that these groups are not attached to the carbon which is attached to the oxygen of the alkoxy group; or halo
d) optionally substituted phenoxy,
e) hydroxy,
f) a group of formula $COR_a$ or $SO_2R_a$ wherein $R_a$ is hydroxy, $(C_1-C_6)$alkyl, $(C_1-C_6)$alkoxy or $R_a$ represents a group of formula $NR_bR_c$;
   where $R_b$ and $R_c$ independently represent hydrogen, a $C_{1-12}$ alkyl group, a $C_{3-12}$ cycloalkyl group, phenyl $(C_0-C_6)$alkyl or heterocyclyl-$(C_0-C_6)$alkyl (heterocyclyl is tetrahydrofuranyl, furanyl, 1,3-benzodioxole, pyridinyl, or thiophenyl) wherein the alkyl group, the cycloalkyl group, phenyl or heterocyclyl-$(C_0-C_6)$alkyl are optionally substituted by one or more of the following: hydroxy, $(C_1-C_6)$-hyrdroxy, halo, nitro, $(C_1-C_6)$alkyl, $(C_1-C_6)$alkoxy, —O-$(C_1-C_6)$alkyl-hydroxy a $C_{3-12}$ cycloalkyl group or an amino group of formula $NR_hR_j$;
   where $R_h$ and $R_j$ independently represent hydrogen, $(C_1-C_{12})$alkyl, $(C_3-C_6)$cycloalkyl, $(C_3-C_6)$heterocycloalkyl-$(C_0-C_6)$alkyl $(C_1-C_6)$alkenyl, $(C_1-C_6)$alkynyl, $(C_3-C_6)$cycloalkenyl-$(C_0-C_6)$alkyl, hydroxy$(C_1-C_6)$alkyl, amino$(C_1-C_6)$alkyl, $(C_1-C_6)$alkoxy$(C_1-C_6)$alkyl, mono- or di-$(C_1-C_6)$alkylamino$(C_1-C_6)$alkyl, morpholinyl-$(C_1-C_6)$alkyl, pyrrolidinyl-$(C_1-C_6)$alkyl, pyridinyl, phenyl $(C_0-C_6)$alkyl where the phenyl portion is optionally substituted by one or more moieties selected from the group consisting of halo, hydroxy, nitro, amino, mono- or di-$(C_1-C_6)$alkylamino, $(C_1-C_6)$alkyl and $(C_1-C_6)$alkoxy; or $R_h$ and $R_j$ together with the nitrogen atom to which they are attached represent a four, five, six or seven membered heterocyclic ring which optionally contains one or more additional hetero atoms selected from O, S and N and is optionally substituted by a $C_{1-6}$ alkyl group or a heterocycle,
   or $R_b$ and $R_c$ are taken together with the nitrogen atom to which they are attached to form an optionally substituted 4-, 5-, 6- or 7-membered ring where said ring optionally contains one or more additional heteroatoms selected from the group consisting of O, N and S, and said ring is optionally substituted by $(C_1-C_6)$alkyl, pyridinyl, phenyl$(C_0-C_6)$alkyl, phenyl$(C_2-C_6)$alkenyl, where the phenyl portion is optionally substituted by one or more moieties selected from the group consisting of Br, Cl, F, I, hydroxy, nitro, amino, mono- or di-$(C_1-C_6)$alkylamino, $(C_1-C_6)$alkyl and $(C_1-C_6)$alkoxy;
g) a group of formula $NR_dR_e$ in which $R_d$ and $R_e$ are independently selected from hydrogen, a $C_{1-12}$ alkyl group, a $C_{3-12}$ cycloalkyl group, $S(O)_2$-phenyl, phenyl, a heterocycloalkyl-$(C_1-C_6)$alkyl, wherein the heterocycloalkyl is a four, five, six or seven menbered heterocyclic ring which has one or more heteroatoms selected from the group consisting of O, S and N, or $R_d$ and $R_e$ are each, independently, a group of formula $COR_f$
   wherein $R_f$ represents hydrogen, $NR_bR_c$, $(C_1-C_6)$alkoxy, amino-$(C_1-C_6)$alkoxy-$(C_1-C_6)$alkoxy, mono-$(C_1-C_6)$alkyl-amino-$(C_1-C_6)$alkoxy-$(C_1-C_6)$alkoxy, N,N-di-$(C_1-C_6)$alkyl-amino-$(C_1-C_6)$alkoxy-$(C_1-C_6)$alkoxy, a $C_{1-12}$ alkyl group, a $C_{3-12}$ cycloalkyl group, a phenyl $C_{1-6}$ alkyl group or phenyl wherein in each case the alkoxy, the alkyl group, the cycloalkyl group and phenyl are optionally substituted by one or more of the following: halo, hydroxy, nitro, $(C_1-C_6)$alkyl, $(C_1-C_6)$alkoxy, di-$(C_1-C_6)$alkyl-amino-$(C_1-C_6)$alkoxy, pyrrolidine which is optionally substituted with a $(C_1-C_6)$alkyl, or an amino group of formula $NR_hR_j$ wherein $R_h$ and $R_j$ are as defined above, h) a group of formula $O(CH_2)_m R_g$ in which m is 2, 3, 4 or 5 and $R_g$ represents hydroxy or a group of formula $NR_dR_e$ in which $R_d$ and $R_e$ are as defined above; or $R_g$ represents a group of formula $COR_a$ wherein $R_a$ is as defined above and m is 1, 2, 3, 4 or 5, i) nitro, j) optionally substituted phenyl $C_{1-6}$ alkyl, k) optionally substituted phenyl $C_{1-6}$ alkoxy l) cyano, m) a $C_{3-6}$alkenyloxy group, n) a pyridyloxy or pyridylthio group in which the pyridine ring is optionally substituted by one or more of the following: trifluoromethyl or nitro, o) hydroxyamidino, p) aminomethyl, q) formamidomethyl, r) a $C_{1-6}$ alkythio group s) phenyl t) a $C_{2-4}$ alkenyl group or a $C_{2-4}$ alkynyl group each of which is optionally substituted by phenyl which is optionally substituted by one or more of the following: a $C_{1-6}$ alkyl group, a $C_{1-6}$ alkoxy group or halo, u) CHO, v) dihydroxyborane w) tetrazolyl.

In one embodiment, when B is an optionally substituted pyridyl the pyridine ring may be in the form of its N-oxide.

When $NR_6R_7$ or $NR_{13}R_{14}$ represents a saturated heterocycloalkyl ring, the ring is preferably morpholino, perhydrothiazinyl, piperidino, pyrrolidinyl, piperazinyl or 4-methylpiperazinyl.

The term "optionally substituted group of the formula $—(CH_2)_n—$" means, for example, a group of the formula $—(CH_2)_n—$ which is substituted by one or more of the following: hydroxy or a $C_{1-4}$ alkyl group wherein the alkyl group is optionally further substituted by a group of formula $NR_{20}R_{21}$ wherein $R_{20}$ and $R_{21}$ independently represent H or a $C_{1-6}$ alkyl group.

It will be understood that any group mentioned herein which contains a chain of three or more atoms signifies a group in which the chain may be straight or branched. For example, an alkyl group may comprise propyl, which includes n-propyl and isopropyl, and butyl, which includes n-butyl, sec-butyl, isobutyl and tert-butyl. The term $C_{3-12}$ cycloalkyl group includes bridged groups for example adamantyl. The term 'halo' as used herein signifies fluoro, chloro, bromo and iodo.

Compounds of formula I may exist as salts with pharmaceutically acceptable acids. The present invention includes such salts. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. These salts may be prepared by methods known to those skilled in the art.

Certain compounds of formula I which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

The compounds of this invention are useful as inhibitors of serine/threonine and tyrosine kinases. In particular, the compounds of this invention are useful as inhibitors of tyrosine kinases that are important in hyperproliferative diseases, especially in the process of angiogenesis. Since these compounds are anti-angiogenic, they are important substances for inhibiting the progression of disease states where angiogenesis is an important component.

Preferred definitions of the substituents are now given.

X is preferably —S—, —CH$_2$—, —CO—, —SO—, —SO$_2$—, or —C(CH$_3$)$_2$—. Most preferably, X is —S— or —CH$_2$—.

Preferably B represents phenyl, naphthyl, thienyl, pyridyl, furyl, or pyrrolyl. More preferably, B is phenyl, thien-2-yl or thien-3-yl.

$R_1$ can be selected from the group consisting of optionally substituted alkoxy (particularly methoxy, 3-morpholinopropoxy, 2-morpholinoethoxy, 3-carboxypropoxy, carboxymethoxy, 2-carboxyethoxy, 2-carbamoylethoxy, carbamoylmethoxy, 3-carbamoylpropoxy, 2-piperidinoethoxy, 2-(piperazin-1-yl)ethoxy, 2-(pyrrolidin-1-yl)ethoxy, 2-dimethylaminoethoxy, 2-(perhydro-thiazin-4-yl)ethoxy, 3-piperidinopropoxy, 3-(piperazin-1-yl)propoxy, 3-(pyrrolidin-1yl)-propoxy, 3-dimethylaminopropoxy, 3-(perhydrothiazin-4-yl)propoxy), lower alkyl (particularly methyl), halo (particularly fluoro and chloro), aryl (particularly phenyl), hydroxy, aryloxy (particularly phenoxy), arylalkoxy (particularly benzyloxy), di-lower-alkylamino (particularly dimethylamino), polyhalo-lower-alkyl, polyhalo-loweralkoxy (particularly difluoromethoxy), nitro, cyano, loweralkylthio (particularly methylthio), carboxy, loweralkoxycarbonyl (particularly methoxycarbonyl), amido (particularly acetamido and benzamido) and optionally substituted carbamoyl (particularly carbamoyl, N-methylcarbamoyl, N-phenylcarbamoyl) and a pyridyloxy or pyridylthio group in which the pyridine ring is optionally substituted by one or more of the following: trifluoromethyl or nitro.

B and $R_1$ taken together can be selected from the group consisting of 4-pyridyl, 2-formamidomethyl-4-pyridyl, 2-aminomethyl-4-pyridyl, 2-(hydroxyamidino)-4-pyridyl, 2-carbamoyl-4-pyridyl, 4-pyridyl-N-oxide, 2-chloro-4-pyridyl, 2-cyano-4-pyridyl, 5-methyl-2-furyl, 5-(2-nitro-4-trifluoromethylphenyl)fur-2-yl, phenyl, 4-methoxyphenyl, 3-methoxyphenyl, 2-methoxyphenyl, 3,4-dimethoxyphenyl, 3,4,5-trimethoxyphenyl, 4-(3-morpholino-propoxy)phenyl, 4-(2-morpholinoethoxy)phenyl, 4-(3-carboxypropoxy) phenyl, 4-carboxymethoxyphenyl, 4-(3-carbamoylpropoxy) phenyl, 4-carbamoylmethoxyphenyl, 3-(3-morpholinopropoxy)phenyl, 3-(2-morpholinoethoxy)phenyl, 3-(3-carboxy-propoxy)phenyl, 4-carboxymethoxyphenyl, 3-(3-carbamoylpropoxy)phenyl, 3-carbamoylmethoxyphenyl, 2-hydroxyphenyl, 3-hydroxyphenyl, 4-hydroxyphenyl, 3-hydroxy-4-methoxyphenyl, 4-hydroxy-3-methoxyphenyl, 4-difluoromethoxyphenyl, 3-nitrophenyl, 4-nitrophenyl, 3,5-di-tert-butyl-4-hydroxyphenyl, 4-methylphenyl, 4-fluorophenyl, 2-chlorophenyl, 3-chlorophenyl, 4-chlorophenyl, 2,4-dichlorophenyl, 2-chloro-5-nitrophenyl, 4-fluoro-2-chlorophenyl, 4-methylthiophenyl, 4-biphenylyl, 3-phenoxyphenyl, 4-phenoxyphenyl, 4-benzyloxyphenyl, 4-dimethylaminophenyl, 4-diethylaminophenyl, 4-methoxycarbonylphenyl, 4-carbamoylphenyl, 4-cyanophenyl, 4-N-methylcarbamoylphenyl, 4-N-phenylcarbamoylphenyl, 4-acetamidophenyl, 4-benzamidophenyl, 4-carboxyphenyl, 4-[N-(2-diethylaminoethyl)carbamoyl]phenyl, 4-(prop-1-enyloxy)phenyl, 3-(2-hydroxyethoxy)phenyl, 3-(N-(2-diethylaminoethyl)-carbamoylmethoxy)phenyl, 3-[3-(N-(2-diethylaminoethyl)carbamoyl)propoxy]phenyl, 4-(N-(2-diethylaminoethyl)carbamoylmethoxy)phenyl, 4-[3-(N-(2-diethylaminoethyl)-carbamoyl)propoxy]phenyl, 2-furyl, 5-[3,5-bis(trifluoromethyl)phenyl]-2-furyl, 3-bromo-2-thienyl, 5-methoxy-2-furyl, 5-(2-nitro-4-trifluoromethylphenyl)-2-furyl, 3-N-(2-morpholinoethyl)carbamoylmethoxy)phenyl, 3-[3-(N-(2-morpholinoethyl)carbamoyl)-propoxyphenyl], 4-(N-(2-morpholinoethyl)-carbamoylmethoxy)phenyl, 4-(morpholinoacetamido) phenyl and 4-[3-(N-(2-morpholinoethyl)carbamoyl)-propoxy]phenyl.

In a preferred embodiment, $R_1$ is —$CH_2NR_2R_3$ in which $R_2$ and $R_3$, taken together with the nitrogen to which they are attached, is an optionally substituted heterocycloalkyl or $R_1$ is —$CH_2NR_2R_3$ in which $R_2$ is —H and $R_3$ is an optionally substituted heterocycloalkyl or $R_1$ is —$CH_2NR_2R_3$ in which $R_2$ is —H and $R_3$ is an optionally substituted heterocycloalkylalkyl. Preferably, the heterocycloalkyl or the heterocycloalkyl portion of the heterocycloalkylalkyl is selected from the group consisting of piperizine, a piperidine, homopiperazine, quinuclidine, azetidine, morpholine, thiomorpholine, pyrrolidine, thiazolidine, 8-azabicyclo[3.2.1]octane and 9-azabicyclo[3.3.1]nonane. Preferred substituents for a heterocycloalkyl or the heterocycloalkyl portion of a heterocycloalkylalkyl are a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

In another preferred embodiment, $R_1$ is —$CH_2NR_2R_3$ in which $R_2$ is —H and $R_3$ is a heteroaryl or $R_1$ is —$CH_2NR_2R_3$ in which $R_2$ is —H and $R_3$ is a heteroaralkyl, in which the heteroaryl or the heteroaryl portion of the heteroaralkyl is substituted with a —$NR_9(CH_2)_{1-6}OR_4$, a —$NR_9(CH_2)_{1-6}CO_2R_4$, a —$NR_9(CH_2)_{1-6}NR_4R_5$, or a heterocycloalkyl which is optionally substituted with a lower alkyl group. Preferably, the heteroaryl or the heteroaryl portion of the heteroaralkyl is selected from the group consisting of pyridyl, imidazolyl, furyl, pyrrolyl, thienyl, oxazolyl, thiazolyl, isoxazolyl, thiadiazolyl, oxadiazolyl, pyrimidinyl, pyrazinyl, pyridazinyl, quinolyl, isoquinolyl, indazolyl, benzoxazolyl, benzofuryl, benzothiazolyl, indolizinyl, imidazopyridinyl and benzo(b)thienyl. In one embodiment, the heteroaryl is pyridinyl. Pyridinyl is preferably substituted with 2-(N,N-dimethylamino)ethylamino.

In one embodiment, ring A can be substituted with one or more substituents selected from the group consisting of halo (particularly fluoro), optionally substituted lower alkoxy (particularly methoxy, 3-morpholinopropoxy, 2-morpholinoethoxy, 3-carboxypropoxy, carboxymethoxy, 2-carboxyethoxy, 2-carbamoylethoxy, 3-carbamoylpropoxy, 2-piperidinoethoxy, 2-(piperazin-1-yl)ethoxy, 2-(pyrrolidin-1-yl)ethoxy, 2-dimethylaminoethoxy, 2-(perhydrothiazin-1-yl)ethoxy, 3-piperidinopropoxy, 3-(piperazin-1-yl)propoxy, 3-(pyrrolidin-1-yl)propoxy, 3-dimethylaminopropoxy, 3-(perhydrothiazin-4-yl)propoxy), carbamoylmethoxy, hydroxypropyloxy, hydroxyethoxy, (3-morpholino)propoxy and 2-morpholino)ethoxy), amido (particularly acetamido and benzamido), optionally substituted carbamoyl (particularly carbamoyl, N-methyl-carbamoyl and N-phenylcarbamoyl), carboxy, nitro and amino.

In another embodiment, ring A is substituted with one or more substituents selected from the group consisting of 6,7-dimethoxy, 6,7,8-trimethoxy, 6-fluoro, 6-acetamido, 7-methoxy, 6-carbamoyl, 6-(N-methyl-carbamoyl), 6-(N-phenylcarbamoyl), (3-morpholino)propoxy and 2-morpholino)-ethoxy.

In a preferred embodiment, ring A is substituted with —$CH_2NR_6R_7$ in which $R_6$ and $R_7$, taken together with the nitrogen to which they are attached, is an optionally substituted heterocycloalkyl or ring A is substituted with —CH$_2$NR$_6$R$_7$ in which R$_6$ is —H and R$_7$ is an optionally substituted heterocycloalkyl or ring A is substituted with —CH$_2$NR$_6$R$_7$ in which R$_6$ is —H and R$_7$ is an optionally substituted heterocycloalkylalkyl. Preferably, the heterocycloalkyl or the heterocycloalkyl portion of the heterocycloalkylalkyl is piperizine, a piperidine, homopiperazine, quinuclidine, azetidine, morpholine, thiomorpholine, pyrrolidine, thiazolidine, 8-azabicyclo[3.2.1]octanyl and 9-azabicyclo[3.3.1]nonane. Preferred substituents for a heterocycloalkyl or the heterocycloalkyl portion of the heterocycloalkylalkyl are a) a lower alkyl which is optionally substituted with —NR$_4$R$_5$, —OR$_4$, heterocycloalkyl, or —C(O)$_2$R$_4$; b) hydroxyl; c) —C(O)$_2$R$_4$; d) —NR$_4$R$_5$, wherein R$_4$ and R$_5$ are each, independently, optionally substituted with —NR$_4$R$_5$, —OR$_4$, heterocycloalkyl or —C(O)$_2$R$_4$; e) heterocycloalkyl which is optionally substituted with a lower alkyl, phenyl, heteroaryl, or heterocycloalkyl which is optionally substituted by a lower alkyl; f) —OR$_4$, wherein R$_4$ is optionally substituted with a —NR$_4$R$_5$, —OR$_4$, heterocycloalkyl, or —C(O)$_2$R$_4$; g) —COR$_4$, wherein R$_4$ is optionally substituted with —NR$_4$R$_5$, —OR$_4$, heterocycloalkyl, or —C(O)$_2$R$_4$; h) —NR$_4$C(O)$_2$R$_5$; and i) —NR$_4$C(O)R$_5$, wherein R$_5$ is optionally substituted with —OR$_4$, —NR$_4$R$_5$, a heterocycloalkyl which is optionally substituted with a lower alkyl.

In another preferred embodiment, ring A is substituted with —CH$_2$NR$_6$R$_7$ in which R$_6$ is —H and R$_7$ is an optionally substituted heteroaryl or ring A is substituted with —CH$_2$NR$_6$R$_7$ in which R$_6$ is —H and R$_7$ is an optionally substituted heteroaralkyl. Preferably, pyridyl, imidazolyl, furyl, pyrrolyl, thienyl, oxazolyl, thiazolyl, isoxazolyl, thiadiazolyl, oxadiazolyl, pyrimidinyl, pyrazinyl, pyridazinyl, quinolyl, isoquinolyl, indazolyl, benzoxazolyl, benzofuryl, benzothiazolyl, indolizinyl, imidazopyridinyl and benzo(b)thienyl. Preferred substituents for a heteroaryl or the heteroaryl portion of the heteroaralkyl are a) a lower alkyl which is optionally substituted with —NR$_4$R$_5$, —OR$_4$, heterocycloalkyl, or —C(O)$_2$R$_4$; b) hydroxyl; c) —C(O)$_2$R$_4$; d) —NR$_4$R$_5$, wherein R$_4$ and R$_5$ are each, independently, optionally substituted with —NR$_4$R$_5$, —OR$_4$, heterocycloalkyl or —C(O)$_2$R$_4$; e) heterocycloalkyl which is optionally substituted with a lower alkyl, phenyl, heteroaryl, or heterocycloalkyl which is optionally substituted by a lower alkyl; f) —OR$_4$, wherein R$_4$ is optionally substituted with a —NR$_4$R$_5$, —OR$_4$, heterocycloalkyl, or —C(O)$_2$R$_4$; g) —COR$_4$, wherein R$_4$ is optionally substituted with —NR$_4$R$_5$, —OR$_4$, heterocycloalkyl, or —C(O)$_2$R$_4$; h) —NR$_4$C(O)$_2$R$_5$; and i) —NR$_4$C(O)R$_5$, wherein R$_5$ is optionally substituted with —OR$_4$, —NR$_4$R$_5$, a heterocycloalkyl which is optionally substituted with a lower alkyl.

Specific compounds of the present invention include:

3-(3,4,5-trimethoxyphenyl)-1,4-dihydroindeno[1,2-c]pyrazole,
3-(1,4-dihydroindeno[1,2-c]pyrazol-3-yl)phenol,
3-phenyl-1H-[1]benzothieno[3,2-c]pyrazole,
3-(2-thienyl)-1H-[1]benzothieno[3,2-c]pyrazole,
3-phenyl-1H-[1]benzothieno[3,2-c]pyrazole 4-oxide,
3-phenyl-1H-[1]benzothieno[3,2-c]pyrazole 4,4-dioxide,
3-(2-thienyl)-1H-[1]benzothieno[3,2-c]pyrazole,
3-phenylindeno[1,2-c]pyrazol-4(1H)-one oxime,
3-(3,4-dimethoxyphenyl)indeno[1,2-c]pyrazol-4(1H)-one oxime,
3-(4-methylphenyl)indeno[1,2-c]pyrazol-4(1H)-one oxime,
3-(2-thienyl)indeno[1,2-c]pyrazol-4(1H)-one,
3-phenyl-1H-benzofuro[3,2-c]pyrazole,
1,4-dihydro-3-phenylpyrazolo[4,3-b]indole,
1,4-dihydro-4-methyl-3-phenylpyrazolo[4,3-b]indole,
4,4-dimethyl-3-phenyl-1,4-dihydroindeno[1,2-c]pyrazole,
4-(1,4-dihydroindeno[1,2-c]pyrazol-3-yl)benzoic acid,
methyl 4-(1,4-dihydroindeno[1,2-c]pyrazol-3-yl)benzoate,
4'-(1,4-dihydroindeno[1,2-c]pyrazol-3-yl)acetanilide,
4'-(1,4-dihydroindeno[1,2-c]pyrazol-3-yl)-3-morpholinopropionanilide,
4'-(1,4-dihydroindeno[1,2-c]pyrazol-3-yl)morpholinoacetanilide,
4'-(1,4-dihydroindeno[1,2-c]pyrazol-3-yl)benzanilide,
N-(3-phenyl-1,4-dihydroindeno[1,2-c]pyrazol-6-yl)acetamide,
3-morpholino-N-(3-phenyl-1,4-dihydroindeno[1,2-c]pyrazol-6-yl)propionamide,
N-(3-phenyl-1,4-dihydroindeno[1,2-c]pyrazol-6-yl)benzanilide,
4-(1,4-dihydroindeno[1,2-c]pyrazol-3-yl)benzamide,
N-methyl-4-(1,4-dihydroindeno[1,2-c]pyrazol-3-yl)benzamide,
4-(1,4-dihydroindeno[1,2-c]pyrazol-3-yl)benzanilide,
N-(2-diethylaminoethyl)-4-(1,4-dihydroindeno[1,2-c]pyrazol-3-yl)benzamide,
N-(2-morpholinoethyl)-4-(1,4-dihydroindeno[1,2-c]pyrazol-3-yl)benzamide,
4-(1,4-dihydroindeno[1,2-c]pyrazol-3-yl)phenol,
3-[3-(2-morpholinoethoxy)phenyl]-1,4-dihydroindeno[1,2-c]pyrazole,
3-(2-thienyl)-1,4-dihydroindeno[1,2-c]pyrazol-6-ol,
6-(2-morpholinoethoxy)-3-(2-thienyl)-1,4-dihydroindeno[1,2-c]pyrazole,
3-[3-(2-hydroxyethoxy)phenyl]-1,4-dihydroindeno[1,2-c]pyrazole,
3-(1,4-dihydroindeno[1,2-c]pyrazol-3-yl)phenoxyacetic acid,
ethyl 3-(1,4-dihydroindeno[1,2-c]pyrazol-3-yl)phenoxyacetate,
3-(1,4-dihydroindeno[1,2-c]pyrazol-3-yl)phenoxyacetamide,
N-(2-diethylaminoethyl)-3-(1,4-dihydroindeno[1,2-c]pyrazol-3-yl)phenoxyacetamide,
N-(2-morpholinoethyl)-3-(1,4-dihydroindeno[1,2-c]pyrazol-3-yl)phenoxyacetamide,
4-{3-(1,4-dihydroindeno[1,2-c]pyrazol-3-yl)phenoxy}butyric acid,
ethyl 4-{3-(1,4-dihydroindeno[1,2-c]pyrazol-3-yl)phenoxy}butyrate,
4-{3-(1,4-dihydroindeno[1,2-c]pyrazol-3-yl)phenoxy}butyramide,
N-(2-diethylaminoethyl)-4-{3-(1,4-dihydroindeno[1,2-c]pyrazol-3-yl)phenoxy}-butyramide,
N-(2-morpholinoethyl)-4-{3-(1,4-dihydroindeno[1,2-c]pyrazol-3-yl)phenoxy}-butyramide,
3-(2-thienyl)-1,4-dihydroindeno[1,2-c]pyrazole-6-carboxamide,
N-methyl-3-(2-thienyl)-1,4-dihydroindeno[1,2-c]pyrazole-6-carboxamide,
N-(2-morpholinoethyl)-3-phenyl-1,4-dihydroindeno[1,2-c]pyrazole-6-carboxamide,
3-(2-thienyl)-1,4-dihydroindeno[1,2-c]pyrazole-6-carboxanilide;
N-(3-phenyl-1,4-dihydroindeno[1,2-c]pyrazol-6-yl)acetamide,
3-phenyl-1,4-dihydroindeno[1,2-c]pyrazol-6-ylamine,
3-(4-nitrophenyl)-1,4-dihydroindeno[1,2-c]pyrazole,
4-(1,4-dihydroindeno[1,2-c]pyrazol-3-yl)aniline, 4-(4,5-dihydro-1H-benzo[g]indazol-3-yl)pyridine 1-oxide,
3-(2-chloro-4-pyridyl)-4,5-dihydro-1H-benzo[g]indazole,
4-(4,5-dihydro-1H-benzo[g]indazol-3-yl)-2-pyridinecarbonitrile,
4-(4,5-dihydro-1H-benzo[g]indazol-3-yl)-2-pyridinecarboxamide oxime,
4-(4,5-dihydro-1H-benzo[g]indazol-3-yl)-2-pyridinecarboxamide,
{[4-(4,5-dihydro-1H-benzo[g]indazol-3-yl)-2-pyridyl]methyl}ammonium chloride,
N-{[4-(4,5-dihydro-1H-benzo[g]-indazol-3-yl)-2-pyridyl]methyl}formamide,
2-[3-(1,4-dihydroindeno[1,2-c]pyrazol-3-yl)phenoxy]ethanol,
2-morpholinoethyl 4-(1,4-dihydroindeno[1,2-c]pyrazol-3-yl)benzoate,
3-(3-nitrophenyl)-1,4-dihydroindeno[1,2-c]pyrazole,
3-(4-thiomethoxyphenyl)-1,4-dihydroindeno[1,2-c]pyrazole,
3-(2-naphthyl)-1,4-dihydroindeno[1,2-c]pyrazole,
3-(4-difluoromethoxyphenyl)-1,4-dihydroindeno[1,2-c]pyrazole,
3-(4-acetamidophenyl)-4,5-dihydro-2H-benz[g]indazole,
3-(4-bromo-2-thienyl)-4,5-dihydroindeno[1,2-c]pyrazole,
3-(4-benzyloxyphenyl)-4,5-dihydro-2H-benz[g]indazole,
6,7-dimethoxy-3-(3-phenoxyphenyl)-1,4-dihydroindeno-[1,2-c]pyrazole,
3-[4-(5-trifluoromethyl-2-pyridyloxy)phenyl]-1,4-dihydroindeno[1,2-c]pyrazole,
6,7,8-trimethoxy-3-(2,3,4-trimethoxyphenyl)-1,4-dihydroindeno[1,2-c]pyrazole,
4-(1,4-dihydroindeno[1,2-c]pyrazol-3-yl)-2-hydroxymethyl)phenol,
2-methoxy-5-(1,4-dihydroindeno[1,2-c]pyrazol-3-yl)phenol,
2-chloro-4-(1,4-dihydroindeno[1,2-c]pyrazol-3-yl)phenol,
2-methoxy-4-(1,4-dihydroindeno[1,2-c]pyrazol-3-yl)phenol,
3-chloro-4-(1,4-dihydroindeno[1,2-c]pyrazol-3-yl)phenol,
2-[4-(1,4-dihydroindeno[1,2-c]pyrazol-3-yl)phenoxy]acetamide,
4'-(1,4-dihydroindeno[1,2-c]pyrazol-3-yl)diethylamino-acetanilide,
4-(1H-[1]benzothieno[3,2-c]pyrazol-3-yl)benzamide,
3-(4-aminophenyl)-1H-[1]benzothieno[3,2-c]pyrazole,
3-(4-methoxyphenyl)-1H-benzothieno[3,2-c]pyrazole,
3-(4-hydroxyphenyl)-1H-[1]benzothieno[3,2-c]pyrazole,
N-(3-phenyl-1,4-dihydroindeno[1,2-c]pyrazol-6-yl)benzamide,
N-(2-morpholinoethyl)-4-(1,4-dihydroindeno[1,2-c]pyrazol-3-yl)benzamide,
4-(1,4-dihydroindeno[1,2-c]pyrazol-3-yl)benzonitrile,
7-methoxy-3-(4-methylsulphonylphenyl)-4,5-dihydro-2H-benz[g]indazole,
4-methyl-3-phenyl-1,4-dihydroindeno[1,2-c]pyrazol-4-ol,
N-[2-(N,N-diethylamino)ethyl]-4-(1,4-dihydroindeno[1,2-c]pyrazol-3-yl)benzamide,
N-[2-(N,N-dimethylamino)ethyl]-4-(1,4-dihydroindeno[1,2-c]pyrazol-3-yl)benzamide,
N-[2-(N,N-dipropylamino)ethyl]-4-(1,4-dihydroindeno[1,2-c]pyrazol-3-yl)benzamide,
N-[2-(N,N-di-isopropylamino)ethyl]-4-(1,4-dihydroindeno[1,2-c]pyrazol-3-yl)benzamide,
N-[3-(N,N-diethylamino)propyl]-4-(1,4-dihydroindeno[1,2-c]pyrazol-3-yl)benzamide,
N-[3-(N,N-dimethylamino)propyl]-4-(1,4-dihydroindeno[1,2-c]pyrazol-3-yl)benzamide,
N-[3-(N,N-dipropylamino)propyl]-4-(1,4-dihydroindeno[1,2-c]pyrazol-3-yl)benzamide,
N-[3-(N,N-di-isopropylamino)propyl]-4-(1,4-dihydroindeno[1,2-c]pyrazol-3-yl)benzamide,
N-(2-Piperidinoethyl)-4-(1,4-dihydroindeno[1,2-c]pyrazol-3-yl)benzamide,
N-(2-Piperidinopropyl)-4-(1,4-dihydroindeno[1,2-c]pyrazol-3-yl)benzamide,
N-(2-Morpholinoethyl)-4-(1,4-dihydroindeno[1,2-c]pyrazol-3-yl)benzamide,
N-(2-Morpholinopropyl)-4-(1,4-dihydroindeno[1,2-c]pyrazol-3-yl)benzamide,
N-[2-(Piperazin-1-yl)ethyl]-4-(1,4-dihydroindeno[1,2-c]pyrazol-3-yl)benzamide,
N-[3-(Piperazin-1-yl)propyl]-4-(1,4-dihydroindeno[1,2-c]pyrazol-3-yl)benzamide,
N-[2-(Pyrrolidin-1-yl)ethyl]-4-(1,4-dihydroindeno[1,2-c]pyrazol-3-yl)benzamide,
N-[3-(Pyrrolidin-1-yl)propyl]-4-(1,4-dihydroindeno[1,2-c]pyrazol-3-yl)benzamide,
N-[2-(4-Methylpiperazin-1-yl)ethyl]-4-(1,4-dihydroindeno[1,2-c]pyrazol-3-yl)benzamide,
N-[3-(4-Methylpiperazin-1-yl)propyl]-4-(1,4-dihydroindeno[1,2-c]pyrazol-3-yl)benzamide,
N-[2-(Thiomorpholin-1-yl)ethyl]-4-(1,4-dihydroindeno[1,2-c]pyrazol-3-yl)benzamide,
N-[3-(Thiomorpholin-1-yl)propyl]-4-(1,4-dihydroindeno[1,2-c]pyrazol-3-yl)benzamide,
N-[2-(Homopiperazin-1-yl)ethyl]-4-(1,4-dihydroindeno[1,2-c]pyrazol-3-yl)benzamide,
N-[3-(Homopiperazin-1-yl)propyl]-4-(1,4-dihydroindeno[1,2-c]pyrazol-3-yl)benzamide,
N-[2-(Perhydroazepin-1-yl)ethyl]-4-(1,4-dihydroindeno[1,2-c]pyrazol-3-yl)benzamide,
N-[3-(Perhydroazepin-1-yl)propyl]-4-(1,4-dihydroindeno[1,2-c]pyrazol-3-yl)benzamide,
N-Isopropyl-4-(1,4-dihydroindeno[1,2-c]pyrazol-3-yl)benzamide,
N-But-2-yl-4-(1,4-dihydroindeno[1,2-c]pyrazol-3-yl)benzamide,
N-Methyl-4-(1,4-dihydroindeno[1,2-c]pyrazol-3-yl)benzamide,
N-Ethyl-4-(1,4-dihydroindeno[1,2-c]pyrazol-3-yl)benzamide,
N-Pentyl-4-(1,4-dihydroindeno[1,2-c]pyrazol-3-yl)benzamide,
N-(2-Bromoethyl)-4-(1,4-dihydroindeno[1,2-c]pyrazol-3-yl)benzamide,
N-(3,3,3-trifluoroprop-1-yl-4-(1,4-dihydroindeno[1,2-c]pyrazol-3-yl)benzamide,
N-(Cyclopropylmethyl)-4-(1,4-dihydroindeno[1,2-c]pyrazol-3-yl)benzamide,
N-Cyclopentyl-4-(1,4-dihydroindeno[1,2-c]pyrazol-3-yl)benzamide,
N-(Cyclohexylmethyl)-4-(1,4-dihydroindeno[1,2-c]pyrazol-3-yl)benzamide,
N-(2-Chlorocyclopentyl)-4-(1,4-dihydroindeno[1,2-c]pyrazol-3-yl)benzamide,
N-[3-(N,N-dimethylamino)-2,2-dimethylpropyl]-4-(1,4-dihydroindeno[1,2-c]pyrazol-3-yl)benzamide,
N-[3-(2-Methylpiperidin-1-yl)propyl]-4-(1,4-dihydroindeno[1,2-c]pyrazol-3-yl)benzamide,
N-(3-Methylbut-2-yl)-4-(1,4-dihydroindeno[1,2-c]pyrazol-3-yl)benzamide,
N-[2-(Pyrrolidin-1-yl)ethyl]-4-(1,4-dihydroindeno[1,2-c]pyrazol-3-yl)benzamide,
N-[3-(N,N-Dimethylamino)prop-2-yl]-4-(1,4-dihydroindeno[1,2-c]pyrazol-3-yl)benzamide, N-(2-Hexyl)-4-(1,4-dihydroindeno[1,2-c]pyrazol-3-yl)benzamide,
N-tert-Butyl-4-(1,4-dihydroindeno[1,2-c]pyrazol-3-yl)benzamide,
N-[7-(N,N-Dimethylamino)heptyl]-4-(1,4-dihydroindeno[1,2-c]pyrazol-3-yl)benzamide,
N-(2-Methylbut-2-yl)-4-(1,4-dihydroindeno[1,2-c]pyrazol-3-yl)benzamide,
N-(2-Pentyl)-4-(1,4-dihydroindeno[1,2-c]pyrazol-3-yl)benzamide,
N-sec-Butyl-4-(1,4-dihydroindeno[1,2-c]pyrazol-3-yl)benzamide,
N-(3,3-Dimethylbutyl)-4-(1,4-dihydroindeno[1,2-c]pyrazol-3-yl)benzamide,
N-(2,2,3,3,3-Pentafluoropropyl)-4-(1,4-dihydroindeno[1,2-c]pyrazol-3-yl)benzamide,
N-(2,5-Dichloropentyl)-4-(1,4-dihydroindeno[1,2-c]pyrazol-3-yl)benzamide,
N-(2,2-Difluoroethyl)-4-(1,4-dihydroindeno[1,2-c]pyrazol-3-yl)benzamide,
N-(2-Chloroethyl)-4-(1,4-dihydroindeno[1,2-c]pyrazol-3-yl)benzamide,
N-[2-(N,N-dimethylamino)propyl]-4-(1,4-dihydroindeno[1,2-c]pyrazol-3-yl)benzamide,
N-(3-Morpholinopropyl)-4-(1,4-dihydroindeno[1,2-c]pyrazol-3-yl)benzamide,
N-[3-(Pyrrolidin-1-yl)propyl]-4-(1,4-dihydroindeno[1,2-c]pyrazol-3-yl)benzamide,
4'-(1,4-Dihydroindeno[1,2-c]pyrazol-3-yl)piperidinoacetanilide,
4'-(1,4-Dihydroindeno[1,2-c]pyrazol-3-yl)-4-methylpiperazin-1-ylacetanilide,
4'-(1,4-Dihydroindeno[1,2-c]pyrazol-3-yl)-4-methylhomopiperazin-1-ylacetanilide,
4'-(1,4-Dihydroindeno[1,2-c]pyrazol-3-yl)piperazin-1-ylacetanilide,
4'-(1,4-Dihydroindeno[1,2-c]pyrazol-3-yl)homopiperazin-1-ylacetanilide,
4'-(1,4-Dihydroindeno[1,2-c]pyrazol-3-yl)dipropylaminoacetanilide,
4'-(1,4-Dihydroindeno[1,2-c]pyrazol-3-yl)dimethylaminoacetanilide,
4'-(1,4-Dihydroindeno[1,2-c]pyrazol-3-yl)fluoroacetanilide,
4'-(1,4-Dihydroindeno[1,2-c]pyrazol-3-yl)-3,5-difluorobenzylanilide,
4'-(1,4-Dihydroindeno[1,2-c]pyrazol-3-yl)-4-fluorobenzylanilide,
4'-(1,4-Dihydroindeno[1,2-c]pyrazol-3-yl)-2-fluorobenzylanilide,
4'-(1,4-Dihydroindeno[1,2-c]pyrazol-3-yl)-3-fluorobenzylanilide,
4'-(1,4-Dihydroindeno[1,2-c]pyrazol-3-yl)-2,4-difluorobenzylanilide,
4'-(1,4-Dihydroindeno[1,2-c]pyrazol-3-yl)-2,5-difluorobenzylanilide,
4'-(1,4-Dihydroindeno[1,2-c]pyrazol-3-yl)-2,3-difluorobenzylanilide,
4'-(1,4-Dihydroindeno[1,2-c]pyrazol-3-yl)-4-nitrobenzylanilide,
4'-(1,4-Dihydroindeno[1,2-c]pyrazol-3-yl)-3-nitrobenzylanilide,
4'-(1,4-Dihydroindeno[1,2-c]pyrazol-3-yl)-3,3,3-trifluoropropananilide,
4'-(1,4-Dihydroindeno[1,2-c]pyrazol-3-yl)isobutananilide,
4'-(1,4-Dihydroindeno[1,2-c]pyrazol-3-yl)isopentananilide,
4'-(1,4-Dihydroindeno[1,2-c]pyrazol-3-yl)-2-methylbutananilide,
4'-(1,4-Dihydroindeno[1,2-c]pyrazol-3-yl)-2-methylpentananilide,
4'-(1,4-Dihydroindeno[1,2-c]pyrazol-3-yl)-2-ethylbutananilide,
4'-(1,4-Dihydroindeno[1,2-c]pyrazol-3-yl)neopentylanilide,
4'-(1,4-Dihydroindeno[1,2-c]pyrazol-3-yl)-4,4-dimethylpentananilide,
4'-(1,4-Dihydroindeno[1,2-c]pyrazol-3-yl)cyclohexananilide,
4'-(1,4-Dihydroindeno[1,2-c]pyrazol-3-yl)trifluoroacetanilide,
4'-(1,4-Dihydroindeno[1,2-c]pyrazol-3-yl)pentafluoropropananilide,
Fluoro-N-(3-Phenyl-1,4-dihydroindeno[1,2-c]pyrazol-6-yl)acetamide,
3,5-Difluoro-N-(3-Phenyl-1,4-dihydroindeno[1,2-c]pyrazol-6-yl)benzylamide,
4-Fluoro-N-(3-Phenyl-1,4-dihydroindeno[1,2-c]pyrazol-6-yl)benzylamide,
2-Fluoro-N-(3-Phenyl-1,4-dihydroindeno[1,2-c]pyrazol-6-yl)benzylamide,
3-Fluoro-N-(3-Phenyl-1,4-dihydroindeno[1,2-c]pyrazol-6-yl)benzylamide,
2,4-Difluoro-N-(3-Phenyl-1,4-dihydroindeno[1,2-c]pyrazol-6-yl)benzylamide,
2,3-Difluoro-N-(3-Phenyl-1,4-dihydroindeno[1,2-c]pyrazol-6-yl)benzylamide,
2,5-Difluoro-N-(3-Phenyl-1,4-dihydroindeno[1,2-c]pyrazol-6-yl)benzylamide,
4-Nitro-N-(3-Phenyl-1,4-dihydroindeno[1,2-c]pyrazol-6-yl)benzylamide,
3-Nitro-N-(3-Phenyl-1,4-dihydroindeno[1,2-c]pyrazol-6-yl)benzylamide,
3,3,3-Trifluoro-N-(3-Phenyl-1,4-dihydroindeno[1,2-c]pyrazol-6-yl)propanamide,
N-(3-Phenyl-1,4-dihydroindeno[1,2-c]pyrazol-6-yl)isobutanamide,
3N-(3-Phenyl-1,4-dihydroindeno[1,2-c]pyrazol-6-yl)isopentanamide,
2-Methyl-N-(3-phenyl-1,4-dihydroindeno[1,2-c]pyrazol-6-yl)butanamide,
2-Methyl-N-(3-phenyl-1,4-dihydroindeno[1,2-c]pyrazol-6-yl)pentanamide,
2-Ethyl-N-(3-phenyl-1,4-dihydroindeno[1,2-c]pyrazol-6-yl)butanamide,
N-(3-Phenyl-1,4-dihydroindeno[1,2-c]pyrazol-6-yl)neopentanamide,
4,4-Dimethyl-N-(3-phenyl-1,4-dihydroindeno[1,2-c]pyrazol-6-yl)pentanamide,
N-(3-Phenyl-1,4-dihydroindeno[1,2-c]pyrazol-6-yl)cyclohexanecarboxamide,
Trifluoro-N-(3-Phenyl-1,4-dihydroindeno[1,2-c]pyrazol-6-yl)acetamide,
Pentafluoro-N-(3-Phenyl-1,4-dihydroindeno[1,2-c]pyrazol-6-yl)propanamide,
4'-(1,4-Dihydroindeno[1,2-c]pyrazol-3-yl)acetanilide,
2-Hydroxy-N-(2-morpholinoethyl)-5-(1,4-dihydroindeno[1,2-c]pyrazol-3-yl)benzamide,
2-Hydroxy-N-(2-morpholinopropyl)-4-(1,4-dihydroindeno[1,2-c]pyrazol-3-yl)benzamide,
2-Hydroxy-N-[2-(pyrrolidin-1-yl)ethyl]-5-(1,4-dihydroindeno[1,2-c]pyrazol-3-yl)benzamide,
2-Hydroxy-N-[3-(pyrrolidin-1-yl)propyl]-5-(1,4-dihydroindeno[1,2-c]pyrazol-3-yl)benzamide,
N-[2-(N,N-Diethylamino)ethyl]-5-(1,4-dihydroindeno[1,2-c]pyrazol-3-yl)-2-hydroxybenzamide,
N-[3-(N,N-Diethylamino)propyl]-5-(1,4-dihydroindeno[1,2-c]pyrazol-3-yl)-2-hydroxybenzamide, 2-Hydroxy-N-[2-(N,N-dimethylamino)ethyl]-5-(1,4-dihydroindeno[1,2-c]pyrazol-3-yl)benzamide,
2-Hydroxy-N-[3-(N,N-dimethylamino)propyl]-5-(1,4-dihydroindeno[1,2-c]pyrazol-3-yl)benzamide,
2-Hydroxy-N-[2-(N,N-dipropylamino)ethyl]-5-(1,4-dihydroindeno[1,2-c]pyrazol-3-yl)benzamide,
2-Hydroxy-N-[2-(N,N-di-isopropylamino)ethyl]-5-(1,4-dihydroindeno[1,2-c]pyrazol-3-yl)benzamide,
2-Hydroxy-N-[3-(N,N-dipropylamino)propyl]-5-(1,4-dihydroindeno[1,2-c]pyrazol-3-yl)benzamide,
2-Hydroxy-N-[3-(N,N-di-isopropylamino)propyl]-5-(1,4-dihydroindeno[1,2-c]pyrazol-3-yl)benzamide,
2-Hydroxy-N-(2-piperidinoethyl)-5-(1,4-dihydroindeno[1,2-c]pyrazol-3-yl)benzamide,
2-Hydroxy-N-(2-piperidinopropyl)-5-(1,4-dihydroindeno[1,2-c]pyrazol-3-yl)benzamide,
2-Hydroxy-N-[2-(piperazin-1-yl)ethyl]-5-(1,4-dihydroindeno[1,2-c]pyrazol-3-yl)benzamide,
2-Hydroxy-N-[3-(piperazin-1-yl)propyl]-5-(1,4-dihydroindeno[1,2-c]pyrazol-3-yl)benzamide,
2-Hydroxy-N-[2-(4-methylpiperazin-1-yl)ethyl]-5-(1,4-dihydroindeno[1,2-c]pyrazol-3-yl)benzamide,
2-Hydroxy-N-[3-(4-methylpiperazin-1-yl)propyl]-5-(1,4-dihydroindeno[1,2-c]pyrazol-3-yl)benzamide,
2-Hydroxy-N-[2-(thiomorpholin-1-yl)ethyl]-5-(1,4-dihydroindeno[1,2-c]pyrazol-3-yl)benzamide,
2-Hydroxy-N-[3-(thiomorpholin-1-yl)propyl]-5-(1,4-dihydroindeno[1,2-c]pyrazol-3-yl)benzamide,
2-Hydroxy-N-[2-(Homopiperazin-1-yl)ethyl]-5-(1,4-dihydroindeno[1,2-c]pyrazol-3-yl)benzamide,
2-Hydroxy-N-[3-(Homopiperazin-1-yl)propyl]-5-(1,4-dihydroindeno[1,2-c]pyrazol-3-yl)benzamide,
2-Hydroxy-N-[2-(Perhydroazepin-1-yl)ethyl]-5-(1,4-dihydroindeno[1,2-c]pyrazol-3-yl)benzamide,
2-Hydroxy-N-[3-(Perhydroazepin-1-yl)propyl]-5-(1,4-dihydroindeno[1,2-c]pyrazol-3-yl)benzamide,
4-(1,4-Dihydroindeno[1,2-c]pyrazol-3-yl)-N-(2-morphilinoethyl)aniline,
4-(1,4-Dihydroindeno[1,2-c]pyrazol-3-yl)-N-(2-morphilinopropyl)aniline,
4-(1,4-Dihydroindeno[1,2-c]pyrazol-3-yl)-N-(2-piperidinoethyl)aniline,
4-(1,4-Dihydroindeno[1,2-c]pyrazol-3-yl)-N-(2-piperidinopropyl)aniline,
4-(1,4-Dihydroindeno[1,2-c]pyrazol-3-yl)-N-[2-(thiomorphilin-yl)ethyl]aniline,
4-(1,4-Dihydroindeno[1,2-c]pyrazol-3-yl)-N-[2-(thiomorphilinl-yl)propyl]aniline,
4-(1,4-Dihydroindeno[1,2-c]pyrazol-3-yl)-N-[2-(piperazin-1-yl)ethyl]aniline,
4-(1,4-Dihydroindeno[1,2-c]pyrazol-3-yl)-N-[2-(piperazin-1-yl)propyl]aniline,
4-(1,4-Dihydroindeno[1,2-c]pyrazol-3-yl)-N-[2-(4-methylpiperazin-1-yl)ethyl]aniline,
4-(1,4-Dihydroindeno[1,2-c]pyrazol-3-yl)-N-[2-(4-methylpiperazin-1-yl)propyl]aniline,
N-[2-(N,N-Diethylamino)ethyl]-4-(1,4-Dihydroindeno[1,2-c]pyrazol-3-yl)aniline,
N-[3-(N,N-Diethylamino)propyl]-4-(1,4-Dihydroindeno[1,2-c]pyrazol-3-yl)aniline,
4-(1,4-Dihydroindeno[1,2-c]pyrazol-3-yl)-N-[2-(N,N-dipropylamino)ethyl]aniline,
4-(1,4-Dihydroindeno[1,2-c]pyrazol-3-yl)-N-[3-(N,N-dipropylamino)propyl]aniline,
4-(1,4-Dihydroindeno[1,2-c]pyrazol-3-yl)-N-[2-(N,N-dimethyllamino)ethyl]aniline,
4-(1,4-Dihydroindeno[1,2-c]pyrazol-3-yl)-N-[3-(N,N-dimethylamino)propyl]aniline,
Methyl 4-(6-Acetamido-1,4-Dihydroindeno[1,2-c]pyrazol-3-yl)benzoate,
N-(3-Methoxypropyl)-4-(1,4-dihydroindeno[1,2-c]pyrazol-3-yl)benzamide,
4-(1,4-Dihydroindeno[1,2-c]pyrazol-3-yl)-N-(4-Nitrophenyl)benzamide,
N-(3-Phenyl-1,4-dihydroindeno[1,2-c]pyrazol-6-yl)morpholinoacetamide,
N-(3-Phenyl-1,4-dihydroindeno[1,2-c]pyrazol-6-yl)morpholinoacetamide,
N-(3-Phenyl-1,4-dihydroindeno[1,2-c]pyrazol-6-yl)piperidinoacetamide,
N-(3-Phenyl-1,4-dihydroindeno[1,2-c]pyrazol-6-yl)thiomorpholinoacetamide,
N-(3-Phenyl-1,4-dihydroindeno[1,2-c]pyrazol-6-yl)-4-methylpiperazin-1-ylacetamide,
N-(3-Phenyl-1,4-dihydroindeno[1,2-c]pyrazol-6-yl)piperazin-1-ylacetamide,
N-(3-Phenyl-1,4-dihydroindeno[1,2-c]pyrazol-6-yl)pyrrolidin-1-ylacetamide,
2-(N,N-Diethylamino)-N-(3-phenyl-1,4-dihydroindeno[1,2-c]pyrazol-6-yl)acetamide,
N-(3-Phenyl-1,4-dihydroindeno[1,2-c]pyrazol-6-yl)-2-(dimethylamino)acetamide,
N-(3-Phenyl-1,4-dihydroindeno[1,2-c]pyrazol-6-yl)-2-(dipropylamino)acetamide,
4-(6-Amino-1,4-dihydroindeno[1,2-c]pyrazol-3-yl)-N-[2-(N,N-diethylamino)ethyl]-benzamide,
3-[3-(2-Morpholinoethoxy)phenyl]-1,4-dihydroindeno[1,2c]pyrazole,
3-[3-(2-Morpholinoethoxy)phenyl]-1,4-dihydroindeno[1,2c]pyrazole,
3-[3-(3-Morpholinopropoxy)phenyl]-1,4-dihydroindeno[1,2c]pyrazole,
3-[3-(2-Piperidinoethoxy)phenyl]-1,4-dihydroindeno[1,2c]pyrazole,
3-[3-(3-Piperidinopropoxy)phenyl]-1,4-dihydroindeno[1,2c]pyrazole,
3-{3-[2-(Piperazin-1-yl)ethoxy]phenyl}-1,4-dihydroindeno[1,2c]pyrazole,
3-{3-[3-(Piperazin-1-yl)propoxy]phenyl}-1,4-dihydroindeno[1,2c]pyrazole,
3-{3-[2-(4-Methylpiperazin-1-yl)ethoxy]phenyl}-1,4-dihydroindeno[1,2c]pyrazole,
3-{3-[3-(4-Methylpiperazin-1-yl)propoxy]phenyl}-1,4-dihydroindeno[1,2c]pyrazole,
3-{3-[2-(Homopiperazin-1-yl)ethoxy]phenyl}-1,4-dihydroindeno[1,2c]pyrazole,
3-{3-[3-(Homopiperazin-1-yl)propoxy]phenyl}-1,4-dihydroindeno[1,2c]pyrazole,
3-{3-[2-(4-Methylhomopiperazin-1-yl)ethoxy]phenyl}-1,4-dihydroindeno[1,2c]pyrazole,
3-{3-[3-(4-Methylhomopiperazin-1-yl)propoxy]phenyl}-1,4-dihydroindeno[1,2c]pyrazole,
3-{3-[2-(N,N-Diethylamino)ethoxy]phenyl}-1,4-dihydroindeno[1,2c]pyrazole,
3-{3-[3-(N,N-Diethylamino)propoxy]phenyl}-1,4-dihydroindeno[1,2c]pyrazole,
3-{3-[2-(N,N-Dimethylamino)ethoxy]phenyl}-1,4-dihydroindeno[1,2c]pyrazole,
3-{3-[3-(N,N-Dimethylamino)propoxy]phenyl}-1,4-dihydroindeno[1,2c]pyrazole,
3-{3-[2-(N,N-Dipropylamino)ethoxy]phenyl}-1,4-dihydroindeno[1,2c]pyrazole, and
3-{3-[3-(N,N-Dipropylamino)propoxy]phenyl}-1,4-dihydroindeno[1,2c]pyrazole
Dihydroxy 4-(4H-indeno-[1,2-c]-pyrazol-3-yl)phenylborane 4-(1H-[1]Benzothieno[3,2-c]pyrazol-3-yl)benzaldehyde
4-(1H-[1]Benzothieno[3,2-c]pyrazol-3-yl)-N-[3-(imidazol-1-yl)propyl]benzylamine trihydrochloride
Methyl 4-(4-oxo-1,4-dihydroindeno[1,2-c]pyrazol-3-yl)benzoate
4-(1,4-dihydroindeno[1,2-c]pyrazol-3-yl)benzamide oxime
3-{4-[(2-diethylaminoethyl)aminomethyl]phenyl)}-1,4-dihydroindeno[1,2-c]pyrazole trihydrochloride
N-[4-(1,4-Dihydroindeno[1,2-c]pyrazol-3-yl)phenyl]benzenesulphonamide
N-(2-Morpholinoethyl)-4'-dihydroindeno[1,2-c]pyrazol-3-ylaniline dihydrochloride
N-(1,4-Dihydroindeno[1,2-c]pyrazol-6-yl)-2-morpholinoacetamide
N-(2-Morpholinoethyl)-3-phenyl-1,4-dihydroindeno[1,2-c]pyrazol-6-ylamine trihydrochloride
4'-(1-Acetyl-1,4-dihydroindeno[1,2-c]pyrazol-3-yl)acetanilide
3-[4-(2-morpholinoethoxy)phenyl]-1,4-dihydroindeno[1,2-c]pyrazole
3-[2-(2H-1,2,3,4-Tetraazol-5-yl)-4-pyridyl]-4,5-dihydro-2H-benzo[g]indazole
3-(4-Isocyanatophenyl)-1,4-dihydroindeno[1,2-c]pyrazole,
2-(Diethylamino)ethyl N-[4-(1,4-dihydroindeno[1,2-c]pyrazol-3-l)phenyl]carbamate
2-Morpholinoethyl N-[4-(1,4-dihydroindeno[1,2-c]pyrazol-3-yl)phenyl]carbamate
3-(Dibenzylamino)propyl N-[4-(1,4-dihydroindeno[1,2-c]pyrazol-3-yl)phenyl]carbamate
2-[Ethyl(2-hydroxyethyl)amino]ethyl N-[4-(1,4-dihydroindeno[1,2-c]pyrazol-3-yl)phenyl]carbamate
2-[[2-(Dimethylamino)ethyl](methyl)amino]ethyl N-[4-(1,4-dihydroindeno[1,2-c]pyrazol-3-yl)phenyl]carbamate
1-Methyl-2-propoxyethyl N-[4-(1,4-dihydroindeno[1,2-c]pyrazol-3-yl)phenyl]carbamate
2-(1-Methyltetrahydro-1H-2-pyrrolyl)ethyl N-[4-(1,4-dihydroindeno[1,2-c]pyrazol-3-yl)phenyl]carbamate
2-[2-(Dimethylamino)ethoxy]ethyl N-[4-(1,4-dihydroindeno[1,2-c]pyrazol-3-yl)phenyl]carbamate
2-(Diethylamino)-1-methylethyl N-[4-(1,4-dihydroindeno[1,2-c]pyrazol-3-yl)phenyl]carbamate
N-[2-(Diethylamino)ethyl]-N'-[4-(1,4-dihydroindeno[1,2-c]pyrazol-3-yl)phenyl]urea
N-[4-(1,4-Dihydroindeno[1,2-c]pyrazol-3-yl)phenyl]-N'-(2-morpholinoethyl)urea
N1-[4-(1,4-Dihydroindeno[1,2-c]pyrazol-3-yl)phenyl]-1-piperidinecarboxamide
N-[4-(1,4-Dihydroindeno[1,2-c]pyrazol-3-yl)phenyl]-N'-[2-(dimethylamino)-1-methylethyl]urea
N-[4-(1,4-Dihydroindeno[1,2-c]pyrazol-3-yl)phenyl]-N-tetrahydro-2-furanylmethylurea
N-[4-(1,4-Dihydroindeno[1,2-c]pyrazol-3-yl)phenyl]-N'-(2-furylmethyl)urea
N-(1,3-Benzodioxol-5-ylmethyl)-N'-[4-(1,4-dihydroindeno[1,2-c]pyrazol-3-yl)phenyl]urea
N-Cyclobutyl-N'-[4-(1,4-dihydroindeno[1,2-c]pyrazol-3-yl)phenyl]
N-[4-(1,4-Dihydroindeno[1,2-c]pyrazol-3-yl)phenyl]-N'-(2-piperidinoethyl)urea urea
N-Benzyl-N'-[4-(1,4-dihydroindeno[1,2-c]pyrazol-3-yl)phenyl]urea
N-[4-(Diethylamino)butyl]-N'-[4-(1,4-dihydroindeno[1,2-c]pyrazol-3-yl)phenyl]urea
N-[4-(1,4-Dihydroindeno[1,2-c]pyrazol-3-yl)phenyl]-N'-[2-(2-thienyl)ethyl]urea
N-[3-(Diethylamino)propyl]-N'-[4-(1,4-dihydroindeno[1,2-c]pyrazol-3-yl)phenyl]urea
N-[4-(1,4-Dihydroindeno[1,2-c]pyrazol-3-yl)phenyl]-N-[(1-ethyltetrahydro-1H-2-pyrrolyl)methyl]urea
N-(2,5-Difluorobenzyl)-N'-[4-(1,4-dihydroindeno[1,2-c]pyrazol-3-yl)phenyl]urea
N-[4-(1,4-Dihydroindeno[1,2-c]pyrazol-3-yl)phenyl]-N'-[2-(2-hydroxyethoxy)ethyl]urea
N-[4-(1,4-Dihydroindeno[1,2-c]pyrazol-3-yl)phenyl]-N'-[2-hydroxy-1-(hydroxymethyl)ethyl]urea
N-[4-(1,4-Dihydroindeno[1,2-c]pyrazol-3-yl)phenyl]-N'-(2,3-dihydroxypropyl)urea
N1-[4-(1,4-Dihydroindeno[1,2-c]pyrazol-3-yl)phenyl]-4-(2-pyridyl)-1-piperazinecarboxamide
N'-[4-(1,4-Dihydroindeno[1,2-c]pyrazol-3-yl)phenyl]-N-[3-(dimethylamino)propyl]-N-methylurea
N1-[4-(1,4-Dihydroindeno[1,2-c]pyrazol-3-yl)phenyl]-1-azetanecarboxamide
N1-[4-(1,4-Dihydroindeno[1,2-c]pyrazol-3-yl)phenyl]-4-(4-fluorophenyl)-1-piperazinecarboxamide
N-Benzyl-N'-[4-(1,4-dihydroindeno[1,2-c]pyrazol-3-yl)phenyl]-N-methylurea
N'-[4-(1,4-Dihydroindeno[1,2-c]pyrazol-3-yl)phenyl]-N-ethyl-N-(2-hydroxyethyl)urea
N1-[4-(1,4-Dihydroindeno[1,2-c]pyrazol-3-yl)phenyl]-4-(2-methoxyphenyl)-1-piperazinecarboxamide
N'-[4-(1,4-Dihydroindeno[1,2-c]pyrazol-3-yl)phenyl]-N-[2-(dimethylamino)ethyl]-N-methylurea
N1-[4-(1,4-Dihydroindeno[1,2-c]pyrazol-3-yl)phenyl]-4-methyl-1-piperazinecarboxamide
N1-[4-(1,4-Dihydroindeno[1,2-c]pyrazol-3-yl)phenyl]-4-(4-hydroxyphenyl)-1-piperazinecarboxamide
N1-[4-(1,4-Dihydroindeno[1,2-c]pyrazol-3-yl)phenyl]-4-[(E)-3-phenyl-2-propenyl]-1-piperazinecarboxamide
N1-[4-(1,4-Dihydroindeno[1,2-c]pyrazol-3-yl)phenyl]-4-phenyl-1-piperazinecarboxamide
N'-[4-(1,4-Dihydroindeno[1,2-c]pyrazol-3-yl)phenyl]-N,N-di(2-methoxyethyl)urea
N'-[4-(1,4-Dihydroindeno[1,2-c]pyrazol-3-yl)phenyl]-N-(2,3-dihydroxypropyl)-N-methylurea
N,N-di[2-(Diethylamino)ethyl]-N'-[4-(1,4-dihydroindeno[1,2-c]pyrazol-3-yl)phenyl]urea
N-[4-(1,4-Dihydroindeno[1,2-c]pyrazol-3-yl)phenyl]-N'-(2-pyridylmethyl)urea
N-[4-(1,4-Dihydroindeno[1,2-c]pyrazol-3-yl)phenyl]-N'-(3-pyridylmethyl)urea
N-[4-(1,4-Dihydroindeno[1,2-c]pyrazol-3-yl)phenyl]-N'-(4-pyridylmethyl)urea
N-[4-(1,4-Dihydroindeno[1,2-c]pyrazol-3-yl)phenyl]-N'-(2-hydroxyethyl)urea
N-[4-(1,4-Dihydroindeno[1,2-c]pyrazol-3-yl)phenyl]-N'-[7-(dimethylamino)heptyl]urea and pharmaceutically acceptable salts thereof and tautomers thereof.

Another specific compound of the present invention is represented by the following structural formula:

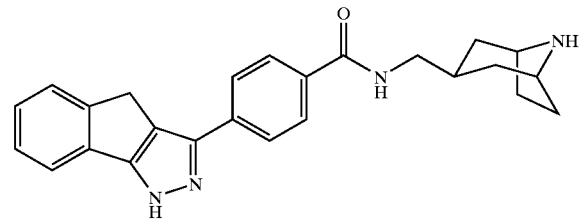

Additional specific compounds of formula I as represented by formula are shown in the Tables below. Pharmaceutically acceptable salts and tautomers of these compounds are also included in the present invention.

TABLE 1

X = (CH$_2$)$_n$

| Ring A substituent | n | R$_1$ |
|---|---|---|
| H | 1 | |
| H | 1 | 2-S-(2-pyridyl), 5-NO$_2$ |
| H | 1 | 3-NO$_2$ |
| 6,7-(OMe)$_2$ | 1 | 3-OPh |
| H | 1 | 4-SMe |
| H | 1 | 4-O-(2-pyridyl)-5-CF$_3$ |
| H | 1 | 3-OH, 4-OMe |
| H | 1 | 4-OH, 3-OMe |
| H | 1 | 2-OH |
| 6,7-(OMe)$_2$ | 1 | 4-NMe$_2$ |
| H | 1 | 3,4-dimethylphenyl |
| 6,7,8-(OMe)$_3$ | 1 | 2,3,4-(OMe)$_3$ |
| H | 1 | 4-OCHF$_2$ |
| H | 1 | 4-OH, 3,5-(But)$_2$ |
| H | 2 | 4-NHAc |
| H | 2 | 4-OCH$_2$CH=CH$_2$ |
| H | 2 | 4-NEt$_2$ |
| H | 2 | 4-NO$_2$ |
| H | 2 | 4-OCH$_2$Ph |
| H | 2 | 4-CN |
| H | 2 | 2-Cl, 5-NO$_2$ |

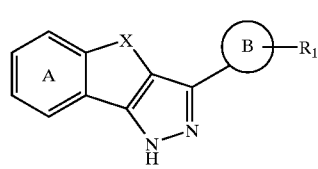

TABLE 2

X = (CH$_2$)$_n$

| Ring A Substituents | n | B with R$_1$ |
|---|---|---|
| 6-AcNH | 1 | 2-methylfuran |
| H | 1 | 5-methyl-2-(3,5-bis-CF$_3$-phenyl)furan |
| H | 1 | 5-methyl-3-bromothiophene |
| 7-OMe | 2 | 2,5-dimethylfuran |
| H | 2 | 2,5-dimethylfuran |

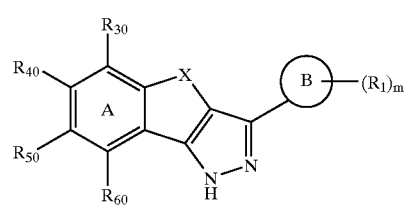

TABLE 3

| Ring A Substituents | X | B with R$_1$ |
|---|---|---|
| H | C=O | 5-methyl-2-(2-nitro-4-CF$_3$-phenyl)furan |

TABLE 4

| B with R₁ | x | Ring A Substituents |
|---|---|---|
| 4-(Ph)PHENYL | $CH_2$ | H |
| 4-(OPh)PHENYL | $CH_2$ | H |
| 4-($SO_2$Me)PHENYL | $(CH_2)_2$ | $R_{40}$ = MeO |
| 3-($CO_2$H), 4-(OH)PHENYL | $CH_2$ | H |
| 3-($NO_2$), 4-(OH)PHENYL | $CH_2$ | H |
| 3-($OCH_2CONH_2$)PHENYL | $CH_2$ | H |
| 4-($OCH_2$Ph)PHENYL | $CH_2$ | $R_{40}, R_{50}$ = $(MeO)_2$ |
| 4-($OCH_2$Ph)PHENYL | $CH_2$ | $R_{50}$ = MeO |
| 4-(OH)PHENYL | $CH_2$ | $R_{40}, R_{50}$ = $(MeO)_2$ |
| 3-($CONH(CH_2)_2$MOR), 4-(OH))PHENYL | $CH_2$ | H |
| 3-($CONH(CH_2)_2NEt_2$), 4-(OH)PHENYL | $CH_2$ | H |
| 4-(Br)PHENYL | $CH_2$ | H |
| 4-(OH)PHENYL | $CH_2$ | $R_{40}$ = MeO |
| 4-($CONH(CH_2)_3NEt_2$)PHENYL | $CH_2$ | H |
| 4-($CONH(CH_2)_2$OMe)PHENYL | $CH_2$ | H |
| 4-($CONH(4-NO_2$Ph))PHENYL | $CH_2$ | H |
| 4-(OH)PHENYL | $CH_2$ | $R_{50}$ = MeO |
| 4-($CONH(CH_2)_2NEt_2$)PHENYL | $CH_2$ | $R_{40}$ = $NH_2$ |
| 4-(Br)PHENYL | S | H |
| 4-(OH)PHENYL | $CH_2$ | $R_{30}$ = $O(CH_2)_2$OMe |
| 4-($SO_2NH(CH_2)_2$MOR)PHENYL | $CH_2$ | H |
| 4-($SO_2NH(CH_2)_2$OMe)PHENYL | $CH_2$ | H |
| 3-($CH_2NMe_2$), 4-(OH)PHENYL | $CH_2$ | H |
| 4-(OH)PHENYL | $CH_2$ | $R_{30}$ = $O(CH_2)_2$MOR |
| 4-($SO_2NH(CH_2)_2NEt_2$)PHENYL | $CH_2$ | H |
| 4-($OCH_2CONH_2$)PHENYL | $CH_2$ | $R_{30}$ = $O(CH_2)_2$OMe |
| 4-(OH)PHENYL | $CH_2$ | $R_{40}$ = (OH), $R_{50}$ = $(O(CH_2)_2$OMe) |
| 4-(OH)PHENYL | $CH_2$ | $R_{40}$ = $(O(CH_2)_2$OMe) |
| 4-($CONH(CH_2)_2$NHEt)PHENYL | $CH_2$ | H |
| 4-($CONHCH_2$-2-PYRR)PHENYL | $CH_2$ | H |
| 4-($OCH_2CONH_2$)PHENYL | $CH_2$ | $R_{30}$ = OH |
| 4-($OCH_2CO_2$H)PHENYL | $CH_2$ | H |

Structure: A benzofused ring A with X linker to a pyrazole bearing NH, connected to phenyl ring B with CH₂-NRR' substituent.

TABLE 5

| X | NRR' |
|---|---|
| $CH_2$ | NH n-$C_{12}H_{25}$ |
| $CH_2$ | HN-$CH_2CH_2$-OMe |
| $CH_2$ | HN-$CH_2$-CH=$CH_2$ (allyl) |
| $CH_2$ | HN-$CH_2$-C≡CH (propargyl) |
| $CH_2$ | HN-cyclohexyl |
| $CH_2$ | HN-$CH_2CH_2$-N(piperidinyl) |
| $CH_2$ | HN-$CH_2CH_2$-(cyclohexenyl) |
| $CH_2$ | HN-(tetrazol-5-yl) |
| $CH_2$ | HN-(pyrazin-2-yl) |
| $CH_2$ | HN-(imidazol-2-yl) |
| $CH_2$ | HN-$CH_2$-(pyridin-2-yl) |
| $CH_2$ | HN-$CH_2$-(pyridin-3-yl) |
| O | HN-$CH_2CH_2$-OMe |
| O | N-(4-methylpiperazin-1-yl) |
| O | HN-(pyridin-2-yl) |
| O | HN-(pyridin-3-yl) |
| O | HN-($C_6H_4$)-$NMe_2$ (4-dimethylaminophenyl) |
| O | HN-(1,2,4-triazol-3-yl) (HCl) |

TABLE 5-continued

| X | NRR' |
|---|---|
| O | HN—(1H-tetrazol-5-yl) |
| O | HN—CH2—(pyridin-4-yl) |
| S | HN—CH2CH2—(morpholin-4-yl) |
| S | HN—CH2CH2—NMe2 |
| S | HN—(pyridin-2-yl) |
| S | HN—(pyridin-3-yl) |
| S | HN—(pyridin-4-yl) |
| S | HN—CH2—(pyridin-4-yl) |
| CH2 | NH iso-Pr |
| CH2 | NH cyc-P |
| CH2 | NH n-Hex |
| CH2 | HN—CH2—(piperidin-4-yl) |
| CH2 | piperidin-1-yl |
| CH2 | 4-methylpiperazin-1-yl |
| CH2 | morpholin-4-yl |
| CH2 | HN—(4-methoxyphenyl) |
| CH2 | HN—(4-hydroxyphenyl) |
| CH2 | HN—(pyridin-2-yl) |
| CH2 | HN—(pyridin-3-yl) |
| CH2 | HN—CH2—(pyridin-4-yl) |
| CH2 | HN—(1H-1,2,4-triazol-3-yl) |
| CH2 | HN—(thiazol-2-yl) |
| O | piperidin-1-yl |
| O | HN—(pyridin-4-yl) |
| O | HN—CH2CH2—NMe2 |
| O | HN—CH2CH2—(morpholin-4-yl) (2HCL) |

TABLE 6

| X | NRR' |
|---|---|
| CH2 | HN—CH2CH2—(morpholin-4-yl) (2HCl) |
| CH2 | piperidin-1-yl |
| CH2 | 4-methylpiperazin-1-yl |

TABLE 6-continued

| X | NRR' |
|---|---|
| CH₂ | 2-pyridyl-NH- |
| CH₂ | 3-pyridyl-NH- |
| CH₂ | (2-pyridyl)CH₂-NH- |

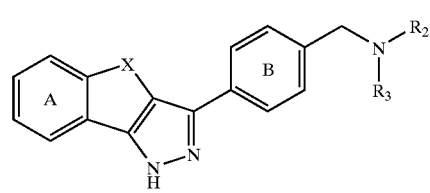

TABLE 7

| Entry | X | NR₂R₃ |
|---|---|---|
| 1 | CH₂ | piperazine |
| 2 | CH₂ | 4-ethylpiperazine |
| 3 | CH₂ | 4-(ethoxycarbonyl)piperazine (2HCl) |
| 4 | CH₂ | 4-(2-(dimethylamino)ethyl)piperazine |
| 5 | CH₂ | homopiperazine |
| 6 | CH₂ | 1-acetyl-4-aminopiperidine |
| 7 | CH₂ | 1-(ethoxycarbonyl)-4-aminopiperidine (2HCl) |
| 8 | CH₂ | 1-(N,N-dimethylglycyl)-4-aminopiperidine |
| 9 | CH₂ | 1-(2-(dimethylamino)ethyl)-4-aminopiperidine |
| 10 | CH₂ | (1-methylpiperidin-4-yl)methylamine |
| 11 | CH₂ | N-methyl-(1-methylpiperidin-4-yl)methylamine |
| 12 | CH₂ | 1-amino-4-methylpiperazine |
| 13 | CH₂ | 5-amino-2-(N-methyl-N-(2-(dimethylamino)ethyl)amino)pyridine |
| 14 | CH₂ | 3-amino-8-methyl-8-azabicyclo[3.2.1]octane (exo) |
| 15 | S | piperazine |
| 16 | S | 4-ethylpiperazine |
| 17 | S | 4-(ethoxycarbonyl)piperazine |
| 18 | S | 4-(2-(dimethylamino)ethyl)piperazine |
| 19 | S | 4-aminopiperidine |
| 20 | S | 1-acetyl-4-aminopiperidine |

TABLE 7-continued
| Entry | X | NR₂R₃ |
|---|---|---|
| 21 | S | 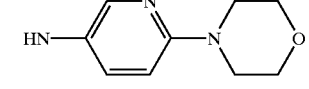 |
| 22 | S | 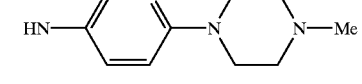 |
| 23 | S | 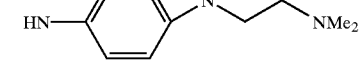 |
| 24 | S | 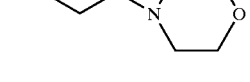 |
| 25 | S |  |
| 26 | S | 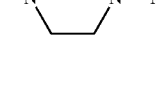 |
| 27 | S | 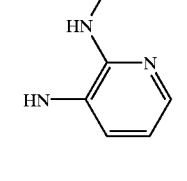 |
| 28 | S | 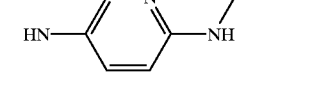 |
| 29 | S | 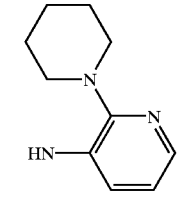 |
| 30 | S | 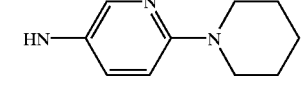 |
| 31 | S | 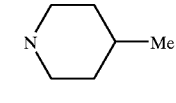 |
| 32 | S |  |
| 33 | S |  |
| 34 | S |  |
| 35 | S |  |
| 36 | S |  |
| 37 | S |  |
| 38 | S |  |
| 39 | CH₂ |  |
| 40 | CH₂ |  |
| 41 | CH₂ |  |
| 42 | CH₂ |  |
| 43 | CH₂ |  |
| 44 | CH₂ |  |
| 45 | CH₂ |  |
| 46 | CH₂ | NMe₂(2HCl) |
| 47 | CH₂ |  (2HCl) |

TABLE 7-continued
| Entry | X | NR₂R₃ |
|---|---|---|
| 48 | CH₂ | 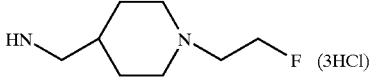 (3HCl) |
| 49 | S | 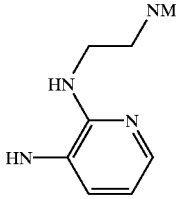 |
| 50 | S | 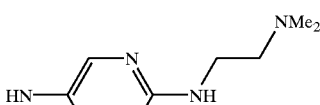 |
| 51 | S | 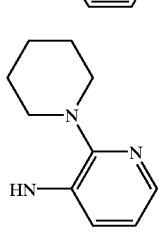 |
| 52 | S | 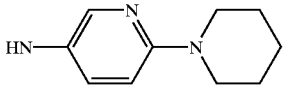 |
| 53 | S | 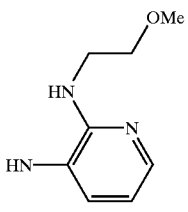 |
| 54 | S |  |
| 55 | S | NMe₂ |
| 56 | S | 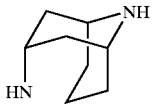 |
| 57 | S | 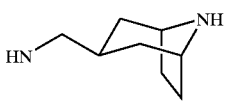 |
| 58 | CO | 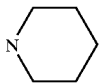 |
| 59 | CH₂ | NH₂ |
| 60 | CH₂ | 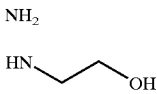 |
TABLE 7-continued
| Entry | X | NR₂R₃ |
|---|---|---|
| 61 | CH₂ | 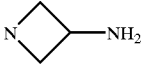 |
| 62 | CH₂ |  |
| 63 | CH₂ | 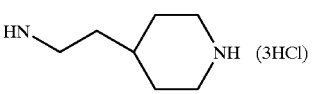 (3HCl) |
| 64 | CH₂ | 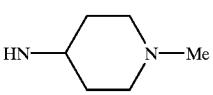 |
| 65 | CH₂ | 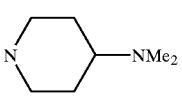 |
| 66 | CH₂ | 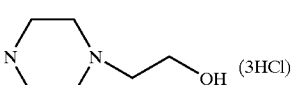 (3HCl) |
| 67 | CH₂ | 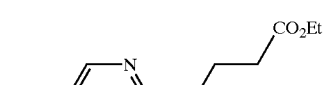 |
| 68 | CH₂ | 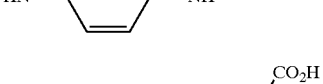 |
| 69 | CH₂ | 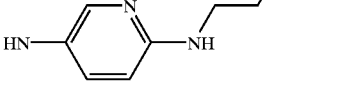 |
| 70 | CH₂ | 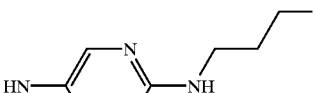 |
| 71 | CH₂ |  |
| 72 | S | 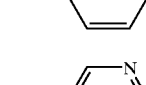 |
| 73 | S | 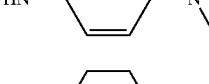 |
| 74 | S | 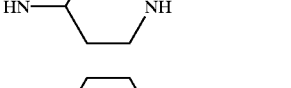 (2HCl) |

TABLE 7-continued
| Entry | X | NR₂R₃ |
|---|---|---|
| 75 | S | 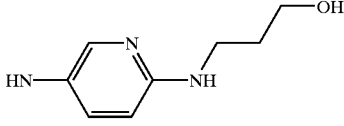 |
| 76 | S | 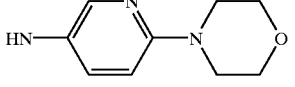 |
| 77 | S | 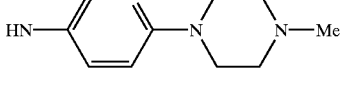 |
| 78 | S | 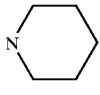 |
| 79 | CMe₂ | NMe₂ |
| 80 | CMe₂ | 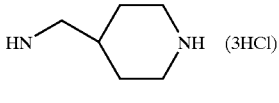 |
| 81 | SO₂ | 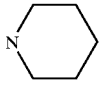 (3HCl) |
| 82 | SO₂ | 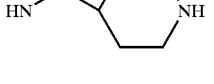 |
| 83 | S | 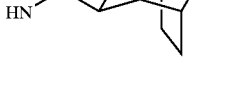 |
| 84 | CH₂ | 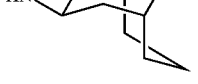 |
| 85 | S | 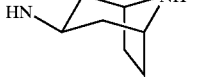 |
| 86 | S | 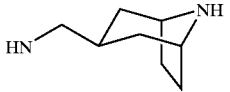 |
| 87 | S | 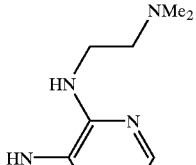 |
TABLE 7-continued
| Entry | X | NR₂R₃ |
|---|---|---|
| 88 | S | 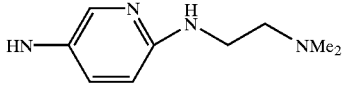 |
| 89 | S | 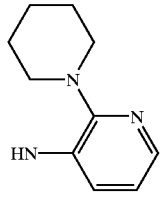 |
| 90 | S | 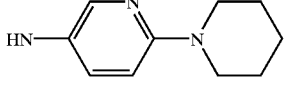 |
| 91 | S | 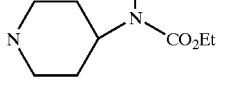 |
| 92 | CH₂ | 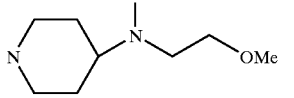 |
| 93 | CH₂ | 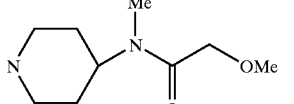 |
| 94 | CH₂ | 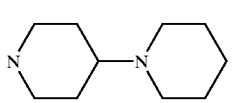 |
| 95 | CH₂ | 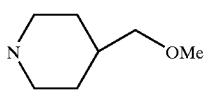 |
| 96 | CH₂ | 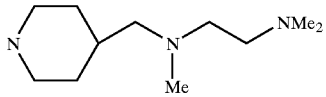 |
| 97 | CH₂ | 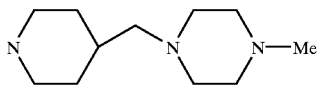 |
| 98 | CH₂ |  |

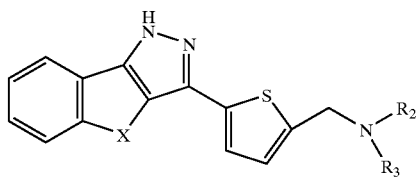

TABLE 7-continued

| Entry | X | NR₂R₃ |
|---|---|---|
| 99 | CH₂ | N(Me)-(4-piperidinyl-NH) (3HCl) |
| 100 | CH₂ | N-(4-piperidinyl-NH)-Ac (2HCl) |
| 101 | CH₂ | N-(1-Me-piperidin-4-yl)-Ac |
| 102 | CH₂ | N(Me)-CH₂-(piperidin-4-yl)NH (3HCl) |
| 103 | CH₂ | N(Ac)-CH₂-(1-Me-piperidin-4-yl) |
| 104 | CH₂ | HN-CH₂CH₂CH₂-(1-Me-piperidin-4-yl) |
| 105 | S | (piperidin-4-yl)-N(Me)-CO₂Et (HCl) |
| 106 | S | (piperidin-4-yl)-N(Me)-CH₂CH₂OMe |
| 107 | S | (piperidin-4-yl)-N(Me)-C(O)CH₂OMe |
| 108 | S | 1,4'-bipiperidinyl |
| 109 | S | 4-(CH₂OMe)-piperidin-1-yl |
| 110 | S | 4-((4-Me-piperazin-1-yl)methyl)-piperidin-1-yl |
| 111 | S | N(Me)-CH₂-(piperidin-4-yl)NH |

TABLE 8

| Entry | X | NR₂R₃ |
|---|---|---|
| 1 | CH₂ | HN-(pyridin-4-yl) |
| 2 | CH₂ | HN-(1H-imidazol-2-yl) |
| 3 | CH₂ | NMe₂ |
| 4 | CH₂ | piperidin-1-yl |
| 5 | CH₂ | 4-Me-piperazin-1-yl |
| 6 | S | HN-(pyridin-4-yl) |
| 7 | S | NMe₂ |
| 8 | S | HN-CH₂CH₂-NMe₂ |
| 9 | S | HN-(1-Me-piperidin-4-yl) |
| 10 | S | HN-CH₂-(piperidin-4-yl)NH |
| 11 | S | piperidin-1-yl |

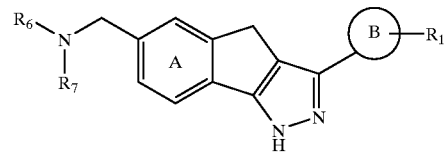

TABLE 9

| Entry | R<sub>8</sub> | NR$_6$R$_7$ |
|---|---|---|
| 1 | H | piperidine |
| 2 | H | 4-methylpiperazine |
| 3 | H | 4-aminopiperidine |
| 4 | H | 1-methyl-4-aminopiperidine |
| 5 | H | 4-(dimethylamino)piperidine |
| 6 | H | 4-piperidinopiperidine |
| 7 | H | 4-ethylpiperazine |
| 8 | H | 4-(2-hydroxyethyl)piperazine |
| 9 | H | 4-(2-dimethylaminoethyl)piperazine |
| 10 | H | 4-methylhomopiperazine |
| 11 | F | 1-methyl-4-aminopiperidine |
| 12 | F | 4-methylpiperazine |
| 13 | F | 4-aminopyridine |
| 14 | H | N,N-dimethylglycinamide (2HCl) |
| 15 | H | (4-methylpiperazin-1-yl)acetamide |

TABLE 10

| Entry | B with R$_1$ | NR$_6$R$_7$ |
|---|---|---|
| 1 | Ph | 4-phenylpiperazine |
| 2 | Ph | 4-(2-pyridyl)piperazine |
| 3 | Ph | 4-(2-pyrimidyl)piperazine |
| 4 | Ph | 4-(pyrrolidin-1-yl)piperidine |
| 5 | Ph | 4-(pyrrolidin-1-ylmethyl)piperidine |
| 6 | Ph | 4-((4-methylpiperazin-1-yl)methyl)piperidine |
| 7 | Ph | 4-(N,N-dimethylcarbamoyl)piperazine |
| 8 | 4-MeO—Ph | 4-methylpiperazine |
| 9 | 4-MeO—Ph | 4-aminopyridine |
| 10 | 3-F—Ph | 4-methylpiperazine |
| 11 | 3-F—Ph | 4-(dimethylamino)piperidine |
| 12 | 3-F—Ph | 4-aminopyridine |

TABLE 10-continued

| Entry | B with $R_1$ | $NR_6R_7$ |
|---|---|---|
| 13 | Et | piperazinyl-N—Me |
| 14 | Et | HN—(pyridin-4-yl) |
| 15 | cyc-Pr | piperazinyl-N—Me (2HCl) |
| 16 | cyc-Pr | piperidinyl-NMe$_2$ (2HCl) |
| 17 | cyc-Pr | HN—(pyridin-4-yl) |

Note: Ph is phenyl; cyc-Pr is cyclopropyl; Et is ethyl and Me is methyl.

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases, or to treat edema, effusions, exudates, or ascites and other conditions associated with vascular hyperpermeability.

DETAILED DESCRIPTION OF THE INVENTION

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

It is envisaged that the disorders listed above are mediated to a significant extent by protein tyrosine kinase activity involving the KDR/VEGFR-2 and/or the Flt-1/VEGFR-1 tyrosine kinases. By inhibiting the activity of these tyrosine kinases, the progression of the listed disorders is inhibited because the angiogenic or vascular hyperpermeability component of the disease state is severely curtailed. The action of the compounds of this invention, by their selectivity for specific tyrosine kinases, result in a minimization of side effects that would occur if less selective tyrosine kinase inhibitors were used.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, Src-subfamily kinases such as Lck, Src, fyn, yes, etc. Additionally, some compounds of this invention significantly inhibit serine/threonine kinases such as CDKs which play an essential role in cell-cycle progression. The potency and specificity of the generic compounds of this invention towards a particular protein kinase can often be altered and optimized by variations in the nature, number and arrangement of the substituents (i.e., $R_1$, $R_2$, $R_3$, $R_4$, $R_5$ and $R_6$) and conformational restrictions. In addition, the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278–1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Since Flt-1 tyrosine kinase activity may mediate important events in endothelial maintenance and vascular function, an inhibition of this enzyme activity may lead to toxic or adverse effects. At the very least, such inhibition is unnecessary for blocking the angiogenic responses, induction of vascular hyperpermeability and the formation of edema, so it is wasteful and of no value to the individual. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. The preferred compounds of this invention are, therefore, selective in their tyrosine kinase inhibitory activity.

The compounds of the present invention are also useful in the treatment of ulcers—bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, endometriosis, ovarian hyperstimulation syndrome, systemic lupus, sarcoidosis, synovitis, Crohn's disease, sickle cell anaemia, Lyme's disease, pemphigoid, Paget's disease, hyperviscosity syndrome, Osler-Weber-Rendu disease, chronic inflammation, chronic occlusive pulmonary disease, asthma, rheumatoid arthritis and osteoarthritis, and edema following trauma, radiation, or stroke.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of diabetic conditions such as glaucoma, diabetic retinopathy and microangiopathy.

It is envisaged that the disorders listed above are mediated to a significant extent by protein tyrosine kinase activity involving the VEGF receptors (e.g. KDR and Flt-1). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect, the present invention provides compounds of formula I as defined initially above (including the provisos) for use as medicaments, particularly as inhibitors of protein kinase activity for example tyrosine kinase activity, serine kinase activity and threonine kinase activity. In yet another aspect, the present invention provides the use of compounds of formula I as defined initially above (including the provisos) in the manufacture of a medicament for use in the inhibition of protein kinase activity.

In this invention, the following definitions are applicable:

"Pharmaceutically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

Pharmaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g. bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the organic molecule compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF, attenuate intracellular responses to VEGF, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, PKC inhibitors and PI3 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders, combinations with antiproliferative or cytotoxic chemotherapies or radiation are anticipated.

The present invention also comprises the use of a compound of formula I as a medicament.

Both the Src and Syk families of kinases play pivotal roles in the regulation of immune function. The Src family currently includes Fyn, Lck, Fgr, Fes, Lyn, Src, Yes, Hck, and Blk. The Syk family is currently understood to include only Zap and Syk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The kinases RIP, IRAK-1, IRAK-2, NIK, IKK-1 and IKK-2 are involved in the signal transduction pathways for the key pro-inflammatory cytokines TNF and IL-1. By virtue of their ability to inhibit one or more of these kinases, compounds of formula I may function as immunomodulatory agents useful for the maintenance of allografts and the treatment of autoimmune disorders. Through their ability to regulate T cell activation or the potentiation of an inflammatory process, these compounds could be used to treat such autoimmune diseases. Transplants due to rejection phenomena, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes.

Chromosome breakage (at the ltk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and they may become oncogenic by over-expression or mutation. By inhibiting the protein kinase activity of these proteins the disease process may be disrupted. Vascular restenosis may involve process of FGF and/or PDGF— promoted smooth muscle and endothelial cell proliferation. Inhibition of FGFr or PDGFr kinase activity may be an efficacious strategy for inhibiting this phenomenon. Thus compounds of formula I which inhibit the kinase activity of normal or aberrant c-kit, c-met, c-fms, src-family members, EGFr, erbB2, erbB4, BCR-Abl, PDGFr, FGFr, and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature. As a result of the "vascular permeability factor" activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and HIV-Tat protein can also cause a vascular hyperpermeability response through the stimulation of a VEGFR kinase. Tie-2 is expressed also in a select population of hematopoietic stem cells in which it may play a role in their recruitment, adhesion, regulation and differentiation (*Blood* 89, 4317–4326 (1997)); this Tie-2 expressing population may serve as circulating angiogenic endothelial progenitors. Certain agents according to formula I capable of blocking the kinase activity of endothelial cell specific kinases could therefore inhibit disease progression involving these situations.

The compounds of formula I or a salt thereof or pharmaceutical compositions containing a therapeutically effective amount thereof may be used in the treatment of benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, and adult respiratory distress syndrome (ARDS).

The compounds of the present invention may also be useful in the prophylaxis of the above diseases.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536–539) by a test compound relative to control.

KDR Tyrosine Kinase Production Using Baculovirus System

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6KDR(aa789-1354)$ were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at $2\times10^6$/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein in a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat #E-3641; 500 units/50 µl) and the EGF ligand was acquired from Oncogene Research Products/Calbiochem (Cat #PF011-100).

Expression of ZAP70

The baculoviral expression vector used was pVL1393 (Pharmingen, Los Angeles, Calif.). The nucleotide sequence encoding amino acids $M(H)6\ LVPR_9S$ was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Lck Source

Lck or truncated forms of Lck may be commercially obtained (e.g. from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly($Glu_4$ Tyr), 20,000–50,000 MW) was employed together with ATP (typically 5 µM) at concentrations approximately twice the apparent Km in the assay.

The following procedure was used to assay the inhibitory effect of compounds of this invention on KDR, Flt-1, Flt-4/VEGFR-3, Tie-2, EGFR and ZAP70 tyrosine kinase activity:

Buffers and Solutions
  PGT: Poly (Glu,Tyr) 4:1
    Store powder at −20° C. Dissolve powder in phosphate buffered saline (PBS) for 50 mg/ml solution. Store 1 ml aliquots at −20° C. When making plates dilute to 250 µg/ml in Gibco PBS.
  Reaction Buffer: 100 mM Hepes, 20 mM $MgCl_2$, 4 mM $MnCl_2$, 5 mM DTT, 0.02% BSA, 200 µM $NaVO_4$, pH 7.10
  ATP: Store aliquots of 100 mM at −20° C. Dilute to 20 µM in water
  Washing Buffer: PBS with 0.1% Tween 20
  Antibody Diluting Buffer: 0.1% bovine serum albumin (BSA) in PBS
  TMB Substrate: mix TMB substrate and peroxide solutions 9:1 just before use or use K-Blue Substrate from Neogen
  Stop Solution: 1M Phosphoric Acid Procedure
1. Plate Preparation:
   Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C.
   Wash 1× with 250 µl washing buffer and dry for about 2 hrs in 37° C. dry incubator. Store coated plates in sealed bag at 4° C. until used.
2. Tyrosine Kinase Reaction:
   Prepare inhibitor solutions at a 4× concentration in 20% DMSO in water.
   Prepare reaction buffer
   Prepare enzyme solution so that desired units are in 50 µl, e.g. for KDR make to 1 ng/µl for a total of 50 ng per well in the reactions. Store on ice.
   Make 4× ATP solution to 20 µM from 100 mM stock in water. Store on ice
   Add 50 µl of the enzyme solution per well (typically 5–50 ng enzyme/well depending on the specific activity of the kinase)
   Add 25 µl 4× inhibitor
   Add 25 µl 4× ATP for inhibitor assay
   Incubate for 10 minutes at room temperature
   Stop reaction by adding 50 µl 0.05N HCl per well
   Wash plate
   **Final Concentrations for Reaction: 5 µM ATP, 5% DMSO
3. Antibody Binding
   Dilute 1 mg/ml aliquot of PY20-HRP (Pierce) antibody (a phosphotyrosine antibody) to 50 ng/ml in 0.1% BSA in PBS by a 2 step dilution (100×, then 200×)
   Add 100 µl Ab per well. Incubate 1 hr at room temp. Incubate 1 hr at 4° C.
   Wash 4× plate
4. Color reaction
   Prepare TMB substrate and add 100 µl per well
   Monitor OD at 650 nm until 0.6 is reached
   Stop with 1M Phosphoric acid. Shake on plate reader.
   Read OD immediately at 450 nm Optimal incubation times and enzyme reaction conditions vary slightly with enzyme preparations and are determined empirically for each lot.

For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit KDR kinase at concentrations of 50 micromolar or below. Some compounds of this invention also significantly inhibit other PTKs such as lck at concentrations of 50 micromolar or below.

Cdc2 Source
The human recombinant enzyme and assay buffer may be obtained commercially (New England Biolabs, Beverly, Mass. USA) or purified from known natural or recombinant sources using conventional methods.

Cdc2 Assay
The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 µM ATP (31 µCi/ml) and 30 µg/ml histone type IIIss final concentrations. A reaction volume of 80 µL, containing units of enzyme, was run for 20 minutes at 25 degrees C. in the presence or absence of inhibitor. The reaction was terminated by the addition of 120 µL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant. Certain compounds of this invention significantly inhibit cdc2 at concentrations below 50 uM.

PKC Kinase Source
The catalytic subunit of PKC may be obtained commercially (Calbiochem).

PKC Kinase Assay
A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10 mM $MgCl_2$, 2 mM DTT, 1 mM EGTA, 100 µM ATP, 8 µM peptide, 5% DMSO and $^{33}P$ ATP (8 Ci/nM). Compound and enzyme were mixed in the reaction vessel and the reaction initiated by addition of the ATP and substrate mixture. Following termination of the reaction by the addition of 10 µL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source
The recombinant murine enzyme and assay buffer may be obtained commercially (New England Biolabs, Beverly Mass. USA) or purified from known natural or recombinant sources using conventional methods.

Erk2 Enzyme Assay
In brief, the reaction was carried out in a buffer consisting of 50 mM Tris pH 7.5, 1 mM EGTA, 2 mM DTT, 0.01% Brij, 5% DMSO and 10 mM $MgCl_2$ (commercial buffer) supplemented with fresh 100 µM ATP (31 µCi/ml) and 30 µM myelin basic protein under conditions recommended by the supplier. Reaction volumes and method of assaying incorporated radioactivity were as described for the PKC assay (vide supra).

In Vitro Models for T-cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 µl volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$ M 2 mercaptoethanol and 0.5% DMSO, The cultures are pulsed with 0.5 µCi of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 µg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α(TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 µg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6 \times 10^6$ per ml in tissue culture medium (RPMI 1640 supplemented with heat inactivated fetal bovine serum (Hyclone Laboratories) $5 \times 10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model:J. Immunol 146 (4):1163–8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/ peptide immunized animals.

CIA may be induced in DBA/1 mice by immunization with type II collagen (J. Immunol: 142(7):2237–2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation: 57(12): 1701-17D6, 1994) or heart (Am.J.Anat.:113:273, 1963). Briefly, full thickness skin grafts are transplanted from C57BL/6 mice to BALB/c mice. The grafts are examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDRNVEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3–8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5-1.0 \times 10^5$ cells/well in each well of 6-well cluster plates (Costar; Cambridge, Mass.).

3. 3-4 days after seeding, plates were 90–100% confluent. Medium was removed from all the wells, cells were rinsed with 5–10 ml of PBS and incubated 18–24 h with 5 ml of EBM base media with no supplements added (i.e., serum starvation).

4. Serial dilutions of inhibitors were added in 1 ml of EBM media (25 µM, 5 µM, or 1 µM final concentration to cells and incubated for one hour at 37° C. Human recombinant $VEGF_{165}$ (R & D Systems) was then added to all the wells in 2 ml of EBM medium at a final concentration of 50 ng/ml and incubated at 37° C. for 10 minutes. Control cells untreated or treated with VEGF only were used to assess background phosphorylation and phosphorylation induction by VEGF.

All wells were then rinsed with 5–10 of cold PBS containing 1 mM Sodium Orthovanadate (Sigma) and cells were lysed and scraped in 200 μl of RiPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 μg/ml, pepstatin 1 μg/ml, leupeptin 1 μg/ml, Na vanadate 1 mM, Na fluoride 1 mM) and 1 μg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (−20° C.) ethanol (2 volumes) for a minimum of 1 hour or a maximum of overnight. Pellets were reconstituted in Laemli sample buffer containing 5%β-mercaptoethanol (BioRad; Hercules, Calif.) and boiled for 5 min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated F(ab)$_2$ of goat anti-rabbit or goat-anti-mouse IgG the bands were visualized using the emission chemiluminescence (ECL) system (Amersham Life Sciences, Arlington Height, Ill.). Certain examples of the present invention significantly inhibit cellular VEGF-induced KDR tyrosine kinase phosphorylation at concentrations of less than 50 μM.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (Endocrinology (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones were purchased from Sigma (St. Louis, Mo.) or Cal Biochem (La Jolla, Calif.) as lyophilized powders and prepared according to supplier instructions.

Vehicle components (DMSO, Cremaphor EL) were purchased from Sigma (St. Louis, Mo.).

Mice (Balb/c, 8–12 weeks old) were purchased from Taconic (Germantown, N.Y.) and housed in a pathogen-free animal facility in accordance with institutional Animal Care and Use Committee Guidelines.

Method

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5–10. Test compounds were administered by i.p., i.v. or p.o. routes depending on solubility and vehicle at doses ranging from 1–100 mg/kg. Vehicle control group received vehicle only and two groups were left untreated.

Thirty minutes later, experimental, vehicle and one of the untreated groups were given an i.p. injection of 17β-estradiol (500 μg/kg). After 2–3 hours, the animals were sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing. Mean weights of treated groups were compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear "marble" of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. (1995), 15(11), 1857–6). The model preferably runs over 3-4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXAMPLES

I. Synthesis

There are two general approaches to the synthesis of the ring systems of the compounds of formula I that have been set forth in U.S. Pat. Nos. 3,843,665 and 3,843,666.

In U.S. Pat. No. 3,843,665, cyclization of the pyrazole ring is affected by heating compounds of formula II with an aromatic sulfonylhydrazide of formula III in an inert solvent and a catalytic amount of an acid. The reaction is carried out for a period of 5 to 30 hours preferably at a temperature of 75° C. to 100° C. and gives compounds of formula I.

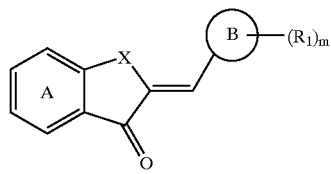

-continued

III

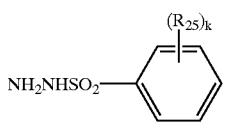

wherein:

k is 0, 1, 2; $R_{25}$ is a lower alkyl; and X, $R_1$, m, ring A and B are as previously defined. Compounds of formula II are prepared by treating an appropriately functionalized compounds of formula IV with an aldehyde of formula V in the presence of an acid or base catalyst (Braun, R. A.; Mosher, W. A. J. Amer. Chem. Soc. 1958, 80, 2749).

IV

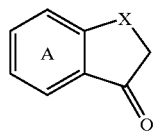

V

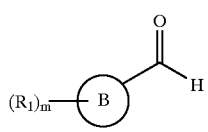

A second method of preparing the ring systems of the compounds of formula I is set forth by U.S. Pat. No. 3,843,666 where compounds with the general formula VI are heated to 75° to 175° C. with a catalytic amount of an organic carboxylic acid or an organic sulfonic acid in an inert solvent such as an aromatic hydrocarbon for a period of 6 to 24 hours,

VI

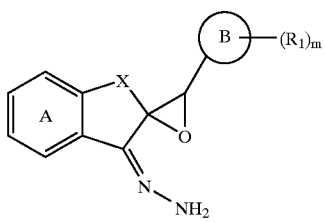

wherein:

X, $R_1$, m, ring A and B are as previously defined.

Compounds of formula VI are prepared by treating compounds of the general formula VII with hydrazine in an inert solvent. The reaction is carried out at 15° to 20° C. for a period of up to 24 hours.

VII

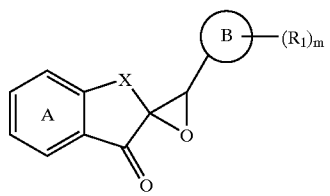

Alternatively compounds of formula I may be prepared directly by reacting a compound of formula VII with hydrazine without isolating the compound of formula VI, for example by heating a compound of formula VII with hydrazine in an inert solvent, e.g. methanol, in the presence of an acid catalyst, e.g. acetic acid, at a temperature in the range from 60° C. to the boiling point of the inert solvent employed.

Compounds of formula I may also be prepared by reacting a compound of formula XVI

XVI

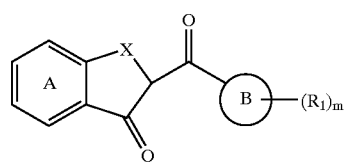

wherein:

X, $R_1$, m, ring A and B are as previously defined with hydrazine in an inert solvent e.g. methanol, at a temperature in the range of from 15° C. to the boiling point of the inert solvent employed.

Compounds which have the general formula VII are prepared by treating a compound of formula VIII with an aldehyde of formula V under basic conditions. The reaction is carried out in an inert solvent at a temperature between 5° C. and 10° C. for a period of 3 to 6 hours,

VIII

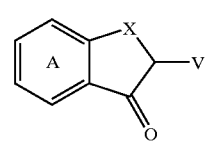

wherein:

V is any conventional leaving group, such as chlorine, bromine, iodine, tosylate or mesylate and X, and ring A are as previously defined.

Compounds of formula VII may also be prepared by reacting a compound of formula II with an epoxidizing agent, for example hydrogen peroxide, in an inert solvent, for example methanol, dichloromethane, water or mixtures thereof, at a temperature in the range of 0° to 100° C. optionally in the presence of a base, for example sodium hydroxide.

Cyclization of VI can also be effected by treatment with a mineral acid such as hydrochloric acid, sulfuric acid or phosphoric acid. The reaction is carried out in a lower alkanol at a temperature between 15° C. to 20° C. for a period of 12 to 48 hours. The product of the reaction, IX, can then be aromatized to I by heating to a temperature of 50° C. to 150° C. with an organic carboxylic acid or an organic sulfonic acid in a straight chain ether or cyclic ether for the period of 8 to 30 hours.

IX

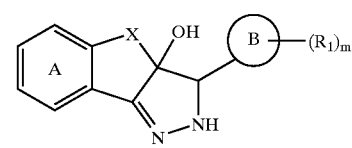

Compound IX can be diacetylated by treatment with an acid anhydride of formula $(R_xCO)_2O(X)$ in which $R_x$ is a $C_{1-4}$ alkyl group in an inert solvent such as an aromatic hydrocarbon at a temperature between 35° C. to 200° C. for a period of 5 to 8 hours to give a compound of formula XI.

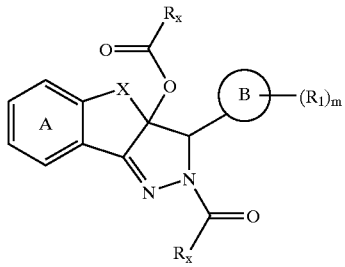

XI

Compound XI can then be aromatized to compound XII by heating to a temperature of 35° C. to 200° C. with a mineral acid or an organic acid in an inert solvent for the period of 4 to 8 hours. Finally, compound XII can be converted to I by heating to a temperature of 50° C. to 150° C. in an inert solvent such as water or a lower alcohol in the presence of an alkali metal or an alkali metal hydroxide for the period of 8 to 30 hours.

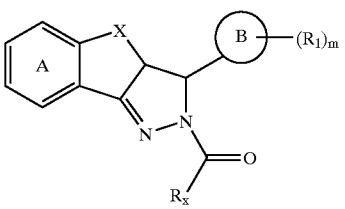

XII

Compounds with the general formula II can be cyclized to compounds of formula XIII by reaction with hydrazine in an inert solvent, for example methanol, at a temperature in the range of 35–150° C.

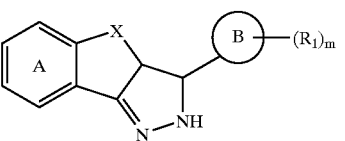

XIII

Compounds of formula I may be prepared by reacting a compound of formula XIII with a dehydrogenating agent, for example sulphur, oxygen, palladium, manganese dioxide or lead dioxide optionally in the presence of an inert solvent, for example a hydrocarbon, at a temperature in the range of 15 to 250° C.

Specific examples of the above transformations can be found in U.S. Pat. Nos. 3,843,665 and 3,843,666.

The bridging carbonyl can be transformed to a methylene group via a Wolf-Kishner reduction of the corresponding hydrazone (Mosher, W. A., Tawfik, E.-Z., Lipp, D. W. *J Org. Chem.* 1971, 36, 3890).

Additional methods for functionalization of the bridging carbonyl and specific examples can be found in Japanese Patent Application JP 60 130521 A2, and B. Loev, U.S. Pat. No. 3,004,983 (1960).

Compounds of formula I may be prepared by reacting a compound of formula XIV

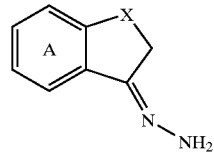

XIV with a strong base, for example n-butyllithium at a temperature in the range of −78° C. to 25° C., followed by reaction with a compound of formula:

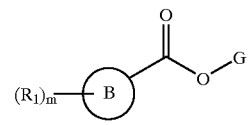

XV wherein B is as previously defined and G represents a $C_{1-6}$ alkoxy group or an aryl which is optionally substituted with a halo.

In an alternative approach, B can be added to a compound represented by structural formula XVII using the conditions set forth in Table 11 (see Scheme I):

SCHEME I

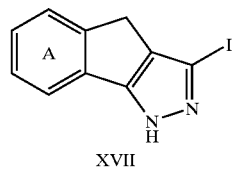

XVII

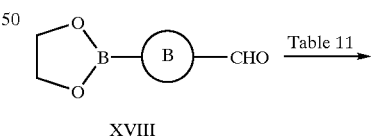

XVIII

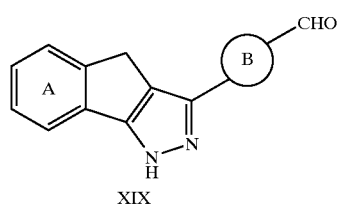

XIX

TABLE 11

| Entry | XVIII | Base | Pd catalyst | Conditions | Yield of XIX |
|---|---|---|---|---|---|
| 1 | dioxaborolane-C6H4-CHO (× 1.2 mol) | $K_3PO_4$ (× 1.5 mol) | $Pd(PPh_3)_4$ (× 5 mol %) | 100 deg, 20 h in DMF (under $N_2$) | 43% (isolated) |
| 2 | dioxaborolane-C6H4-CHO (× 1.5 mol) | $K_3PO_4$ (× 1.5 mol) | $Pd(PPh_3)_4$ (× 5 mol %) | 100 deg, 24 h in DMF (under $N_2$) | 39% (isolated) |
| 3 | dioxaborolane-C6H4-CHO (× 1.2 mol) | $K_3PO_4$ (× 1.5 mol) | $PdCl2(PPh_3)_2$ (× 5 mol %) | 100 deg in DMF (under $N_2$) | Small amount (by TLC) |
| 4 | dioxaborolane-C6H4-CHO (× 1.2 mol) | $K_3PO_4$ (× 1.5 mol) | $Pd(PPh_3)_4$ (× 5 mol %) | 100 deg in NMP (under $N_2$) | Small amount (by TLC) |

In general, protection of the pyrazole ring of XVII before addition of B improves the product yield. For example when the pyrazole ring of XVII is protected with di(p-methoxyphenyl)methyl the yield is significantly improved (see 5 Table 12).

TABLE 12

| Entry | XVIII | Base | Pd catalyst | Conditions | Yield of protected XIX |
|---|---|---|---|---|---|
| 1 | dioxaborolane-C6H4-CHO (× 1.2 mol) | $K_3PO_4$ (× 1.5 mol) | $Pd(PPh_3)_4$ (× 5 mol %) | 100 deg, 15 h in DMF (under $N_2$) | 81% (isolated) |
| 2 | dioxaborolane-C6H4-CHO (× 1.5 mol) | $K_3PO_4$ (× 1.5 mol) | $Pd(PPh_3)_4$ (× 5 mol %) | 100 deg, 24 h in DMF (under $N_2$) | 79% (isolated) |
| 3 | dioxaborolane-C6H4-CHO (× 1.2 mol) | $K_3PO_4$ (× 1.5 mol) | $PdCl_2(PPh_3)_2$ (× 5 mol %) | 100 deg, 29 h in DMF (under $N_2$) | 80% (isolated) |
| 4 | dioxaborolane-C6H4-CHO (× 1.2 mol) | $K_3PO_4$ (× 1.5 mol) | $Pd(PPh_3)_4$ (× 5 mol %) | 100 deg, 32 h in NMP (under $N_2$) | 50% (isolated) |
| 5 | dioxaborolane-C6H4-CHO (× 1.2 mol) | $K_3PO_4$ (× 1.5 mol) | $Pd(PPh_3)_4$ (× 5 mol %) | 100 deg, 24 h in 1,4-dioxane (under $N_2$) | Small amount (by TLC) |

TABLE 12-continued

| Entry | XVIII | Base | Pd catalyst | Conditions | Yield of protected XIX |
|---|---|---|---|---|---|
| 6 | (dioxaborolane)-C6H4-CHO (x 1.2 mol) | $K_3PO_4$ (x 1.5 mol) | $Pd(PPh_3)_4$ (x 5 mol %) | 100 deg, 2 h in 2-methoxy-ethanol (under $N_2$) | 80% (isolated) |
| 7 | (dioxaborolane)-C6H4-CHO (x 1.2 mol) | $K_2CO_3$ (x 1.1 mol) | $Pd(PPh_3)_4$ (x 5 mol %) | 100 deg, 6 h in DMF (under $N_2$) | 77% (isolated) |
| 8 | (HO)$_2$B-C6H4-CHO (x 1.2 mol) | $K_3PO_4$ (x 1.5 mol) | $Pd(PPh_3)_4$ (x 5 mol %) | 100 deg, 24 h in DMF (under $N_2$) | Small amount (by TLC) |

Compounds of formula IV, VIII, XIV, XV and XVI are commercially available or may be prepared by methods known to those skilled in the art.

Compounds of formula I in which X represents SO, or $SO_2$ may be prepared by oxidizing a compound of formula I in which X represents S by methods known to those skilled in the art for example by using an appropriate number of molar equivalents of 3-chloroperbenzoic acid.

Compounds of formula I in which X represents a group of formula —C=NOR$_7$ may be prepared by reacting a compound of formula I in which X represents carbonyl, with a compound of formula $H_2NOR_7$ by methods known to those skilled in the art.

Compounds of formula I in which B is 4-pyridyl may be further functionalized in the 2-position of the pyridine ring by methods known to those skilled in the art, for example, via pyridine-N-oxide mediated rearrangements.

Certain substituents in compounds of formula I may be interconverted by methods known to those skilled in the art. For example alkoxy substituents may be reacted with a suitable ether cleaving reagent for example hydrobromic acid, boron tribromide or pyridine hydrochloride to give a compound of formula I with a hydroxy substituent. Alternatively compounds of formula I with an alkoxy substituent may be prepared by alkylating compounds of formula I which have a hydroxy substituent. An aliphatic hydroxy group can be converted into a good leaving group by reacting it with tosyl chloride or mesyl chloride. The leaving group can then be displaced with a nucleophile such as a primary or secondary amine under basic reaction conditions. Aliphatic halo substituents can also be displaced by nucleophilic reactants such as primary or secondary amines. Carboxylic ester substituents may be converted into carboxy or amide substituents and carboxylic acid substituents may be converted into carboxylic ester or amide substituents. An ester substituent can be converted to a hydroxymethyl group by treating the ester with a reducing agent such as DIBAL-H. A Swern oxidation can be used to convert a hydroxyl group to an aldehyde or a ketone. An aldehyde can be converted to an amide by treating the aldehyde with a primary or secondary amine under basic conditions. An amide can be converted to an amine by treatment with a reducing agent such a hydrogen in the presence of a $PtO_2$ catalyst. Nitro substituents may be reduced to amines and amines may be acylated by methods known to those skilled in the art.

It will be appreciated by those skilled in the art that certain substituents may react with some of the reagents described in the above processes. In such cases an alternative process should be used or the reactive substituent should be protected prior to the reaction and deprotected after the reaction.

The invention is illustrated by the following Examples which are given by way of example only. The final product of each of these Examples was characterized by one or more of the following procedures: high performance liquid chromatography; elemental analysis, nuclear magnetic resonance spectroscopy, infrared spectroscopy and high resolution mass spectroscopy. The following abbreviations are used IMS=industrial methylated spirit LCMS=liquid chromatography/mass spectroscopy.

Example 1 a) A mixture of indan-1-one (10.0 g), ethanol (35 ml), hydrazine hydrate (10.0 ml) and glacial acetic acid (2.0 ml) was boiled under reflux under nitrogen for 1 hour. The mixture was cooled to 20° C. and the mixture concentrated under reduced pressure to give a solid which was collected by filtration to give indan-1-one hydrazone, m.p. 84–86° C.

b) A solution of n-butyllithium (15.0 ml of a 2.5M solution in hexane) was added dropwise to a mixture of the hydrazone from a) (1.82 g) in tetrahydrofuran (40 ml) at 0° C. under nitrogen with stirring. The mixture was stirred at 0° C. for 0.5 hours and then methyl 3,4,5-trimethoxybenzoate (1.41 g) was added dropwise over 10 minutes and the mixture was stirred at 0° C. for 20 minutes. Dilute hydrochloric acid (40 ml, 3M) was added and the mixture was boiled under reflux for 1 hour. The mixture was cooled to ambient temperature and separated. The aqueous layer was neutralized with sodium bicarbonate and extracted with ether to give a brown oil. The oil was purified by flash column chromatography on silica using ethyl acetate/petroleum ether (1:4) as the mobile phase to give 3-(3,4,5-trimethoxyphenyl)-1,4-dihydroindeno[1,2-c]-pyrazole, m.p. 185–187° C.

Example 2 a) In a similar manner to Example 1, indan-1-one hydrazone (3.55 g) was dissolved in tetrahydrofuran (80 ml)

at 0° C. under nitrogen with stirring. n-Butyllithium (28.8 ml of a 2.5M solution in hexane) was added to the solution and the mixture was stirred at 0° C. for 0.5 h. Ethyl 3-methoxybenzoate (2.16 g) was added, followed by 3M hydrochloric acid (80 ml) and the mixture was worked up as described in Example 1 to give 3-(3-methoxyphenyl)-1,4-dihydroindeno[1,2-c]pyrazole, m.p. 172–174° C.

b) A solution of boron tribromide in dichloromethane (4.58 ml of a 1M solution) was added with stirring to a suspension of the product from a) (0.30 g) in dichloromethane (30 ml) at −40° C. with stirring under nitrogen. The mixture was stirred at between −40° C. and −20° C. for 0.5 h and then warmed to ambient temperature. The mixture was stirred at ambient temperature for 0.5 h and then poured into methanol 100 ml. Silica was added and the mixture was preabsorbed onto silica and then purified by flash column chromatography using ethyl acetate/petroleum ether (1:2.5 increasing the proportion of ethyl acetate until 100% ethyl acetate was reached and finally using ethyl acetate/methanol (1:1)). Appropriate fractions were collected, combined and recrystallized from ethanol to give 3-(1,4-dihydroindeno-[1,2-c]pyrazol-3-yl)phenol, m.p. 302–304° C.

Example 3

A mixture of 2-benzoylbenzo[b]thiophen-3(2H)-one (1.50 g, supplied by the Maybridge Chemical Company, Tintagel, England) hydrazine hydrate (0.3 ml) and butan-1-ol (50 ml) was boiled under reflux under nitrogen for 7.5 hours. The solvent was removed under reduced pressure and the residue was taken up in ethyl acetate, washed with water, dried, filtered and evaporated to give a solid which was purified by flash column chromatography on silica using toluene/ethyl acetate (7.5:1) as the mobile phase. Appropriate fractions were collected, combined and evaporated to give a solid which was triturated with ether, and filtered to give 3-phenyl-1H-[1]benzothieno[3,2-c]pyrazole, m.p. 236–238° C.

Example 4

A solution of 3-chloroperoxybenzoic acid (450 mg, 60% pure) in dichloromethane (30 ml) was added dropwise with stirring over 15 minutes to a solution of 3-phenyl-1H-[1]benzothieno[3,2-c]pyrazole (400 mg) in dichloromethane (50 ml) at 0–5° C. The mixture was stirred at 5–15° C. for 4 hours, then washed with water, dried and evaporated to give a solid which was purified by chromatography on silica using petroleum ether/ethyl acetate (1:3) as the mobile phase. Appropriate fractions were collected, combined and evaporated to give a solid which was triturated with ether, and filtered to give 3-phenyl-1H-[1]benzothieno[3,2-c]pyrazole 4-oxide, m.p. 222–224° C.

Example 5

A solution of 3-chloroperoxybenzoic acid (440 mg, 60% pure) in dichloromethane (30 ml) was added dropwise with stirring over 15 minutes to a solution of 3-phenyl-1H-[1]benzothieno[3,2-c]pyrazole (190 mg) in dichloromethane (30 ml) at 0–5° C. The mixture was stirred at 5–15° C. for 4 hours with more 3-chloroperoxybenzoic acid (220 mg) being added after 2 hours. The reaction mixture was washed with water, dried, filtered and evaporated to give a solid which was dissolved in ethyl acetate (100 ml), washed with 1M sodium hydroxide solution (50 ml), then with water and then dried, filtered and evaporated to give a solid which was triturated with ether and filtered to give 3-phenyl-1H-[1]benzothieno-[3,2-c]pyrazole 4,4-dioxide, m.p. 266–268° C.

Example 6

A mixture of 3-phenylindeno[1,2-c]pyrazol-4(1H)-one (1.28 g, prepared as described in JP60–130521), hydroxylamine hydrochloride (0.5 g), sodium acetate (0.8 g), water (10 ml) and methanol (100 ml) was boiled under reflux for 66 hours. More hydroxylamine hydrochloride (0.5 g), sodium acetate (0.8 g) and water (10 ml) were added and the mixture was boiled under reflux for a further 16 hours. Further hydroxylamine hydrochloride (0.5 g) and sodium acetate (0.8 g) were added and the mixture was boiled under reflux for a further 20 hours. The mixture was filtered and the filtrate was concentrated under reduced pressure until crystallization began. The mixture was cooled and filtered to give a solid which was washed with water and dried to give 3-phenylindeno[1,2-c]pyrazol-4(1H)-one oxime, m.p. 280° C. (with decomposition).

Example 7 a) A mixture of indan-1-one (3.3 g), methyl 4-formylbenzoate (5.0 g), piperidine (0.6 ml) and glacial acetic acid (0.5 ml) was heated on a steam bath for 3 hours. The solid mass obtained was boiled up in industrial methylated spirits (200 ml) and then hot filtered. The solid residue obtained was washed with industrial methylated spirits and dried to give methyl 4-(1-oxoindan-2-ylidenemethyl)benzoate, m.p. 194–198° C.

b) The product from a) (1.5 g) was suspended in methanol (10 ml) and dichloromethane (15 ml) and stirred at 0–5° C. whilst 2M sodium hydroxide solution (2.7 ml) was added followed by 30% hydrogen peroxide (100 vol. 1.1 ml). The mixture was stirred at 0–5° C. for 5 minutes then at ambient temperature for 24 hours. Dichloromethane (100 ml) was added to the mixture which was then washed with brine (2×50 ml), dried, filtered and evaporated to give methyl 4-(1-oxospiro[indan-2,2'-oxiran]-3'-yl)benzoate, m.p. 160–163° C. The aqueous phase was acidified with 5M hydrochloric acid and extracted with dichloromethane to give 4-(1-oxospiro[indan-2,2'-oxiran]-3'-yl)benzoic acid, m.p. 220° C. with decomposition.

c) A mixture of 4-(1-oxospiro[indan-2,2'-oxiran]-3'-yl) benzoic acid (750 mg), methanol (30 ml) and hydrazine hydrate (0.16 ml) was stirred at ambient temperature whilst glacial acetic acid (6 drops) were added. The mixture was boiled under reflux for 24 hours and then allowed to stand at ambient temperature for 24 hours, then cooled to 0° C. and filtered to give methyl 4-(1, 4-dihydroindeno [1,2-c]pyrazol-3-yl)benzoate, m.p. 224–226° C.

Example 8

4-(1-Oxospiro[indan-2,2'-oxiran]-3'-yl)benzoic acid from Example 7b (780 mg), methanol (50 ml), hydrazine hydrate (0.18 ml) and glacial acetic acid (6 drops) were boiled under reflux for 24 hours. The mixture was cooled in ice and filtered to give 4-(1,4-dihydroindeno[1,2-c]pyrazol-3-yl) benzoic acid, m.p. >320° C.

Example 9

A mixture of 4-(1,4-dihydroindeno[1,2-c]pyrazol-3-yl) benzoic acid (1.05 g) and dry tetrahydrofuran (30 ml) was stirred at ambient temperature whilst triethylamine (1.1 ml) was added. The mixture was stirred at ambient temperature for 0.5 h then cooled to 3° C. and methyl chloroformate (1.2 ml) was added dropwise over 5 to 10 minutes at 3–9° C. The mixture was stirred for 1 hour at 3–9° C. and then added to concentrated aqueous ammonia solution (70 ml, SG 0.880) with rapid stirring. The mixture was stirred for 2 hours at 5° C. and allowed to warm up to ambient temperature. The mixture was concentrated under reduced pressure and then treated with 1M sodium hydroxide solution (200 ml). The mixture was stirred for 0.5 hour and then filtered. The solid obtained was stirred with 2M sodium hydroxide solution (50 ml) for 6 hours and then allowed to stand at ambient temperature for 18 hours. The mixture was filtered to give a solid which was washed with water and dried. This solid was purified by flash column chromatography on silica using dichloromethane/industrial methylated spirit/triethylamine (25:2.5:1.5) as the mobile phase. The appropriate fractions were combined and concentrated to give a residue which was washed with water and dried under vacuum at 40° C. to give 4-(1,4-dihydroindeno[1,2-c]pyrazol-3-yl)benzamide, m.p. 290–293° C.

Examples 10 and 11 a) A mixture of N-(1-oxoindan-5-yl)acetamide (10.0 g, obtained from the Maybridge Chemical Co. Ltd), benzaldehyde (6.73 g), glacial acetic acid (1.06 g) and piperidine (10.8 g) was heated to 90° C. under nitrogen. Methanol (200 ml) was added and the mixture was cooled and then filtered to give N-(2-benzylidene-1-oxo-indan-5-yl)acetamide (13.47 g).

b) The product from a) above (9.20 g), dichloromethane (30 ml) and methanol (30 ml) was stirred at 20° C. before adding 2M sodium hydroxide solution (15 ml) and hydrogen peroxide (6.6 ml, 100 volumes) with stirring at 20° C. The mixture was stirred at 20° C. for 24 hours. Further hydrogen peroxide (3 ml, 100 volumes) was added and the mixture was stirred for 24 hours. The mixture was neutralized with glacial acetic acid and the solid obtained was collected by filtration to give N-(1-oxo-3'-phenylspiro[indan-2,2'-oxiran]-5-yl)acetamide, m.p. 195–197° C.

c) The product from b) (2.0 g) was dissolved in ethanol (30 ml) and then hydrazine hydrate (0.34 g) was added followed by glacial acetic acid (30 drops). The mixture was boiled under reflux for 5 hours, then cooled. A solid was collected by filtration and purified by flash column chromatography on silica using dichloromethane/methanol (95:5) as the mobile phase to give N-(3-phenyl-1,4-dihydroindeno[1,2-c]pyrazol-6-yl)acetamide, m.p. 275–276° C. as Example 10.

Certain fractions from the chromatography contained another compound in addition to Example 10. These fractions were combined and evaporated under reduced pressure. The residue obtained was dissolved in ethyl acetate and extracted with 2M hydrochloric acid. The combined acid extracts were basified with 2M sodium hydroxide solution and filtered to give 3-phenyl-1,4-dihydroindeno[1,2-c]pyrazol-6-ylamine, m.p. 228–230° C. as Example 11.

Example 12 a) A mixture of indan-1-one (20.0 g), 4-nitrobenzaldehyde (27.0 g), glacial acetic acid (3.0 g) and piperidine (3.06 g) was heated at 95° C. under nitrogen for 3.5 h. The mixture was cooled to 20° C. and filtered to give a solid which was recrystallized from industrial methylated spirit to give 2-(4-nitrobenzylidene)indan-1-one.

b) The product from a) (28.0 g) was stirred with dichloromethane (100 ml) and methanol (100 ml) at 20° C. and then 2M sodium hydroxide solution (50 ml) was added followed by hydrogen peroxide (20 ml, 100 volumes). The mixture was stirred at 20° C. for 24 hours. Further hydrogen peroxide (10.0 ml, 100 volumes) was added and the mixture was stirred for a further 24 hours. Further hydrogen peroxide (10 ml, 100 volumes) was added and the mixture was stirred for 64 hours. The reaction mixture was neutralized with glacial acetic acid and the solid which formed was collected by filtration and dried to give 3'-(4-nitrophenyl)-1-oxospiro[indan-2,2'-oxirane].

c) The product from b) (10.0 g) was dissolved in ethanol (180 ml) and hyrazine hydrate (1.78 g) was added to the solution obtained, followed by glacial acetic acid (30 drops). The mixture was boiled under reflux for 5 hours and then cooled to 20° C. and stood at this temperature for 18 hours. The solid was collected by filtration and recrystallized from acetone to give 3-(4-nitrophenyl)-1,4-dihydroindeno[1,2-c]pyrazole, m.p. 267–270° C.

Example 13

The product from Example 12 (3.0 g) was suspended in industrial methylated spirit (200 ml) and 5% palladium on charcoal (250 mg) was added followed by ammonium formate (2.05 g). The mixture was stirred and heated at 70° C. for 3 hours and then cooled to ambient temperature and then filtered. The filtrate was concentrated under reduced pressure and triturated with dichloromethane to give 4-(1,4-dihydroindeno[1,2-c]pyrazol-3-yl)aniline, m.p. 253–254° C.

Example 14

3-(4-Pyridyl)-4,5-dihydro-1H-benzo[g]indazole (100 mg, compound commercially available from Aldrich) was dissolved in tetrahydrofuran (5–10 ml) with warming and then 3-chloroperoxybenzoic acid (1.25 molar equivalents of 70–75% pure material) was added. The mixture was heated at 55–60° C. for 4 hours. A precipitate was collected by filtration, washed with tetrahydrofuran and then ether to give 4-(4,5-dihydro-1H-benzo[g]indazol-3-yl)pyridine 1-oxide.

Example 15

The N-oxide product from Example 14 (150 mg) was dissolved in phosphorus oxychloride (6 ml). The mixture was boiled under reflux for 4 hours. Excess phosphorus oxychloride was removed under reduced pressure and the residue was washed with saturated sodium carbonate solution and the product was extracted into chloroform, washed, dried and evaporated to give 3-(2-chloro-4-pyridyl)-4,5-dihydro-1H-benzo[g]indazole.

Example 16

The N-oxide product from Example 14 (25 mg) was suspended in dimethyl-formamide (200 μl) and to this suspension was added trimethylsilyl cyanide (5 molar equivalents) and triethylamine (3 molar equivalents). The mixture was heated at 110° C. for 12 hours and was then diluted with dichloromethane and washed with saturated sodium bicarbonate solution. The organic layer was separated, dried, filtered and evaporated to give, after flash column chromatography using 20–40% of acetonitrile in dichloromethane as the mobile phase, 4-(4,5-dihydro-1H-benzo[g]indazol-3-yl)-2-pyridinecarbonitrile.

Example 17

The product from Example 16 (50 mg) was suspended in a mixture of ethanol (1 ml) and water (0.5 ml) containing sodium carbonate (1 molar equivalent) and hydroxylamine hydrochloride (2 molar equivalents). The mixture was boiled under reflux for 4 hours, then cooled. A precipitate formed which was collected by filtration to give 4-(4,5-dihydro-1H-benzo[g]indazol-3-yl)-2-pyridinecarboxamide oxime.

Example 18

Potassium carbonate (1 molar equivalent) was added to a mixture of the product from Example 16 (50 mg), DMSO (600 µl), followed by the addition of hydrogen peroxide (250 µl of a 30% solution) which was added dropwise. Within a few minutes of the completion of the addition a precipitate had formed. The mixture was stirred for 1 hour and then water was added. The precipitate was collected by filtration to give 4-(4,5-dihydro-1H-benzo[g]indazol-3-yl)-2-pyridine carboxamide.

Example 19

Palladium on charcoal (a spatula tip of 10% material) was added to a suspension of the product from Example 16 (50 mg) in a mixture of trifluoroacetic acid in methanol (5 ml of a 5% v/v solution of trifluoroacetic acid in methanol) and the mixture was kept in an atmosphere of hydrogen for 24 hours with stirring. The mixture was filtered to remove the catalyst and the filtrate was concentrated under reduced pressure (to around 0.5 ml). Ethereal hydrogen chloride (20 ml) was added and the precipitate which formed was collected by filtration and dried to give {[4-(4,5-dihydro-1H-benzo[g]indazol-3-yl)-2-pyridyl]methyl}ammonium chloride.

Example 20

The product from Example 19 (100 mg) was suspended in propyl form ate (10 ml) and ethanol (1.5 ml). This mixture was boiled under reflux and after 2 minutes triethylamine (0.5 ml) was added. The mixture was boiled under reflux for 4 hours and then cooled and diluted with dichloromethane (50 ml). The mixture was washed with water, then dried, filtered and evaporated to give a residue which was triturated with ether and dichloromethane to give N-{[4-(4,5-dihydro-1H-benzo[g]-indazol-3-yl)-2-pyridyl]methyl}formamide.

Examples 21–24

The following examples are commercially available or may be prepared by methods analogous to those described in examples 1–6.

Example 21

3-(3,4-Dimethoxyphenyl)indeno[1,2-c]pyrazol-4(1H)-one oxime.

Example 22

3-(4-Methylphenyl)indeno[1,2-c]pyrazol-4(1H)-one oxime (available from Menai).

Example 23

3-(2-Thienyl)indeno[1,2-c]pyrazol-4(1H)-one (was commercially available or may be prepared by methods analogous to those described in JP60-130521).

Example 24

3-Phenyl-1H-benzofuro[3,2-c]pyrazole.

Example 25

A mixture of 4-(1,4-dihydroindeno[1,2-c]pyrazol-3-yl)benzoic acid (0.8 g), methylamine in ethanol (0.27 ml of a 33% w/w solution), 4-pyrrolidinopyridine (0.47 g), diisopropylcarbodiimide (0.5 ml) and dichloromethane (30 ml) was stirred at ambient temperature for 20 hours. More methylamine in ethanol (0.3 ml of a 33% w/w solution), 4-pyrrolidinopyridine (0.5 g) and diisopropylcarbodiimide (1 ml) were added and the mixture was stirred for 3 hours at ambient temperature. The solvent was removed under reduced pressure at 50° C. The mixture was kept under vacuum for 2 hours and then dichloromethane (50 ml) was added. The mixture was stirred at ambient temperature for 20 hours and then allowed to stand for 72 hours. A solid was removed by filtration and purified by flash column chromatography on silica using toluene/acetic acid (10:1) and then ethyl acetate as the mobile phase to give N-methyl-4-(1,4-dihydroindeno[1,2-c]pyrazol-3-yl)benzamide, m.p. 182–188° C.

Example 26 a) Lithium diisopropylamide (27.2 ml of a 2.0M solution in heptane/THF/ethylbenzene) was added dropwise to a stirred solution of 5-methoxyindan-1-one tert-butyloxycarbonylhydrazone (5.0 g) in tetrahydrofuran (150 ml) at −78° C. under nitrogen with stirring. After the addition was complete the mixture was stirred for 1.5 hours at −78° C. and then a solution of ethyl thiophen-2-carboxylate (3.39 g) in tetrahydrofuran (25 ml) was added dropwise. The mixture was stirred at −78° C. for 1.5 hours and then allowed to warm to ambient temperature. After 30 minutes the reaction mixture was quenched by the addition of saturated ammonium chloride solution and the layers were separated. The aqueous phase was extracted with ether. The combined organic phases were washed with 2M hydrochloric acid, dried, filtered and evaporated to give a residue which was dissolved in dichloromethane (100 ml) and trifluoroacetic acid (0.35 ml) was added. The mixture was stirred under a nitrogen atmosphere at ambient temperature and then purified by flash column chromatography using ethyl acetate/petroleum ether b.p 60–80° C. (4:1) as the mobile phase to give 6-methoxy-2-tert-butyloxycarbonyl-3-(2-thienyl)-1,4-dihydroindeno[1,2-c]pyrazole.

b) A solution of boron tribromide in dichloromethane (1.35 ml of a 1M solution) was added with stirring to a solution of the product from a) (100 mg) in dichloromethane (5 ml) at −78° C. under a nitrogen atmosphere. The mixture was stirred for 2 hours at −78° C. and then the mixture was allowed to warm up to ambient temperature slowly and stirred at this temperature for 18 hours. The mixture was quenched with water and the organic layer was separated. The aqueous layer was extracted with dichloromethane and the combined organic extracts were washed with brine, dried, filtered and evaporated to give 3-(2-thienyl)-1,4-dihydroindeno[1,2-c]pyrazol-6-ol, m.p. >300° C.

Example 27 a) Triethylamine (0.48 ml) was added to a solution of 4-(1,4-dihydroindeno[1,2-c]pyrazol-3-yl)aniline (400 mg) in dichloromethane (20 ml) with stirring under nitrogen at ambient temperature followed by benzoyl chloride (0.4 ml). The mixture was stirred for 3 hours and then allowed to stand for 18 hours. The mixture was filtered to give 4'-(1-benzoyl-1,4-dihydroindeno[1,2-c]pyrazol-3-yl)benzanilide, m.p. 241° C.

b) The product from a) (0.35 g) was dissolved in methanol (20 ml) and 2M sodium hydroxide solution (3.85 ml) was added. The mixture was stirred at 20° C. for 2 hours and then the solid was collected by filtration and dried in vacuum at 60° C. for 2 hours to give 4'-(1,4-dihydroindeno[1,2-c]pyrazol-3-yl)-benzanilide hydrate, m.p. 273–274° C.

Example 28 a) Methyl thiosalicylate (2.0 g) was added dropwise to a stirred solution of sodium methoxide (1.28 g) in methanol (50 ml) at ambient temperature. The mixture was stirred at ambient temperature for 15 minutes and then a solution of 2-(bromoacetyl)thiophene (2.26 g) in methanol (50 ml) was added dropwise. After the addition was complete the mixture was boiled under reflux for 3 hours, then cooled, and 10% aqueous hydrochloric acid (100 ml) was added. A solid was collected by filtration, dried and then recrystallized from ethanol to give 2-thenoylbenzo[b]thiophene-3-ol.

b) A mixture of the product from a) (500 mg), hydrazine hydrate (106 mg) and n-butanol (5 ml) was boiled under reflux under nitrogen for 7 hours. The mixture was concentrated under vacuum to give a gum which was crystallized from ethyl acetate/petroleum ether, b.p. 60–80° C., to give a solid which was purified by flash column chromatography on silica using ethyl acetate/petroleum ether, b.p. 60–80° C. (3:7) as the mobile phase. Appropriate fractions were collected and evaporated to give 3-(2-thienyl)-1H-benzothieno[3,2-c]pyrazole, m.p. 236–238° C.

Example 29

A mixture of methyl 4-(1,4-dihydroindeno[1,2-c]pyrazol-3-yl)benzoate (0.3 g) and N,N-diethylethylenediamine (1 ml) was heated at 150° C. for 3.5 hours and then at 180° C. for 2 hours. The mixture was cooled and dissolved in industrial methylated spirit and this solution was preabsorbed onto silica which was applied to the top of a flash column. The column was eluted with dichloromethane/industrial methylated spirit/triethylamine (25:2:1) to give a solid which was stirred with water for 1 hour, filtered and dried under vacuum at 60° C. to give N-(2-diethylaminoethyl)-4-(1,4-dihydroindeno[1,2-c]pyrazol-3-yl)benzamide, m.p. 172–174° C.

Example 30

A mixture of 4-(1-oxoindan-2-ylidenemethyl)phenol (1.67 g, Chem. Ber. 1901, 34, 413), p-toluenesulphonyl hydrazine (1.95 g), p-toluenesulphonic acid (0.27 g) and ethanol (15 ml) was boiled under reflux for 72 hours. The solvent was removed under reduced pressure and the residue was purified by flash column chromatography on silica using petroleum ether, b.p. 60–80° C./ethyl acetate (1:1) as the mobile phase. Appropriate fractions were collected, combined and evaporated to give a residue which was triturated with petroleum ether, b.p. 60–80° C., to give a solid which was crystallized from ethanol to give 4-(1,4-dihydroindeno[1,2-c]pyrazol-3-yl)phenol, m.p. 266–268° C.

Example 31

A mixture of 3-(1,4-dihydroindeno[1,2-c]pyrazol-3-yl)phenol (0.29 g), ethylene carbonate (0.11 g), a trace of solid sodium hydroxide (spatula tip of 20–40 mesh beads) and dry dimethylformamide (3 ml) was stirred under nitrogen and heated at 100° C. for 45 minutes. The external temperature was raised to 140° C. and the mixture heated at this temperature for 3.5 hours. The reaction mixture was cooled and diluted with ethyl acetate and the mixture washed with dilute aqueous sodium hydroxide solution and then with water. The organic phase was dried, filtered and evaporated to give a residue which was purified by flash column chromatography on silica using ethyl acetate as the mobile phase. Appropriate fractions were collected, combined and evaporated to give a solid with was triturated with diethyl ether and filtered to give 2-[3-(1,4-dihydroindeno[1,2-c]pyrazol-3-yl)phenoxy]ethanol, m.p. 203–205° C.

Example 32

A mixture of 4-(1,4-dihydroindeno[1,2-c]pyrazol-3-yl)benzoic acid (0.37 g), dichloromethane (20 ml) and oxalyl chloride (0.26 ml) was stirred at 15–20° C. and then dimethylformamide (3 drops) was added. The mixture was stirred at 15–20° C. for 30 minutes and then warmed at 40° C. for 1 hour. The solvent was removed under reduced pressure to give a solid which was dissolved in dichloromethane (20 ml) and then aniline (0.13 ml) and triethylamine (0.38 ml) were added. The mixture was stirred at ambient temperature under nitrogen for 2 hours and then washed with water, dried, filtered and evaporated to give a solid which was purified by flash column chromatography on silica to give 4-(1,4-dihydroindeno[1,2-c]pyrazol-3-yl)benzanilide, m.p. 186–190° C.

Example 33

A mixture of 3-(1,4-dihydroindeno-[1,2-c]pyrazol-3-yl)phenol (2.4 g), anhydrous potassium carbonate (1.2 g), ethyl 2-bromoacetate (1.2 ml) and dry dimethylformamide (20 ml) was stirred at ambient temperature for 24 hours. The mixture was diluted with dichloromethane (200 ml), washed with water, then 1N sodium hydroxide solution. The organic layer was separated, dried, filtered and evaporated to give an oil which was purified by flash column chromatography on silica using ethyl acetate/petroleum ether b.p. 60–80° C. (1:2 as the mobile phase). Appropriate fractions were combined and evaporated to give ethyl 3-(1,4-dihydroindeno[1,2-c]pyrazol-3-yl)phenoxyacetate, m.p. 134–136° C.

Example 34

A mixture of ethyl 3-(1,4-dihydroindeno[1,2-c]pyrazol-3-yl)phenoxyacetate (0.66 g), 1M sodium hydroxide solution (4 ml) and ethanol (20 ml) was heated on a steam bath for 30 minutes. The solvent was removed under reduced pressure and the residue was stirred for 1 hour with 1M hydrochloric acid (20 ml) at ambient temperature. The mixture was filtered to give 3-(1,4-dihydroindeno[1,2-c]pyrazol-3-yl)phenoxyacetic acid, m.p. 246–248° C.

Example 35

In a similar manner to example 33, a mixture of 3-(1,4-dihydroindeno-[1,2-c]pyrazol-3-yl)phenol (0.20 g) was reacted with ethyl 4-bromobutyrate (0.16 g) to give ethyl 4-[3-(1,4-dihydroindeno-[1,2-c]pyrazol-3-yl)phenoxy]butyrate, m.p. 142–148° C.

Example 36

In a similar manner to example 34, ethyl 4-[3-(1,4-dihydroindeno-[1,2-c]pyrazol-3-yl)phenoxy]butyrate (0.36 g) was reacted with 1M sodium hydroxide solution (5 ml) in ethanol (10 ml) to give 4-[3-(1,4-dihydroindeno[1,2-c] pyrazol-3-yl)phenoxy]butyric acid, m.p. 216–217° C.

Example 37

A mixture of 4-[3-(1,4-dihydroindeno[1,2-c]pyrazol-3-yl) phenoxy]butyric acid (0.24 g) was stirred in dry tetrahydrofuran (5 ml) at ambient temperature and triethylamine (0.20 ml) was added. The mixture was stirred at ambient temperature for 15 minutes then cooled in an ice bath and then methyl chloroformate (0.2 ml) was added. The mixture was stirred at ice bath temperature for 1 hour and then concentrated ammonia solution (SG 0.880, 5 ml) was added dropwise by pipette. The mixture was stirred at 0° C. for 5 minutes and then evaporated to dryness under reduced pressure. The residue was purified by flash column chromatography on silica using dichloromethane/IMS/ triethylamine (8:1:1) as the mobile phase. Appropriate fractions were combined and evaporated to give 4-[3-(1,4-dihydroindeno[1,2-c]pyrazol-3-yl)phenoxy]butyramide, m.p. 200–202° C.

Example 38 a) Chloroacetyl chloride (0.3 g) was added to a mixture of 4-(1,4-dihydroindeno[1,2-c]pyrazol-3-yl)aniline (0.6 g), dichloromethane (20 ml) and triethylamine (0.27 g) at 0° C. with stirring under nitrogen. Further triethylamine (0.37 ml) and chloroacetyl chloride (0.21 ml) were added and the mixture was stirred for a further hour. The mixture was filtered and washed with water to give 4'-(1-chloroacetyl-1,4-dihydroindeno[1,2-c] pyrazol-3-yl)chloroacetanilide.

b) A mixture of 4'-(1-chloroacetyl-1,4-dihydroindeno[1, 2-c]pyrazol-3-yl)chloroacetanilide (0.7 g), tetrahydrofuran (40 ml) and morpholine (0.61 g) was boiled under reflux under nitrogen for 5 hours. Potassium carbonate (0.97 g) was added and the mixture was boiled under reflux for a further hour. The mixture was poured into water and extracted with ethyl acetate to give 4'-(1,4-dihydroindeno[1,2-c]pyrazol-3-yl) morpholinoacetanilide, m.p. 291–292° C.

Example 39

A mixture of 4-(1,4-dihydroindeno[1,2-c]pyrazol-yl) benzoyl chloride [(500 mg) prepared by reaction of the product of Example 8 (1.45 g) with oxalyl chloride (1.5 ml) in dichloromethane (100 ml) and DMF (8 drops) followed by evaporation of the solvent], dichloromethane (50 ml), 2-morpholinoethanol (0.22 ml) and triethylamine (0.5 ml) was stirred at ambient temperature for 3.5 hours. The mixture was washed with water then with saturated sodium bicarbonate solution, then dried, filtered and evaporated to give an oil which was purified by flash column chromatography on silica using dichloromethane/IMS (10:1) as the mobile phase to give an oil which was purified again by flash column chromatography using dichloromethane/IMS (25:1) as the mobile phase to give the product 2-morpholinoethyl 4-(1,4-dihydroindeno[1,2-c]pyrazol-3-yl)- benzoate as a solid, m.p. 168–172° C.

Example 40

A mixture of methyl 4-(1,4-dihydroindeno[1,2-c]pyrazol-3-yl]benzoate (2.2 g, Example 7) and N,N-diethylethylenediamine (7 ml) was boiled under reflux for 5 hours. The mixture was cooled and stood for 16 hours at ambient temperature. Petroleum ether, b.p. 60–80° C. (50 ml) was added and then decanted off to leave a gum which was further treated with petroleum ether as above and the residual gum dissolved in dichloromethane and purified by flash column chromatography on silica using dichloromethane/IMS/triethylamine (25:2:1) as the mobile phase to give a solid which was dissolved in ethanol (70 ml) and then dry hydrogen chloride gas was passed through the solution. The precipated solid was collected by filtration, washed with ethanol and dried to give N-(2-diethylaminoethyl)-4-(1,4-dihydroindeno[1,2-c]-pyrazol-3-yl)- benzamide dihydrochloride, m.p.230° C.

Examples 41–50

Step 1

A 1:1 mixture (by volume) of dichloromethane:methanol (1 ml) was added via a Gilson 215 liquid handler, to the starting enone (approx. 50 mg, see Table A) in a septum sealed tube, followed by aqueous 2M sodium hydroxide solution (1 molar equivalent, see Table A) followed by 100 volumes aqueous hydrogen peroxide (1.8 molar equivalents). The resulting solutions/suspensions were then shaken at ambient temperature for 20 hours. Following LCMS analysis, further 100 volumes aqueous hydrogen peroxide (1.8 molar equivalents) was added to each reaction tube, this time manually via a plastic-tipped pipette. To those tubes containing a significant quantity of insoluble material was also added further 1:1 (by volume) dichloromethane:methanol (1 ml). Shaking was then continued for a further 24 hours.

All reactions were analysed by t.l.c. and to those judged to have given incomplete reaction was added further 100 volumes aqueous hydrogen peroxide (1.8 molar equivalents) again via a plastic-tipped pipette (see those reactions indicated by ×3 in Table A). These reaction mixtures were stirred at ambient temperature for 3 days.

The reaction solutions/suspensions were equilibrated between dichloromethane (approx. 5 ml) and water (approx. 2 ml), filtering off the organic phase through an Empore® filter cartridge and washing through with dichloromethane (approx. 2 ml). The dichloromethane phases were evaporated and the residues further dried in vacuo.

TABLE A

| Starting enone (mg) | 2N aq. NaOH ($\mu$l) | 100 volumes aq. H$_2$O$_2$ ($\mu$l) |
| --- | --- | --- |
| 41 2-(3-Nitrobenzylidene)-1-indanone (49.7 mg) | 93.7 | 38.3 × 3 |
| 42 2-(4-Thiomethoxybenzylidene)-1-indanone (50.2 mg) | 94.2 | 38.5 × 2 |
| 43 2-(2-Naphthylmethylene)-1-indanone (51.3 mg) | 94.9 | 38.8 × 2 |
| 44 2-(4-Difluoromethoxybenzylidene)-1-indanone (51.3 mg) | 89.6 | 36.7 × 2 |
| 45 2-(4-Acetamidobenzylidene)-1-tetralone (50.5 mg) | 86.7 | 35.5 × 3 |
| 46 2-(4-Bromo-2-thienylmethylene)-1-indanone (50.9 mg) | 83.4 | 34.1 × 2 |
| 47 2-(4-Benzyloxybenzylidene)-1-tetralone (50.7 mg) | 74.5 | 30.5 × 2 |
| 48 5,6-Dimethoxy-2-(3-phenoxybenzylidene)-1-indanone (50.2 mg) | 67.4 | 27.6 × 3 |
| 49 2-[4-(5-Trifluoromethyl-2-pyridyloxy)benzylidene]-1-indanone (50.2 mg) | 65.8 | 26.9 × 2 |

TABLE A-continued

| Starting enone (mg) | 2N aq. NaOH (μl) | 100 volumes aq. H$_2$O$_2$ (μl) |
|---|---|---|
| 50 5,6,7-Trimethoxy-2-(2,3,4 trimethoxybenzylidene)-1-indanone (50.0 mg) | 62.4 | 25.5 × 3 |

The step 1 products were taken on on the basis of being the corresponding 2,3-epoxyketones.

Step 2

To the products from step 1 in a septum sealed tube was added, via a Gilson 215 liquid handler, n-butanol (2 ml) followed by hydrazine hydrate (2 molar equivalents based on amount of starting enone used in step 1) as a 10% solution by volume in n-butanol (see Table B). To each tube was finally added glacial acetic acid (2 drops) manually by syringe. The reactions were heated at 100° C. with shaking for the times indicated in Table B, based on monitoring by t.l.c. analysis. Reaction mixtures were evaporated to dryness and the residues were purified by chromatography on silica eluting with ethyl acetate, diluted where necessary with petroleum ether, b.p. 40–60° C. Appropriate fractions were evaporated and dried in vacuo. Where necessary, products were further purified by preparative HPLC (see Table B) to give the final pyrazoles. The products were analysed by LCMS and the conditions are given later.

TABLE B

Reaction Details

| Example | Volume of 10% NH$_2$NH$_2$.H$_2$O μl | Heating time at 100° C. | Further purification of product by prep. HPLC |
|---|---|---|---|
| 41 | 182.5 | 6 h | Yes |
| 42 | 183.6 | 6 h | No |
| 43 | 184.8 | 22 h | No |
| 44 | 174.5 | 6 h | No |
| 45 | 168.8 | 38 h | Yes |
| 46 | 162.4 | 22 h | No |
| 47 | 145.1 | 38 h | No |
| 48 | 131.3 | 22 h | No |
| 40 | 128.2 | 6 h | No |
| 50 | 121.6 | 22 h | No |

Yields/LCMS

| Example | MF | MWt | M$^+$ found | HPLC RT (min) | Final Mass |
|---|---|---|---|---|---|
| 41 | C$_{16}$H$_{11}$N$_3$O$_2$ | 277 | Yes | 4.67 | 3.5 mg |
| 42 | C$_{17}$H$_{14}$N$_2$S | 278 | Yes | 4.94 | 5.3 mg |
| 43 | C$_{20}$H$_{14}$N$_2$ | 282 | Yes | 5.29 | 21.9 mg |
| 44 | C$_{17}$H$_{12}$F$_2$N$_2$O | 298 | Yes | 4.82 | 21.2 mg |
| 45 | C$_{19}$H$_{17}$N$_3$O | 303 | Yes | 3.67 | 5.0 mg |
| 46 | C$_{14}$H$_9$BrN$_2$S | 317 | Yes | 5.16 | 10.2 mg |
| 47 | C$_{24}$H$_{20}$N$_2$O | 352 | Yes | 5.93 | 2.7 mg |
| 48 | C$_{24}$H$_{20}$N$_2$O$_3$ | 384 | Yes | 5.16 | 16.3 mg |
| 49 | C$_{22}$H$_{14}$F$_3$N$_3$O | 393 | Yes | 5.56 | 20.1 mg |
| 50 | C$_{22}$H$_{24}$N$_2$O$_6$ | 412 | Yes | 4.25 | 11.9 mg |

Example 41

3-(3-Nitrophenyl)-1,4-dihydroindeno[1,2-c]pyrazole

Example 42

3-(4-Thiomethoxyphenyl)-1,4-dihydroindeno[1,2-c]pyrazole

Example 43

3-(2-Naphthyl)-1,4-dihydroindeno[1,2-c]pyrazole

Example 44

3-(4-Difluoromethoxyphenyl)-1,4-dihydroindeno[1,2-c]pyrazole

Example 45

3-(4-Acetamidophenyl)-4,5-dihydro-2H-benz[g]indazole

Example 46

3-(4-Bromo-2-thienyl)-4,5-dihydroindeno[1,2-c]pyrazole

Example 47

3-(4-Benzyloxyphenyl)-4,5-dihydro-2H-benz[g]indazole

Example 48

6,7-Dimethoxy-3-(3-phenoxyphenyl)-1,4-dihydroindeno[1,2-c]pyrazole

Example 49

3-[4-(5-Trifluoromethyl-2-pyridyloxy)phenyl]-1,4-dihydroindeno[1,2-c]pyrazole

Example 50

6,7,8-Trimethoxy-3-(2,3,4-trimethoxyphenyl)-1,4-dihydroindeno[1,2-c]pyrazole

| LC | |
|---|---|
| Column: | 5 HYPERSIL BDS C18 (100 × 2.1 mm) |
| Mobile Phase: | 0.1% Formic Acid: MeCN (gradient - see below) |
| Conditions: (gradient) | 10–100% MeCN in 8 minutes |
| | 100% MeCN for 1 minute |
| | 100–10% MeCN in 2 minutes |
| | (Total analysis run time 11 minutes) |
| Flow Rate: | 1 ml/min |
| Wavelength Range: | 206–320 nm |
| Injection Volume: | 10 μl |
| MS | |
| Ionization | APcI +ve/−ve |
| Mass Range: | 150–500 m/z |
| Cone Voltage: | 20 |

Example 51 a) A mixture of 4-hydroxy-3-(hydroxymethyl) benzaldehyde (1.08 g), indan-1-one (0.94 g), ethanol (30 ml) and 5M aqueous sodium hydroxide solution (1.6 ml) was boiled under reflux for 6.5 hours. The mixture was cooled to ambient temperature and allowed to stand at that temperature for 16 hours. The mixture was diluted with water (45 ml) and then with 5M hydrochloric acid (1.6 ml) which was added with cooling. The precipitate formed was collected by filtration, washed with water and dried to give 2-(4-hydroxy-3-(hydroxymethyl)benzylidene)-1-indan-one, m.p. 194–195° C.

b) A mixture of the product from a) (0.85 g), p-toluenesulphonylhydrazine (0.9 g), p-toluenesulphonic acid (0.12 g) and ethanol (15 ml) was boiled under reflux for 4.5 hours. The solvent was removed under reduced pressure at ambient temperature and the residue was partitioned between dichloromethane and aqueous sodium bicarbonate solution. The organic layer was separated, washed with water and the dichloromethane was removed by pipette from a gum. The gum was purified by flash column chromatography on silica using 10% and the 20% IMS in dichloromethane as a mobile phase. Appropriate factions were collected, combined and evaporated to give a solid which was triturated with diethyl ether to give 4-(1,4-dihydroindeno[1,2-c]pyrazol-3-yl)-2-hydroxymethyl)phenol, m.p. >300° C.

Examples 52–55

The following examples were prepared in a similar manner to Example 51 by reacting indan-1-one with the appropriate aldehyde;

Example 52

2-Methoxy-5-(1,4-dihydroindeno[1,2-c]pyrazol-3-yl) phenol, m.p. 189–199° C., prepared from 3-hydroxy-4-methoxybenzaldehyde.

Example 53

2-Chloro-4-(1,4-dihydroindeno[1,2-c]pyrazol-3-yl) phenol, m.p. 235–236° C., prepared from 3-chloro-4-hydroxybenzaldehyde.

Example 54

2-Methoxy-4-(1,4-dihydroindeno[1,2-c]pyrazol-3-yl) phenol, m.p. 243–244° C., prepared from 4-hydroxy-3-methoxybenzaldehyde.

Example 55

3-Chloro-4-(1,4-dihydroindeno[1,2-c]pyrazol-3-yl) phenol, m.p. 231–233° C., prepared from 2-chloro-4-hydroxybenzaldehyde.

Example 56

A mixture of 4-(1,4-dihydroindeno[1,2-c]pyrazol-3-yl) phenol (0.28 g, Example 30), potassium carbonate (0.16 g) and 2-bromoacetamide (0.16 g) was stirred together at ambient temperature in dry dimethyl formamide (5 ml) for 4 days and then allowed to stand at ambient temperature for 9 days. The mixture was diluted with dichloromethane (50 ml) and washed with 1M aqueous sodium hydroxide solution and then with water. Some insoluble material which remained throughout the extractions was collected by filtration. The solid was purified by flash column chromatography on silica using ethyl acetate as the mobile phase. Appropriate fractions were collected, combined and evaporated to give 2-[4-(1,4-dihydroindeno[1,2-c]pyrazol-3-yl)phenoxy] acetamide, m.p. 247–248° C.

Example 57

A mixture of 4'-(1-chloroacetyl-1,4-dihydroindeno[1,2-c] pyrazol-3-yl)chloro-acetanilide (1.0 g) in THF (40 ml), diethylamine (0.73 g) and potassium carbonate (1.38 g) was boiled under reflux for 6 hours and then cooled to 20° C. and stood at this temperature for 16 hours. The mixture was poured into water/ethyl acetate (50 ml of each) and the organic layer was separated, dried and evaporated to give an oily solid which was purified by flash column chromatography on silica using 5% methanol in dichloromethane as the mobile phase and then rechromatographed using ethyl acetate as the mobile phase followed by 5% methanol in dichloromethane. Appropriate fractions were collected, combined and evaporated to give 4'-(1,4-dihydroindeno[1, 2-c]pyrazol-3-yl)diethylamino-acetanilide, m.p. 99–100° C.

Example 58 a) A mixture of 4-cyanophenacyl bromide (3.0 g), methyl thiosalicylate (2.25 g), sodium methoxide (1.52 g) and ethanol (100 ml) was boiled under reflux for 3.5 hours. The mixture was cooled and diluted with 2M hydrochloric acid (100 ml). A precipitate was collected by filtration and recrystallized from ethanol to give 2-(4-cyanobenzoyl)-3-hydroxybenzo[b]thiophene.

b) Hydrazine hydrate (5 ml) was added to a solution of the product from a) (2.0) in ethanol (100 ml) containing glacial acetic acid (1 drop) over 4 Å molecular sieves (5 g). The mixture was boiled under reflux for 24 hours and then filtered. The filtrate was concentrated under reduced pressure and the residue obtained was purified by flash column chromatography on silica using diethyl ether/petroleum ether, b.p. 60–80° C. (1:1) as the mobile phase to give a solid which was recrystallized from ethanol/water to give 4-(1H-[1]benzothieno[3,2-c]pyrazol-3-yl)benzamide, m.p. 290–292° C. (with decomposition).

Example 59

In a similar manner to Example 58, a mixture of methyl thiosalicylate (2.76 g), 4-nitrophenacyl bromide (4.0 g), sodium methoxide (1.94 g) and ethanol (200 ml) gave 2-(4-nitrobenzoyl)-3-hydroxybenzo[b]thiophene of which 2.25 g was reacted with hydrazine hydrate (6 ml) in a similar manner to Example 58, to give 3-(4-aminophenyl)-1H-[1] benzothieno[3,2-c]pyrazole, m.p. 113–115° C.

Example 60

In a similar manner to Example 58, 4-methoxyphenacyl bromide (0.81 g) was reacted with methylthiosalicylate (5.0 g) in sodium methoxide and methanol to give 2-(4-methoxybenzoyl)-3-hydroxy[b]thiophene which was reacted with hydrazine hydrate to give 3-(4-methoxyphenyl)-1H-benzothieno[3,2-c]pyrazole, m.p. 185–187° C.

Example 61

Boron tribromide (3.0 ml of a 1.0M solution in dichloromethane) was added to a solution of the product from Example 60 (210 mg) in dichloromethane (10 ml) at −78° C. under nitrogen with stirring. The mixture was allowed to warm to ambient temperature slowly, and after stirring at this temperature for 2 days the mixture was quenched by the addition of aqueous ammonium chloride solution. The organic layer was separated, dried and evaporated to give a residue which was purified by flash column chromatography on silica using dichloromethane and then increasing amounts of methanol, up to 15% of methanol, in dichloromethane as the mobile phase. Appropriate fractions were collected, combined and evaporated to give 3-(4-hydroxyphenyl)-1H-[1]benzothieno[3,2-c]pyrazole, m.p. 137–1 39° C.

Example 62

5-Aminoindan-1-one (2.5 g) was reacted with benzoyl chloride (2.63 g) in dichloromethane and triethylamine to give 5-benzamidoindan-1-one which was reacted with benzaldehyde in a similar manner to Example 7a) to give N-(2-benzylidene-1-oxoindan-5-yl)benzamide which was reacted with hydrogen peroxide in a similar manner to Example 7b) to give an intermediate which was reacted with hydrazine hydrate in a similar manner to Example 7c) to give -(3N-phenyl-1,4-dihydroindeno[1,2-c]pyrazol-6-yl) benzamide, m.p. 271° C., after chromatography of the reaction mixture.

Example 63

4-(1,4-Dihydroindeno[1,2-c]pyrazol-3-yl)phenol was stirred with water (20 ml) containing 2M aqueous sodium hydroxide solution (0.41 ml). The suspension was warmed gently and then stirred at ambient temperature for 1.5 hours and then ethanol (20 ml) was added to give almost complete solution. The solvent was removed under reduced pressure and the residue was dried under vacuum. The solid was triturated with diethyl ether (10 ml) and filtered to give 4-(1,4-dihydroindeno[1,2-c]pyrazol-3-yl)phenol sodium salt, m.p. >300° C.

The compounds shown in Tables 1, 2 and 3 were prepared in a similar manner to Example 7b and 7c. Alternatively these compounds are prepared in a similar manner to Example 30.

Example 64

A mixture of methyl 4-(1,4-dihydroindeno[1,2-c]pyrazol-3-yl)benzoate (100 mg) and N-(2-aminoethyl)morpholine (0.5 ml) was stirred and heated at 150° C. for 5 hours. The mixture was cooled and washed with petroleum ether, b.p. 40–60° C. (20 ml). The mixture was dissolved in a mixture of dichloromethane/IMS/triethyl-amine (25:2:1) and purified by flash column chromatography on silica using the same solvent mixture as the mobile phase. Appropriate fractions were collected, combined and evaporated to give a gum which was dissolved in dichloromethane, washed with water, then dried, filtered and evaporated to give a solid which was triturated with ether and filtered to give N-(2-morpholinoethyl)-4-(1,4-dihydroindeno[1,2-c]pyrazol-3-yl) benzamide monohydrate, m.p. 210–214° C.

Example 65

In a similar manner to Example 7a, indan-1-one was reacted with 4-cyanobenzaldehyde and the intermediate product obtained was reacted with hydrogen peroxide in a similar manner to Example 7b to give an intermediate spiro compound which was reacted with hydrazine hydrate in a similar manner to Example 7c to give 4-(1,4-dihydroindeno [1,2-c]pyrazol-3-yl)benzonitrile, m.p. 245° C.

Example 66

6-Methoxy-2-(4-thiomethoxybenzylidene)-1-tetralone was reacted with hydrogen peroxide and then with hydrazine hydrate following the general procedure described for examples 41–50 to give 7-methoxy-3-(4-methylsulphonylphenyl)-4,5-dihydro-2H-benz[g]indazole ($C_{19}H_{18}N_2O_3S$ MWt 354, M$^+$ found, percentage purity by HPLC 66%).

Example 67

3-Phenylindeno[1,2-c]pyrazol-4-(1H)-one (2.4 g) was suspended in toluene (40 ml) under nitrogen and trimethyl aluminium (2.2 ml of a 2M solution in heptane) was added at 20° C. with stirring. The mixture was heated at 90° C. for 16 hours, then cooled to ambient temperature and poured on to crushed ice (approx. 600 ml) containing concentrated hydrochloric acid (30 ml). The precipitated solid was collected by filtration and recrystallized from ethyl acetate with hot filtering to give 4-methyl-3-phenyl-1,4-dihydroindeno [1,2-c]pyrazol-4-ol, m.p.154–155° C.

Example 68

Dihydroxy 4-(4H-indeno-[1,2-c]-pyrazol-3-yl) phenylborane

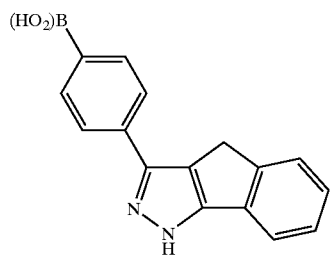

A solution of 3-(4-bromophenyl)-4H-indeno[1,2-c] pyrazole (2.0 g, 6.43 mmol) in dry THF (50 ml) was added to a stirred suspension of potassium hydride (35% wt dispersion in mineral oil, 0.365 g, 6.75 mmol) in dry THF (50 ml) in an atmosphere of nitrogen. After 10 mins the mixture was cooled to about −78° C. and tert-butyl lithium (1.5M solution in pentane, 8.78 ml, 13.18 mmol) was added and the mixture stirred for about 15 mins. A solution of tri-isopropylborate in THF (1.56 ml, 6.75 mmol) was added to the red solution and the mixture was allowed to warm up to room temp and stirred overnight. Hydrochloric acid (1M, 150 ml) was added and the solution stirred for about 30 mins and extracted with ether (3×200 ml). The combined ether extracts were then extracted with sodium hydroxide (3×100 ml). The combined alkaline extracts were acidified with hydrochloric acid (2M) and the precipitated off solid was filtered and dried at the pump to give dihydroxy 4-(4H-indeno-[1,2-c]pyrazol-3-yl)phenylborane (602 mg, 34%). Mpt >300° C.

Example 69

4-(1H-[1]Benzothieno[3,2-c]pyrazol-3-yl) benzaldehyde

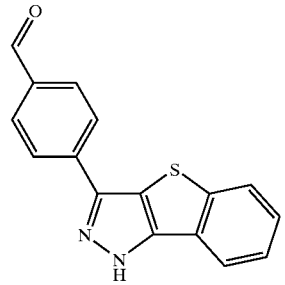

A solution of 3-(4-bromophenyl)-1H-[1]benzothieno[3,2-c]pyrazole (4.0 g, 12.2 mmol) in dry THF (200 ml) was added dropwise to a stirred suspension of potassium hydride (35% wt dispersion in mineral oil, 1.53 g 13.4 mmol) in an atmosphere of nitrogen, maintaining the temp at about 0° C. After complete addition, the reaction mixture was stirred for about 15 mins at about 0° C. then cooled to about −78° C. Tert-butyl lithium (1.5M solution in pentane, 17 ml, 25.62 mmol) was then added dropwise and the mixture stirred for about 45 mins. Dry DMF (61 mmol) was then added dropwise, maintaining the temp at about −78° C. The resulting mixture was stirred at this temp for about 1 hr, allowed to warm to room temp and stirred overnight. The reaction mixture was quenched by careful addition of hydrochloric acid (1M, 200 ml) and the two layers separated. The aqueous layer was extracted with ether (2×200 ml). The combined extracts and the organic layer were washed with saturated sodium bicarbonate (1×200 ml), water (3×200 ml) dried (MgSO₄), filtered and the solvent was removed to give a waxy red solid (1.3 g) which was purified by flash chromatography (eluting with 20% ethyl acetate/80% 60–80 petroleum ether) to give 4-(1H-[1]benzothieno[3,2-c] pyrazol-3-yl)benzaldehyde (200 mg, 6%). Mpt 261–3° C.

Example 70

4-(1H-[1]Benzothieno[3,2-c]pyrazol-3-yl)-N-[3-(imidazol-1-yl)propyl]benzylamine trihydrochloride

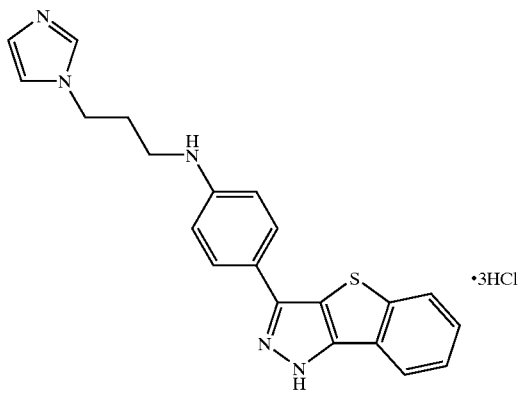

A solution of 4-(1H-[1]benzothieno[3,2-c]pyrazol-3-yl) benzaldehyde (0.1 g 0.36 mmol), 3-(imidazol-1-yl) propylamine (0.058 g, 0.47 mmol) and glacial acetic acid (0.03 ml, 0.47 mmol) in 1,2-dichloroethane was stirred at room temp for about 1 hr. Solid sodium triacetoxyborohydride (0.084 g, 0.4 mmol) was then added in one portion and the resulting mixture stirred for about 16 hrs at room temp. An additional portion of sodium triacetoxyborohydride (0.084 g, 0.4 mmol) was added and the mixture stirred for another 24 hrs. The reaction mixture was poured onto a solution of saturated sodium bicarbonate (20 ml) and stirred for about 30 mins, the layers separated and the aqueous layer extracted with dichloromethane (2×50 ml). The combined extracts and organic layer were washed with water (1×25 ml), dried (MgSO₄), filtered and concentrated in vacuo to give a waxy solid which was taken up in ethanol. Two drops of hydrochloric acid (conc) were added, the solution cooled and scratched to give a solid which was removed by filtration, dried in vacuo to give 4-(1H-[1]benzothieno[3,2-c]pyrazol-3-yl)-N-[3-(imidazol-1-yl)propyl]benzylamine trihydrochloride (0.09 g, 50%) Mpt 206–208° C.

Example 71

Methyl 4-(4-oxo-1,4-dihydroindeno[1,2-c]pyrazol-3-yl)benzoate

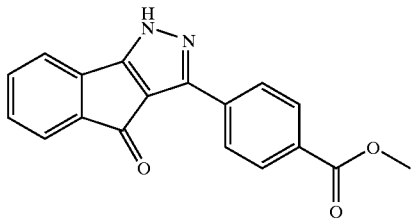

A mixture of methyl 4-(1,4-dihydroindeno[1,2-c]pyrazol-3-yl)benzoate (6.3 g, Example 7), sodium bismuthate (31 g), glacial acetic acid (180 ml) and water (60 ml) was boiled under reflux for about 3.5 hours. A further amount of sodium bismuthate (33 g) was added and the mixture boiled under reflux for about 24 hours, then cooled. The pH of the reaction mixture was adjusted to 8–9 by addition of saturated sodium bicarbonate solution. The reaction mixture was filtered through a celite pad and the residue solid washed with ethyl acetate. The organic layer was separated, dried, filtered and evaporated to give a brown solid. The solid was boiled up in methanol (50 ml), cooled and the solid was filtered off, then dried to give methyl 4-(4-oxo-1,4-dihydroindeno[1,2-c]pyrazol-3-yl)benzoate, m.p. dec. 235° C.

Example 72

4-(1,4-dihydroindeno[1,2-c]pyrazol-3-yl)benzamide oxime

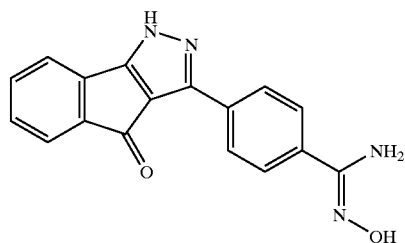

A mixture of 4-(1,4-dihydroindeno[1,2-c]pyrazol-3-yl) benzonitrile (730 mg, Example 65), hydroxylamine hydrochloride (0.4 g), sodium carbonate (0.8 g) and ethanol (30 ml) was boiled under reflux for about 16 hours. The solvent was removed under reduced pressure at about 50° C. and the residue stirred with water (70 ml). The mixture was extracted with ethyl acetate and the combined organic phases dried, filtered and evaporated to give a solid. The solid was purified by flash column chromatography on silica using ethyl acetate as eluant to give a solid which was washed with diethyl ether and dried to give 4-(1,4-dihydroindeno[1,2-c]pyrazol-3-yl)benzamide oxime, m.p.>300° C.

Example 73

3-{4-[(2-diethylaminoethyl)aminomethyl]phenyl}-1,4-dihydroindeno [1,2-c]pyrazole trihydrochloride

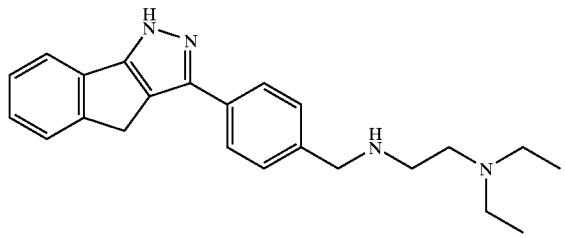

A mixture of N-(2-diethylaminoethyl)-4-(1,4-dihydroindeno[1,2-c]pyrazol-3-yl)benzamide (2.75 g, Example 29) and dry tetrahydrofuran (100 ml) was stirred at room temperature under nitrogen and lithium aluminium hydride (3.4 g) was added portionwise. The reaction mixture was then boiled under reflux for about 2.5 hours, then cooled in an ice/water bath. Ethyl acetate (100 ml) and water (100 ml) were added. Then the organic phase was separated off, washed with brine (25 ml), dried, filtered and evaporated to give a yellow oil. The oil was purified by flash column chromatography on silica using ethyl acetate/ ethanol/ triethylamine (7:2:1) as eluant to give a pale yellow gum. The gum was dissolved in warm ethanol (5 ml), hydrochloric acid (conc, 0.6 ml) was added and the solvent then removed under reduced pressure. The gummy solid residue was boiled up with ethanol (10 ml) and cooled in ice. The precipitated solid was collected by filtration, washed with ethanol and dried to give 3-{4-[(2-diethylaminoethyl)aminomethyl]phenyl}-1,4-dihydroindeno[1,2-c]pyrazole trihydrochloride, m.p. 225° C.

Example 74

N-[4-(1,4-Dihydroindeno[1,2-c]pyrazol-3-yl)phenyl]benzenesulphonamide

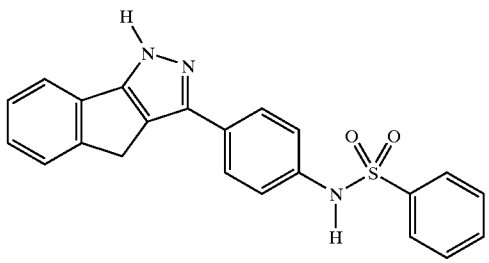

a) 4'-(1,4-Dihydroindeno[1,2-c]pyrazol-3-yl)aniline (1 g) was dissolved in dichloromethane (30 ml) and triethylamine (0.62 ml) was added. The reaction mixture was then cooled to about 0° C. and benzenesulphonyl chloride (0.57 ml) added dropwise over 5 minutes. The reaction mixture was then warmed to ambient temperature and stirred for about 2 hours. A further addition of benzenesulphonyl chloride (0.57 ml) and triethylamine (0.62 ml) was made and stirring continued for about another 4 hours at ambient temperature. Diethyl ether (80 ml) and water (40 ml) was then added. A solid precipitated which was filtered and washed with an aqueous solution of sodium bicarbonate (40 ml) and diethyl ether (40 ml). The solid was further purified by flash chromatography over silica using dichloromethane as eluant. Early fractions were combined and solvent removed in vacuo to give N-[4-(1-benzenesulphonyl-1,4-dihydroindeno [1,2-c]pyrazol-3-yl)phenyl]benzenesulphonamide as a brown solid (0.35 g) m.p. 251–252° C., later fractions gave as a brown solid (0.76 g) m.p. 267–268° C.

b) N-[4-(1-benzenesulphonyl-1,4-dihydroindeno[1,2-c]pyrazol-3-yl) phenyl]benzenesulphonamide (0.56 g) was suspended in methanol (40 ml) and a 2N aqueous solution of sodium hydroxide (5.3 ml) added at ambient temperature. A clear solution was obtained. The reaction mixture was stirred at ambient temperature for about 20 minutes and then poured onto a 2N aqueous solution of hydrochloric acid (75 ml). A colourless solid precipitated, which was collected by filtration (0.42 g). The solid was partitioned between an aqueous solution of sodium bicarbonate (25 ml) and ethyl acetate (25 ml), and stirred for about 30 minutes at ambient temperature. It was then collected by filtration and dried in vacuo at about 60° C. to give N-[4-(1,4-dihydroindeno[1,2-c]pyrazol-3-yl)phenyl] benzenesulphonamide as a colourless solid (0.14 g) m.p. 286–288° C.

Example 75

N-(2-Morpholinoethyl)-4'-dihydroindeno[1,2-c]pyrazol]-3-ylaniline dihydrochloride

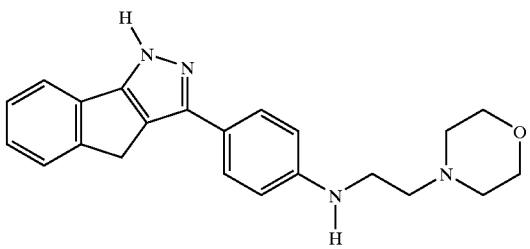

4'-(1,4-Dihydroindeno[1,2-c]pyrazol-3-yl) morpholinoacetamide (1.5 g, Example 38) was dissolved in tetrahydrofuran (80 ml) at ambient temperature under nitrogen and lithium aluminium hydride (0.6 g) was added portionwise over 10 minutes. The mixture was stirred at ambient temperature for about 6 hours, then poured onto a saturated aqueous solution of sodium sulphate (75 ml) and extracted with diethyl ether (2×75 ml). The combined organic extracts were dried (NaSO$_4$) and evaporated in vacuo to give a yellow oil (2.24 g) which was purified by flash chromatography over silica using a gradient of a 1:20 to 1:4 mixture of methanol and dichloromethane as eluant. Appropriate fractions were combined and evaporated in vacuo to give a yellow solid (0.83 g). The solid was dissolved in ethanol (10 ml) and concentrated hydrochloric acid (0.5 ml) was added. A colourless solid precipitated which was collected by filtration to give N-(2-morpholinoethyl)-4'-dihydroindeno[1,2-c]pyrazol-3-ylaniline dihydrochloride (0.94 g) m.p. 284–285° C.

Example 76

N-(1,4-Dihydroindeno[1,2-c]pyrazol-6-yl)-2-morpholinoacetamide

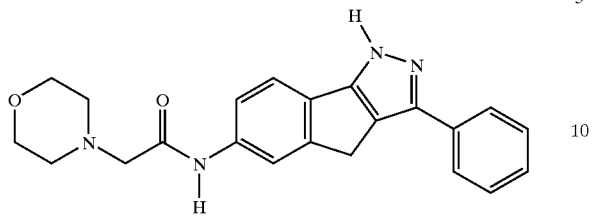

a) 3-Phenyl-1,4-dihydroindeno[1,2-c]pyrazol-6-ylamine (2.0 g) was dissolved in dichloromethane (70 ml) and triethylamine (2.3 ml) was added. The resultant mixture was cooled to about 0° C. and chloroacetyl chloride (1.3 ml) added. The reaction mixture was then stirred at ambient temperature for 10 hours under nitrogen. A colourless solid precipitated which was collected by filtration and dried in vacuo at about 60° C., to give N-(1-chloroacetyl-3-phenyl-1,4-dihydroindeno[1,2-c]pyrazol-6-yl)-2-chloroacetamide (2.04 g) used in the next stage without further purification.

b) N-(1-chloroacetyl-3-phenyl-1,4-dihydroindeno[1,2-c]pyrazol-6-yl)-2-chloroacetamide (1.0 g) was dissolved in tetrahydrofuran (30 ml) and morpholine (0.87 ml) added. The mixture was then heated under reflux for about 90 minutes, cooled to ambient temperature and poured onto water (100 ml). A solid precipitated which was collected by filtration and dried in vacuo at about 60° C., to give N-(1,4-dihydroindeno[1,2-c]pyrazol-6-yl)-2-morpholinoacetamide as a brown solid (0.87 g) m.p. 141–148° C.

Example 77

N-(2-Morpholinoethyl)-3-phenyl-1,4-dihydroindeno[1,2-c]pyrazol-6-ylamine trihydrochloride

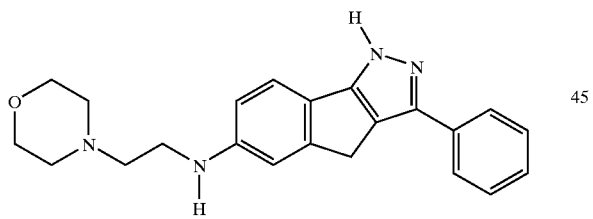

N-(3-Phenyl-1,4-dihydroindeno[1,2-c]pyrazol-6-yl)-2-morpholinoacetamide (0.6 g) was dissolved in tetrahydrofuran (40 ml) at ambient temperature under nitrogen and lithium aluminium hydride (0.24 g) added portionwise over about 10 minutes. The mixture was stirred at ambient temperature for about 24 hours. A further addition of lithium aluminium hydride (0.24 g) was added and the mixture was stirred at ambient temperature for about another 24 hours. It was then poured onto a saturated aqueous solution of sodium sulphate (30 ml) and extracted with diethyl ether (2×30 ml). The combined organic extracts were combined, dried ($Na_2SO_4$) and evaporated in vacuo to give a yellow oil which was purified by flash chromatography over silica using a 1:20 mixture of methanol and dichloromethane as eluant. Appropriate fractions were combined and evaporated in vacuo to give a yellow solid. The solid was dissolved in ethanol (5 ml) and concentrated hydrochloric acid (10 drops) was added. A colourless solid precipitated was collected by filtration to give N-(2-morpholinoethyl)-3-phenyl-1,4-dihydroindeno[1,2-c]pyrazol-6-ylamine trihydrochloride salt (0.18 g) m.p. 180–182° C.

Example 78

4'-(1-Acetyl-1,4-dihydroindeno[1,2-c]pyrazol-3-yl)acetanilide

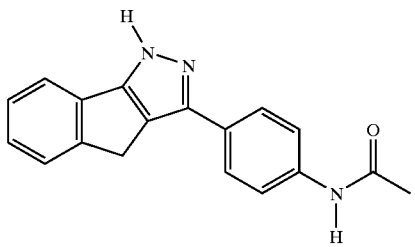

a) 4'-(1,4-Dihydroindeno[1,2-c]pyrazol-3-yl)aniline (1 g) was dissolved in dichloromethane (40 ml) and triethylamine (1.14 ml) was added followed by acetic anhydride (0.85 ml). The reaction mixture was then stirred at ambient temperature for 2 hours under nitrogen. A colourless solid precipitated which was collected by filtration and washed with water and dried in vacuo at about 60° C., to give 4'-(1-acetyl-1,4-dihydroindeno[1,2-c]pyrazol-3-yl)acetanilide as a colourless solid (0.84 g) m.p. 245–246° C.

b) 4'-(1-acetyl-1,4-dihydroindeno[1,2-c]pyrazol-3-yl)acetanilide (1.0 g) was suspended in methanol (40 ml) and a 2N aqueous solution of sodium hydroxide (15 ml) added. The mixture was stirred at ambient temperature for about 20 minutes and then poured onto an aqueous solution of 2N hydrochloric acid (75 ml), a colourless solid precipitated which was collected by filtration and dried in vacuo at about 60° C. to give 4'-(1,4-dihydroindeno[1,2-c]pyrazol-3-yl)acetanilide dihydrochloride (0.96 g) m.p. 295–304° C.

Example 79

3-[4-(2-morpholinoethoxy)phenyl]-1,4-dihydroindeno[1,2-c]pyrazole

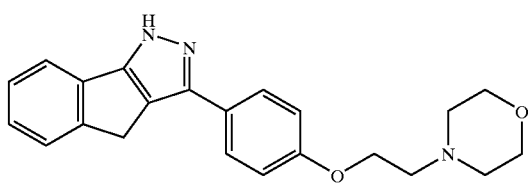

A mixture of 4-(1,4-dihydroindeno[1,2-c]pyrazol-3-yl)phenol (0.76 g, Example 30) 4-(2-hydroxyethyl)morpholine (0.85 g), triphenylphosphine (1.77 g) and dichloromethane (20 ml) were stirred together with ice/water bath cooling and diethylazodicarboxylate (1.16 g) was added dropwise. The resultant mixture was allowed to warm to room temperature and stirred for about 24 hours. The solvent was evaporated off under reduced pressure and the residue purified by flash column chromatography on silica using ethyl acetate/ethanol (25%) to give a solid. The solid was triturated with diethyl ether (10 ml) and the solid filtered, washed with diether and dried at about 65° C. to give 3-[4-(2-morpholinoethoxy)phenyl]-1,4-dihydroindeno[1,2-c]pyrazole, m.p. 175–6° C.

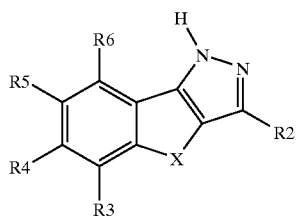

| EX # | R2 | X | R3, R4, R5, R6 | Preparation Comments | Melt Point °C. |
|---|---|---|---|---|---|
| 80 | 4-(Ph)PHENYL | CH$_2$ | H | Prep as Ex 51 | 245–6 |
| 81 | 4-(OPh)PHENYL | CH$_2$ | H | Prep as Ex 7 | 195–6 |
| 82 | 4-(SO$_2$Me)PHENYL | (CH$_2$)$_2$ | R4 = MeO | Prep as Ex 66 | |
| 83 | 3-(CO$_2$H),4-(OH)PHENYL | CH$_2$ | H | Prep as Ex 51 | 283–4 |
| 84 | 3-(NO$_2$),4-(OH)PHENYL | CH$_2$ | H | Prep as Ex 51 | 250–2 |
| 85 | 3-(OCH$_2$CONH$_2$)PHENYL | CH$_2$ | H | Prep as Ex 56 | 246–8 |
| 86 | 4-(OCH$_2$Ph)PHENYL | CH$_2$ | R4, R5 = (MeO)$_2$ | Prep as Ex 51 | 110–4 |
| 87 | 4-(OCH$_2$Ph)PHENYL | CH$_2$ | R5 = MeO | Prep as Ex 51 | 228–31 |
| 88 | 4-(OH)PHENYL | CH$_2$ | R4, R5 = (MeO)$_2$ | Prep as Ex 13 | 250–4 |
| 89 | 3-(CONH(CH$_2$)$_2$MOR)4-(OH))PHENYL | CH$_2$ | H | Prep as Ex 40 | 160 (dec) |
| 90 | 3-(CONH(CH$_2$)$_2$NEt$_2$),4-(OH))PHENYL | CH$_2$ | H | Prep as Ex 40 | 210 (dec) |
| 91 | 4-(Br)PHENYL | CH$_2$ | H | Prep as Ex 7 | 277–9 |
| 92 | 4-(OH)PHENYL | CH$_2$ | R4 = MeO | Prep as Ex 13 | 256–60 |
| 93 | 4-(CONH(CH$_2$)$_3$NEt$_2$)PHENYL | CH$_2$ | H | Prep as Ex 39 | M + 388 |
| 94 | 4-(CONH(CH$_2$)$_2$OMe)PHENYL | CH$_2$ | H | Prep as Ex 39 | M + 333 |
| 95 | 4-(CONH(4-NO$_2$Ph))PHENYL | CH$_2$ | H | Prep as Ex 39 | M + 396 |
| 96 | 4-(OH)PHENYL | CH$_2$ | R5 = MeO | Prep as Ex 51 | 237–40 |
| 97 | 4-(CONH(CH$_2$)$_2$NEt$_2$)PHENYL | CH$_2$ | R4 = NH$_2$ | Prep as Ex 29 | 212–4 |
| 98 | 4-(Br)PHENYL | S | H | Prep as Ex 1-6 | 287–9 |
| 99 | 4-(OH)PHENYL | CH$_2$ | R3 = O(CH$_2$)$_2$OMe | Prep as Ex 51 | 197–8 |
| 100 | 4-(SO$_2$NH(CH$_2$)$_2$MOR)PHENYL | CH$_2$ | H | Prep as Ex 7 | 218–20 |
| 101 | 4-(SO$_2$NH(CH$_2$)$_2$OMe)PHENYL | CH$_2$ | H | Prep as Ex 7 | 184–6 |
| 102 | 3-(CH$_2$NMe$_2$),4-(OH)PHENYL | CH$_2$ | H | Prep as Ex 51 | 183–7 |
| 103 | 4-(OH)PHENYL | CH$_2$ | R3 = O(CH$_2$)$_2$MOR | Prep as Ex 51 | 280 (dec) |
| 104 | 4-(SO$_2$NH(CH$_2$)$_2$NEt$_2$)PHENYL | CH$_2$ | H | Prep as Ex 7 | 192–6 |
| 105 | 4-(OCH$_2$CONH$_2$)PHENYL | CH$_2$ | R3 = O(CH$_2$)$_2$OMe | Prep as Ex 56 | 234–6 |
| 106 | 4-(OH)PHENYL | CH$_2$ | R4 = (OH), R5 = O(CH$_2$)$_2$OMe | Prep as Ex 51 | 96–100 |
| 107 | 4-(OH)PHENYL | CH$_2$ | R4 = O(CH$_2$)$_2$OMe | Prep as Ex 51 | 75–81 |
| 108 | 4-(CONH(CH$_2$)$_2$NHEt)PHENYL | CH$_2$ | H | Prep as Ex 40 | 230 |
| 109 | 4-(CONHCH$_2$-2-PYRR)PHENYL | CH$_2$ | H | Prep as Ex 40 | 222–6 |
| 110 | 4-(OCH$_2$CONH$_2$)PHENYL | CH$_2$ | R3 = OH | Prep as Ex 51 | 220 |
| 111 | 4-(OCH$_2$CO$_2$H)PHENYL | CH$_2$ | H | Prep as Ex 34 | 250–3 |

Example 112

3-[2-(2H-1,2,3,4-Tetraazol-5-yl)-4-pyridyl]-4,5-dihydro-2H-benzo[g]indazole 4-(4,5-Dihydro-2H-benzo[g]indazol-3-yl)-2-pyridinecarbonitrile (50 mg, 0.184 mmoL) was dissolved in 5 mL of THF. To this was added 900 mg (15 eq) of tributyltinazide. The reaction mixture was heated for about 24 hours and the progress of the reaction was followed by HPLC. Some starting material still remained at this point; the reaction was allowed to cool to room temperature. The solvent was removed under reduced pressure. The residue was dissolved in dichloromethane (5 mL) and to this was added excess 1N HCl. A precipitate formed which was filtered and dried to give 33 mg of a white solid. HPLC/MS confirmed product formation: MH+ 316.2, retention time: 1.73 min Experimentals for Examples 113–159

Tricyclic pyrazoles, ureas and carbamates.

LC conditions (analytical run):

Column: PECOSPHERE, C18, 3 µm, 33 × 4.6 mm
Gradient: From 100% pH 4.5, 50 mM NH$_4$OAc/H$_2$O to 100% CH$_3$CN -continued in 4.5 minutes
Flow rate: 3.5 mL/min
LC/MS purification conditions:

Column: Hypersil ® BDS, C18, 5°, 100 × 21.2 mm
Gradient: Generally from 100% pH 4.5, 50 mM NH$_4$OAc/H$_2$O to 100% CH$_3$CN in 8.5 minutes but varied depending upon required separation.
Flow rate: 25 mL/min Melting Points Were recorded on an Electrothermal 9100 melting point microscope in open capillaries and are uncorrected.

IR

IR spectra were recorded on a Hewlett Packard Nicolete Impact 400 FT-IR spectrophotometer using KBr pellets. Only the strongest and most significant bands are reported.

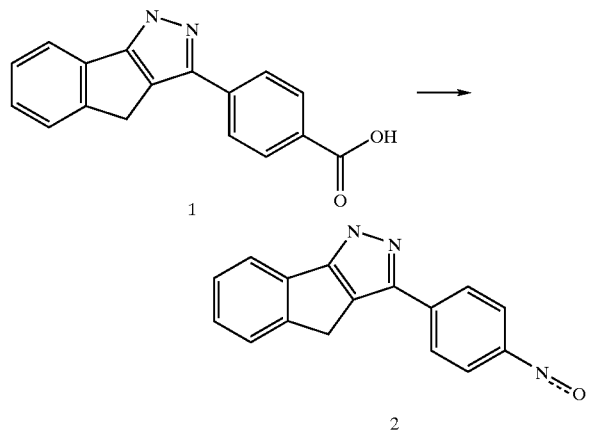

3-(4-Isocyanatophenyl)-1,4-dihydroindeno[1,2-c] pyrazole, 2

To a solution of 4-(1,4-dihydroindeno[1,2-c]pyrazol-3-yl) benzoic acid 1 (5.8 g, 20.99 mmol) in DMF (200 mL) were added diphenylphosphoryl azide (5.22 mL, 23.09 mmol) and Et$_3$N (3.35 mL, 23.09 mmol). The reaction mixture was heated to about 80° C., for about 4 h, until no more N$_2$ gas evolution was observed. The off-white precipitation was filtered off and washed with EtOAc (3×5 mL) and Et$_2$O (3×5 mL). The solid was dried under vacuum to give quantitative yield of 2 that was used in the next step without further purification. Mp 338–339° C. IR (KBr) 2132, 1723,1582, 1520

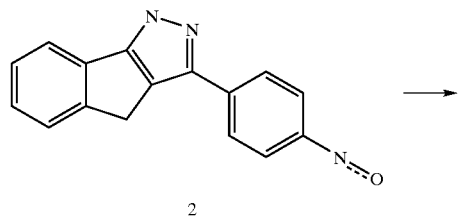

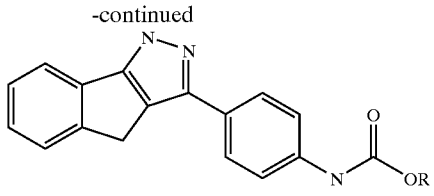

Examples 113–121

General procedure for O-substituted N-[4-(1,4-dihydroindeno[1,2-c]pyrazol-3-yl)phenyl] carbamates To a solution of an appropriate alcohol in THF was added NaH (12 eq.) and the reaction mixture was stirred for about 45 min. at about 20° C. Solid 3-(4-isocyanatophenyl)-1,4-dihydroindeno[1,2-c]pyrazole, 2 was added. The reaction mixture was stirred for about 3 hours at about 45° C. 2 M HCl was added until pH=7 and the crude material was extracted into EtOAc. Purification by flash chromatography (CH$_2$Cl$_2$/MeOH) gave the pure carbamate 3.

Example 113

2-(Diethylamino)ethyl N-[4-(1,4-dihydroindeno[1,2-c]pyrazol-3-yl)phenyl]carbamate To a solution of N,N-diethyl ethanol amine (0.368 mL, 2.75 mmol) in THF (5 mL) was added NaH (60% in mineral oil, 113 mg, 2.75 mmol). The reaction mixture was stirred at about 20° C., for about 1 hour then solid 3-(4-isocyanatophenyl)-1,4-dihydroindeno[1,2-c]pyrazole, 2 (58 mg, 0.22 mmol) was added. The reaction mixture was heated to about 45° C., for about 3 hours. The reaction mixture was quenched by addition of H$_2$O and the product was extracted into EtOAc. The crude material was purified by flash chromatography on SiO$_2$ (MeOH/CH$_2$Cl$_2$, 10/90) to give 51 mg (62%) of pure product. LC/MS 391 (M+1); LC retention time 2.68 minutes.

Example 114

2-Morpholinoethyl N-[4-(1,4-dihydroindeno[1,2-c]pyrazol-3-yl)phenyl]carbamate 56 mg (66%) of pure product was isolated. LC/MS 405 (M+1); LC retention time 2.69 minutes.

Example 115

3-(Dibenzylamino)propyl N-[4-(1,4-dihydroindeno[1,2-c]pyrazol-3-yl)phenyl]carbamate 34 mg (35%) of pure product was isolated. LC/MS 530 (M+1); LC retention time 4.18 minutes.

Example 116

2-[Ethyl(2-hydroxyethyl)amino]ethyl N-[4-(1,4-dihydroindeno[1,2-c]pyrazol-3-yl)phenyl]carbamate acetate salt 19 mg (26%) of pure product was isolated. LC/MS 407 (M+1); LC retention time 2.65 minutes.

Example 117

2-[[2-(Dimethylamino)ethyl](methyl)amino]ethyl N-[4-(1,4-dihydroindeno[1,2-c]pyrazol-3-yl)phenyl] carbamate acetate salt 32 mg (42%) of pure product was isolated. LC/MS 420 (M+1); LC retention time 2.80 minutes.

Example 118

1-Methyl-2-propoxyethyl N-[4-(1,4-dihydroindeno[1,2-c]pyrazol-3-yl)phenyl]carbamate 42 mg (59%) of pure product was isolated. LC/MS 392 (M+1); LC retention time 3.60 minutes.

Example 119

2-(1-Methyltetrahydro-1H-2-pyrrolyl)ethyl N-[4-(1,4-dihydroindeno[1,2-c]pyrazol-3-yl)phenyl]carbamate 4 mg (7%) of pure product was isolated. LC/MS 403 (M+1); LC retention time 2.81 minutes.

Example 120

2-[2-(Dimethylamino)ethoxy]ethyl N-[4-(1,4-dihydroindeno[1,2-c]pyrazol-3-yl)phenyl]carbamate acetate salt 32 mg (43%) of pure product was isolated. LC/MS 407 (M+1); LC retention time 2.62 minutes.

Example 121

2-(Diethylamino)-1-methylethyl N-[4-(1,4-dihydroindeno[1,2-c]pyrazol-3-yl)phenyl]carbamate acetate salt 7 mg (9%) of pure product was isolated. LC/MS 405 (M+1); LC retention time 2.84 minutes.

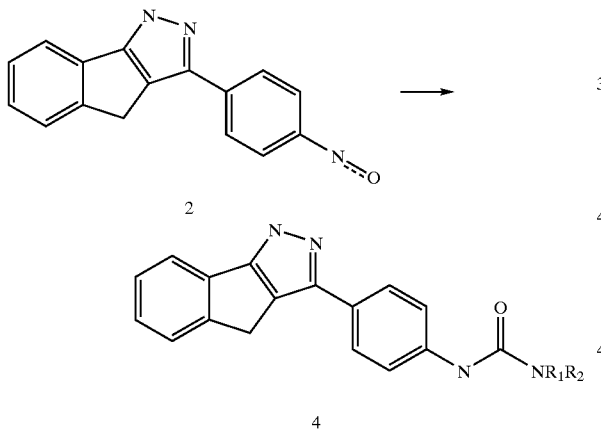

Examples 122–159

General procedures for N-substituted N-[4-(1,4-dihydroindeno[1,2-c]pyrazol-3-yl)phenyl]ureas 4

To a suspension of 3-(4-isocyanatophenyl)-1,4-dihydroindeno[1,2-c]pyrazole, 2, in toluene was added $Et_3N$ (5 eq.) and an appropriate amine (5 eq.). The reaction mixture was stirred at about 95° C., for 0.5 to 5 hours. The solid was filtered off and washed with EtOAc and $Et_2O$ and dried in vacuum to give the desired urea 4.

Example 122

N-[2-(Diethylamino)ethyl]-N'-[4-(1,4-dihydroindeno[1,2-c]pyrazol-3-yl)phenyl]urea A suspension of of 3-(4-isocyanatophenyl)-1,4-dihydroindeno[1,2-c]pyrazole, 2 (75 mg, 0.274 mmol), $Et_3N$ (0.191 mL, 1.37 mmol), N,N-diethylethylenediamine (0.112 mL, 1.37 mmol) in toluene (3 mL) was heated to about 95° C., for about 3 hours. The white solid was filtered off and washed with EtOAc and dried under vacuum to afford 61 mg (57%) of pure product. LC/MS 390 (M+1); LC retention time 2.76 minutes.

Example 123

N-[4-(1,4-Dihydroindeno[1,2-c]pyrazol-3-yl)phenyl]-N'-(2-morpholinoethyl)urea 84 mg (76%) of pure product was isolated. LC/MS 404 (M+1); LC retention time 2.50 minutes.

Example 124

N1-[4-(1,4-Dihydroindeno[1,2-c]pyrazol-3-yl)phenyl]-1-piperidinecarboxamide 32 mg (49%) of pure product was isolated. LC/MS 359 (M+1); LC retention time 3.36 minutes.

Example 125

N-[4-(1,4-Dihydroindeno[1,2-c]pyrazol-3-yl)phenyl]-N'-[2-(dimethylamino)-1-methylethyl]urea 57 mg (55%) of pure product was isolated. LC/MS 376 (M+1); LC retention time 2.72 minutes.

Example 126

N-[4-(1,4-Dihydroindeno[1,2-c]pyrazol-3-yl)phenyl]-N'-tetrahydro-2-furanylmethylurea 57 mg (56%) of pure product was isolated. LC/MS 375 (M+1); LC retention time 2.98 minutes.

Example 127

N-[4-(1,4-Dihydroindeno[1,2-c]pyrazol-3-yl)phenyl]-N'-(2-furylmethyl)urea 66 mg (65%) of pure product was isolated. LC/MS 371 (M+1); LC retention time 3.34 minutes.

Example 128

N-(1,3-Benzodioxol-5-ylmethyl)-N'-[4-(1,4-dihydroindeno[1,2-c]pyrazol-3-yl)phenyl]urea 75 mg (64%) of pure product was isolated. LC/MS 425 (M+1); LC retention time 3.45 minutes.

Example 129

N-Cyclobutyl-N'-[4-(1,4-dihydroindeno[1,2-c]pyrazol-3-yl)phenyl]

60 mg (64%) of pure product was isolated. LC/MS 345 (M+1); LC retention time 3.28 minutes.

Example 130

N-[4-(1,4-Dihydroindeno[1,2-c]pyrazol-3-yl)phenyl]-N'-(2-piperidinoethyl)urea urea 64 mg (58%) of pure product was isolated. LC/MS 402 (M+1); LC retention time 2.84 minutes.

Example 131

N-Benzyl-N'-[4-(1,4-dihydroindeno[1,2-c]pyrazol-3-yl)phenyl]urea 47 mg (45%) of pure product was isolated. LC/MS 381 (M+1); LC retention time 3.40 minutes.

Example 132

N-[4-(Diethylamino)butyl]-N'-[4-(1,4-dihydroindeno[1,2-c]pyrazol-3-yl)phenyl]urea 62 mg (54%) of pure product was isolated. LC/MS 418 (M+1); LC retention time 2.76 minutes.

Example 133

N-[4-(1,4-Dihydroindeno[1,2-c]pyrazol-3-yl)phenyl]-N'-[2-(2-thienyl)ethyl]urea 65 mg (59%) of pure product was isolated. LC/MS 401 (M+1); LC retention time 3.44 minutes.

Example 134

N-[3-(Diethylamino)propyl]-N'-[4-(1,4-dihydroindeno[1,2-c]pyrazol-3-yl)phenyl]urea 50 mg (45%) of pure product was isolated. LC/MS 404 (M+1); LC retention time 2.73 minutes.

Example 135

N-[4-(1,4-Dihydroindeno[1,2-c]pyrazol-3-yl)phenyl]-N'-[(1-ethyltetrahydro-1H-2-pyrrolyl)methyl]urea 53 mg (48%) of pure product was isolated. LC/MS 402 (M+1); LC retention time 2.89 minutes.

Example 136

N-(2,5-Difluorobenzyl)-N'-[4-(1,4-dihydroindeno[1,2-c]pyrazol-3-yl)phenyl]urea 15 mg (13%) of pure product was isolated. LC/MS 417 (M+1); LC retention time 3.50 min.

Example 137

N-[4-(1,4-Dihydroindeno[1,2-c]pyrazol-3-yl)phenyl]-N'-[2-(2-hydroxyethoxy)ethyl]urea 34 mg (33%) of pure product was isolated. LC/MS 379 (M+1); LC retention time 2.66 min.

Example 138

N-[4-(1,4-Dihydroindeno[1,2-c]pyrazol-3-yl)phenyl]-N'-[2-hydroxy-1-(hydroxymethyl)ethyl]urea 4 mg (1%) of pure product was isolated. LC/MS 365 (M+1); LC retention time 2.48 min.

Example 139

N-[4-(1,4-Dihydroindeno[1,2-c]pyrazol-3-yl)phenyl]-N'-(2,3-dihydroxypropyl)urea 8 mg (8%) of pure product was isolated. LC/MS 365 (M+1); LC retention time 2.54 min.

Example 140

N1-[4-(1,4-Dihydroindeno[1,2-c]pyrazol-3-yl)phenyl]-4-(2-pyridyl)-1-piperazinecarboxamide 68 mg (71%) of pure product was isolated. LC/MS 437 (M+1); LC retention time 3.13 minutes.

Example 141

N-[4-(1,4-Dihydroindeno[1,2-c]pyrazol-3-yl)phenyl]-N-[3-(dimethylamino)propyl]-N-methylurea 54 mg (63%) of pure product was isolated. LC/MS 390 (M+1); LC retention time 2.60 minutes.

Example 142

N1-[4-(1,4-Dihydroindeno[1,2-c]pyrazol-3-yl)phenyl]-1-azetanecarboxamide 48 mg (66%) of pure product was isolated. LC/MS 331 (M+1); LC retention time 2.86 minutes.

Example 143

N1-[4-(1,4-Dihydroindeno[1,2-c]pyrazol-3-yl)phenyl]-4-(4-fluorophenyl)-1-piperazinecarboxamide 63 mg (63%) of pure product was isolated. LC/MS 454 (M+1); LC retention time 3.53 minutes.

Example 144

N-Benzyl-N'-[4-(1,4-dihydroindeno[1,2-c]pyrazol-3-yl)phenyl]-N-methylurea 60 mg (69%) of pure product was isolated. LC/MS 395 (M+1); LC retention time 3.41 minutes.

Example 145

N'-[4-(1,4-Dihydroindeno[1,2-c]pyrazol-3-yl)phenyl]-N-ethyl-N-(2-hydroxyethyl)urea 50 mg (63%) of pure product was isolated. LC/MS 363 (M+1); LC retention time 2.78 minutes.

Example 146

N1-[4-(1,4-Dihydroindeno[1,2-c]pyrazol-3-yl)phenyl]-4-(2-methoxyphenyl)-1-piperazinecarboxamide 49 mg (48%) of pure product was isolated. LC/MS 464 (M-1); LC retention time 3.45 minutes.

Example 147

N'-[4-(1,4-Dihydroindeno[1,2-c]pyrazol-3-yl)phenyl]-N-[2-(dimethylamino)ethyl]-N-methylurea 55 mg (67%) of pure product was isolated. LC/MS 376 (M+1); LC retention time 2.48 minutes.

Example 148

N1-[4-(1,4-Dihydroindeno[1,2-c]pyrazol-3-yl)phenyl]-4-methyl-1-piperazinecarboxamide 16 mg (20%) of pure product was isolated. LC/MS 374 (M+1); LC retention time 2.48 minutes.

Example 149

N1-[4-(1,4-Dihydroindeno[1,2-c]pyrazol-3-yl)phenyl]-4-(4-hydroxyphenyl)-1-piperazinecarboxamide 11 mg (11%) of pure product was isolated. LC/MS 452 (M+1); LC retention time 3.04 minutes.

Example 150

N1-[4-(1,4-Dihydroindeno[1,2-c]pyrazol-3-yl)phenyl]-4-[(E)-3-phenyl-2-propenyl]-1-piperazinecarboxamide 47 mg (45%) of pure product was isolated. LC/MS 476 (M+1); LC retention time 3.26 minutes.

Example 151

N1-[4-(1,4-Dihydroindeno[1,2-c]pyrazol-3-yl)phenyl]-4-phenyl-1-piperazinecarboxamide 46 mg (48%) of pure product was isolated. LC/MS 436 (M+1); LC retention time 3.58 minutes.

Example 152

N'-[4-(1,4-Dihydroindeno[1,2-c]pyrazol-3-yl)phenyl]-N,N-di(2-methoxyethyl)urea 31 mg (37%) of pure product was isolated. LC/MS 407 (M+1); LC retention time 3.25 minutes.

Example 153

N'-[4-(1,4-Dihydroindeno[1,2-c]pyrazol-3-yl)phenyl]-N-(2,3-dihydroxypropyl)-N-methylurea 36 mg (43%) of pure product was isolated. LC/MS 379 (M+1); LC retention time 2.62 minutes.

Example 154

N,N-di[2-(Diethylamino)ethyl]-N'-[4-(1,4-dihydroindeno[1,2-c]pyrazol-3-yl)phenyl]urea 50 mg (47%) of pure product was isolated. LC/MS 489 (M+1); LC retention time 2.61 minutes.

Example 155

N-[4-(1,4-Dihydroindeno[1,2-c]pyrazol-3-yl)phenyl]-N-(2-pyridylmethyl)urea 38 mg (45%) of pure product was isolated. LC/MS 382 (M+1); LC retention time 2.85 minutes.

Example 156

N-[4-(1,4-Dihydroindeno[1,2-c]pyrazol-3-yl)phenyl]-N'-(3-pyridylmethyl)urea 26 mg (31%) of pure product was isolated. LC/MS 382 (M+1); LC retention time 2.70 minutes.

Example 157

N-[4-(1,4-Dihydroindeno[1,2-c]pyrazol-3-yl)phenyl]-N-(4-pyridylmethyl)urea 43 mg (51%) of pure product was isolated. LC/MS 382 (M+1); LC retention time 2.69 min.

Example 158

N-[4-(1,4-Dihydroindeno[1,2-c]pyrazol-3-yl)phenyl]-N'-(2-hydroxyethyl)urea 7 mg (8%) of pure product was isolated. LC/MS 335 (M+1); LC retention time 2.57 minutes.

Example 159

N-[4-(1,4-Dihydroindeno[1,2-c]pyrazol-3-yl)phenyl]-N'-[7-(dimethylamino)heptyl]urea 57 mg (48%) of pure product was isolated. LC/MS 432 (M+1); LC retention time 2.85 minutes.

Examples 160–209

Synthesis of the compound

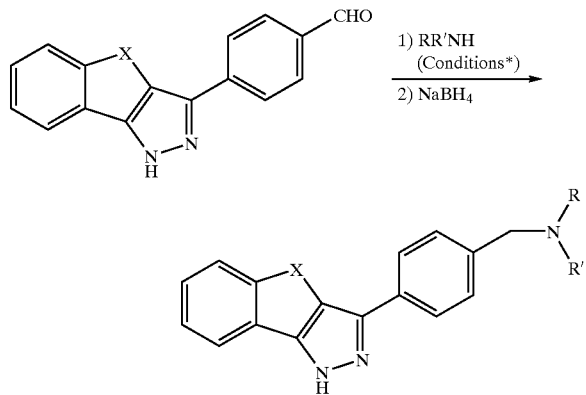

(X=$CH_2$, O, or S)
assay: ca. 85%

| Entry | X | NRR' | Condition | Yield |
|---|---|---|---|---|
| 160 | CH2 | NH n-C12H25 | A | 44% (360 mg) |
| 161 | CH2 | HN-CH2CH2-OMe | A | 78% (480 mg) |
| 162 | CH2 | HN-CH2-CH=CH2 | A | 74% (430 mg) |
| 163 | CH2 | HN-CH2-C≡CH | A | 38% (130 mg) |
| 164 | CH2 | HN-cyclohexyl | A | 73% (480 mg) |
| 165 | CH2 | HN-CH2CH2-piperidinyl | A | 82% (350 mg) |
| 166 | CH2 | HN-CH2CH2-cyclohexenyl | A | 87% (370 mg) |
| 167 | CH2 | HN-tetrazolyl | B | 21% (80 mg) |
| 168 | CH2 | HN-pyrazinyl | B | 77% (300 mg) |

-continued

| Entry | X | NRR' | Condition | Yield |
|---|---|---|---|---|
| 169 | CH2 | 2-amino-1H-imidazole (HN-) | B | 21% (80 mg) |
| 170 | CH2 | (pyridin-2-yl)methylamine | B | 52% (210 mg) |
| 171 | CH2 | (pyridin-3-yl)methylamine | B | 62% (250 mg) |
| 172 | O | HN-CH2CH2-OMe | A | 52% (190 mg) |
| 173 | O | N-methylpiperazine | B | 73% (400 mg) |
| 174 | O | 2-aminopyridine | B | 60% (390 mg) |
| 175 | O | 3-aminopyridine | B | 68% (440 mg) |
| 176 | O | HN-C6H4-NMe2 | B | 62% (440 mg) |
| 177 | O | 3-amino-1,2,4-triazole (HCl) | B | 33% (210 mg) |
| 178 | O | 5-amino-tetrazole | B | 52% (330 mg) |
| 179 | O | (pyridin-4-yl)methylamine | B | 47% (320 mg) |
| 180 | S | HN-CH2CH2-morpholine | A | 61% (430 mg) |
| 181 | S | HN-CH2CH2-NMe2 | A | 30% (130 mg) |
| 182 | S | 2-aminopyridine | B | 58% (370 mg) |
| 183 | S | 3-aminopyridine | B | 66% (420 mg) |

-continued

| Entry | X | NRR' | Condition | Yield |
|---|---|---|---|---|
| 184 | S | 4-aminopyridine | B | 60% (240 mg) |
| 185 | S | (pyridin-4-yl)methylamine | B | 60% (380 mg) |
| 186 | CH2 | NHiso-Pr | A | 62% (360 mg) |
| 187 | CH2 | NHcyc-Pr | A | 50% (290 mg) |
| 188 | CH2 | NHn-Hex | A | 52% (320 mg) |
| 189 | CH2 | (piperidin-4-yl)methylamine | A | 53% (350 mg) |
| 190 | CH2 | piperidine | B | 30% (190 mg) |
| 191 | CH2 | N-methylpiperazine | B | 76% (500 mg) |
| 192 | CH2 | morpholine | B | 56% (360 mg) |
| 193 | CH2 | HN-C6H4-OMe | B | 22% (140 mg) |
| 194 | CH2 | HN-C6H4-OH | B | 53% (360 mg) |
| 195 | CH2 | 2-aminopyridine | B | 71% (460 mg) |
| 196 | CH2 | 3-aminopyridine | B | 54% (350 mg) |
| 197 | CH2 | (pyridin-4-yl)methylamine | A | 64% (430 mg) |
| 198 | CH2 | 3-amino-1,2,4-triazole | B | 48% (300 mg) |
| 199 | CH2 | 2-aminothiazole | B | 51% (340 mg) |

-continued

| Entry | X | NRR' | Condition | Yield |
|---|---|---|---|---|
| 200 | O | piperidine | B | 73% (460 mg) |
| 201 | O | HN-4-pyridyl | B | 5% (430 mg) |
| 202 | O | HN-CH2CH2-NMe2 | A | 5% (350 mg) |
| 203 | O | HN-CH2CH2-morpholine (2HCL) | A | 82% (700 mg) |
| 204 | CH2 | HN-CH2CH2-morpholine (2HCl) | A | 69% (600 mg) |
| 205 | CH2 | piperidine | B | 65% (400 mg) |
| 206 | CH2 | N-methylpiperazine | B | 53% (260 mg) |
| 207 | CH2 | HN-2-pyridyl | B | 35% (180 mg) |
| 208 | CH2 | HN-3-pyridyl | B | 73% (380 mg) |
| 209 | CH2 | HN-CH2-2-pyridyl | B | 63% (340 mg) |

Example A

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidine in ethanol. The dry granulate is blended with the magnesium stearate and the rest of the starch. The mixture is then compressed in a tabletting machine to give tablets each containing a unit dose or a part of a unit dose of active compound.

c) Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognise or be able to ascertain using no more than routine experimentation, many equivalents to the specific embodiments of the invention described specifically herein. Such equivalents are intended to be encompassed in the scope of the claims.

What is claimed is:

1. A compound represented by the formula:

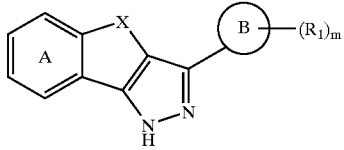

the racemic mixtures, racemic-diastereomeric mixtures, tautomers and optical isomers of said compounds and the pharmaceutically acceptable salts and the prodrugs thereof, wherein:

m is an integer from 1 to 10;

X represents a) an optionally substituted group of the formula —$(CH_2)_n$— in which n is 1, 2 or 3, b) carbonyl, c) oxygen, d) a group of the formula —C=$NOR_{10}$, in which $R_{10}$ is a $C_{1-4}$ alkyl group, e) a group of the formula $NR_{11}$, in which $R_{11}$ is —H, an optionally substituted $C_{1-4}$ alkyl group or an optionally substituted phenyl, or f) a group of formula $S(O)_p$ in which p is 0, 1 or 2;

B represents an alkyl, a cycloalkyl, an aryl, a pyridyl, a thienyl, a furyl or a pyrrolyl;

$R_1$ is —H; a halo; hydroxy; nitro; cyano; hydroxyamidino; aminomethyl; formamidomethyl; an optionally substituted alkenyloxy; an optionally substituted $C_{2-4}$ alkenyl; an optionally substituted $C_{2-4}$ alkynyl; or a group represented by the formula —Y—W, provided that when $R_1$ is —H, an unsubstituted $C_{1-6}$ alkyl, an unsubstituted $C_{1-6}$ alkoxy, a halogen, or trifluoromethyl, then ring A is substituted with at least one substituent that is not a halo, an optionally substituted $C_{1-6}$ alkyl or an optionally substituted $C_{1-6}$ alkoxy;

Y is absent or a $C_{1-6}$ alkyl, $C_{1-6}$ alkoxy, —O—, —S— or —C(O)—;

W is —H, hydroxy, optionally substituted phenyl, $C_{1-6}$ alkoxy, or —$NR_2R_3$;

provided that when B is phenyl and $R_1$ is —Y—W and W is —$NR_2R_3$, then $R_2$ and $R_3$ are each, independently, a) —H; b) a substituted $C_{1-6}$ alkyl group, provided that the substituent is not —$NR_6R_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with —$NR_9(CH_2)_{1-6}OR_4$, —$NR_9(CH_2)_{1-6}CO_2R_4$, —$NR_9(CH_2)_{1-6}NR_4R_5$, or an optionally substituted heterocycloalkyl; or when B is phenyl and $R_1$ is —Y—W and W is —$NR_2R_3$, then $R_2$ and $R_3$, together with the nitrogen atom to which they are attached, can represent an optionally substituted heterocycloalkyl or an optionally substituted heteroaryl;

when B is not phenyl, then $R_2$ and $R_3$ are each, independently, —H, an optionally substituted $C_{1-6}$alkyl group, —$NH(CH_2)_{1-6}NR_4R_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, then $R_2$ and $R_3$ together with the nitrogen atom to which they are attached represent an optionally substituted heterocycloalkyl or an optionally substituted heteroaryl;

$R_4$, $R_5$ and $R_9$ are for each occurrence, independently, —H or a $C_{1-6}$ alkyl; and ring A is optionally substituted with one or more substituents selected from the group consisting of a) a halo; b) a $C_{1-6}$ alkyl group optionally substituted with one or more substituents selected from the group consisting of hydroxy, halo, and —$NR_6R_7$; c) a $C_{1-6}$ alkoxy group optionally substituted with one or more substituents selected from the group consisting of hydroxy, halo, —$NR_6R_7$, an optionally substituted phenyl, and —$NR_{17}C(O)R_{19}$, provided that the substituents are not attached to the carbon which is attached to the oxygen of the alkoxy group; d) an optionally substituted phenoxy; e) hydroxy; f) a group of the formula —C(O)$R_{12}$ in which $R_{12}$ is a hydroxy, a $C_{1-6}$ alkoxy or —$NR_{13}R_{14}$; g) a group of the formula —$NR_{17}R_{18}$; h) a group of the formula —$NR_{17}C(O)R_{19}$; i) nitro; j) optionally substituted aralkyl; k) cyano; and l) a $C_{2-4}$ alkenyl group or a $C_{2-4}$ alkynyl group each of which is optionally substituted with one or more substituents selected from the group consisting of a $C_{1-6}$ alkyl group, a $C_{1-6}$ alkoxy: group and a halo;

$R_6$ and $R_7$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_6$ and $R_7$ together with the nitrogen atom to which they are attached represent an optionally substituted heterocycloalkyl or an optionally substituted heteroaryl;

$R_{13}$ and $R_{14}$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_{13}$ and $R_{14}$ together with the nitrogen atom to which they are attached represent an optionally substituted heterocycloalkyl or an optionally substituted heteroaryl;

$R_{17}$ and $R_{18}$ are each, independently, selected from the group consisting of —H, a $C_{1-12}$ alkyl group, a $C_{3-12}$ cycloalkyl group, and phenyl; and $R_{19}$ is —H, an optionally substituted $C_{1-12}$ alkyl group, an optionally substituted $C_{3-12}$ cycloalkyl group, an optionally substituted phenyl or an optionally substituted aralkyl.

2. A compound of claim 1, wherein B is phenyl.

3. A compound of claim 2, wherein $R_1$ is —Y—W, where Y is —$CH_2$— and W is —$NR_2R_3$.

4. A compound of claim 3, wherein ring A is unsubstituted.

5. A compound of claim 3, wherein X is S or methylene.

6. A compound of claim 3, wherein $R_2$ and $R_3$, taken together with the nitrogen to which they are attached represent an optionally substituted heterocycloalkyl.

7. A compound of claim 6, wherein the optionally substituted heterocycloalkyl formed by —$NR_2R_3$ is selected from the group consisting of a piperizine, a piperidine, homopiperazine, quinuclidine, azetidine, morpholine, thiomorpholine, pyrrolidine, thiazolidine, 8-azabicyclo[3.2.1]octane and 9-azabicyclo[3.3.1]nonane.

8. A compound of claim 7, wherein the optionally substituted heterocycloalkyl formed by —$NR_2R_3$ is substituted with one or more substituents selected from the group consisting of a) a lower alkyl which is optionally substituted with —$NR_4R_5$, —$OR_4$, heterocycloalkyl, or —C(O)$_2R_4$; b) hydroxyl; c) —C(O)$_2R_4$; d) —$NR_4R_5$, wherein $R_4$ and $R_5$ are each, independently, optionally substituted with —$NR_4R_5$, —$OR_4$, heterocycloalkyl or —C(O)$_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —C(O)$_2R_4$; g) —$COR_4$, wherein $R_4$ is optionally substituted with —$NR_4R_5$, —$OR_4$, heterocycloalkyl, or —C(O)$_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

9. A compound of claim 3, wherein $R_2$ is —H and $R_3$ is an optionally substituted heterocycloalkyl.

10. A compound of claim 9, wherein $R_3$ is an optionally substituted heterocycloalkyl selected from the group consisting of a piperizine, a piperidine, homopiperazine, quinuclidine, azetidine, morpholine, thiomorpholine, pyrrolidine, thiazolidine, 8-azabicyclo[3.2.1]octane and 9-azabicyclo[3.3.1]nonane.

11. A compound of claim 10, wherein the optionally substituted heterocycloalkyl defined for $R_3$ is substituted with one or more substituents selected from the group consisting of a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

12. A compound of claim 3, wherein $R_2$ is —H and $R_3$ is an optionally substituted heterocycloalkylalkyl.

13. A compound of claim 12, wherein the optionally substituted heterocycloalkylalkyl defined for $R_3$ has the heterocycloalkyl portion selected from the group consisting of a piperizine, a piperidine, homopiperazine, quinuclidine, azetidine, morpholine, thiomorpholine, pyrrolidine, thiazolidine, 8-azabicyclo[3.2.1]octane and 9-azabicyclo[3.3.1]nonane.

14. A compound of claim 13, wherein the heterocycloalkyl portion of $R_3$ is substituted with one or more substituents selected from the group consisting of a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

15. A compound of claim 3, wherein $R_2$ is —H and $R_3$ is a heteroaryl which is substitute with a —$NR_9(CH_2)_{1-6}OR_4$, a —$NR(CH_2)_{1-6}CO_2R_4$, a —$NR_9(CH_2)_{1-6}NR_4R_5$, or an optionally substituted heterocycloalkyl.

16. A compound of claim 15, wherein the heteroaryl defined for $R_3$ is selected from the group consisting of pyridyl, imidazolyl, furyl, pyrrolyl, thienyl, oxazolyl, thiazolyl, isoxazolyl, thiadiazolyl, oxadiazolyl, pyrimidinyl, pyrazinyl, pyridazinyl, quinolyl, isoquinolyl, indazolyl, benzoxazolyl, benzofuryl, benzothiazolyl, indolizinyl, imidazopyridinyl and benzo(b)thienyl.

17. A compound of claim 16, wherein $R_3$ is pyridinyl.

18. A compound of claim 17, wherein the pyridinyl is substituted with a 2-(N,N-dimethylamino)ethylamino.

19. A compound of claim 3, wherein $R_2$ is —H and $R_3$ is a heteroaralkyl which is substituted with a —$NR_9(CH_2)_{1-6}OR_4$, a —$NR_9(CH_2)_{1-6}CO_2R_4$, a —$NR_9(CH_2)_{1-6}NR_4R_5$, or an optionally substituted heterocycloalkyl.

20. A compound of claim 19, wherein the heteroaralkyl defined for $R_3$ has a heteroaryl which is selected from the group consisting of pyridyl, imidazolyl, furyl, pyrrolyl, thienyl, oxazolyl, thiazolyl, isoxazolyl, thiadiazolyl, oxadiazolyl, pyrimidinyl, pyrazinyl, pyridazinyl, quinolyl, isoquinolyl, indazolyl, benzoxazolyl, benzofuryl, benzothiazolyl, indolizinyl, imidazopyridinyl and benzo(b)thienyl.

21. A compound of claim 20, wherein the heteroaryl portion of $R_3$ is pyridinyl.

22. A compound of claim 21, wherein the pyridinyl is substituted with 2-(N,N-dimethylamino)ethylamino.

23. A compound of claim 2, wherein ring A is substituted with —$CH_2NR_6R_7$.

24. A compound of claim 23, wherein m is 1 and $R_1$ is —H or —F.

25. A compound of claim 24, wherein $R_6$ and $R_7$, taken together with the nitrogen to which they are attached is an optionally substituted heterocycloalkyl.

26. A compound of claim 25, wherein the heterocycloalkyl defined for —$NR_6R_7$ is selected from the group consisting of a piperizine, a piperidine, homopiperazine, quinuclidine, azetidine, morpholine, thiomorpholine, pyrrolidine, thiazolidine, 8-azabicyclo[3.2.1]octane and 9-azabicyclo[3.3.1]nonane.

27. A compound of claim 26, wherein the heterocycloalkyl defined for —$NR_6R_7$ is substituted with one or more substituents selected from the group consisting of a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R$; and i) —$NR_4C(O)R_5$, wherein $R_5$ is optionally substituted with —$OR_4$, —$NR_4R_5$, a heterocycloalkyl which is optionally substituted with a lower alkyl.

28. A compound of claim 23, wherein $R_6$ is —H and $R_7$ is an optionally substituted heterocycloalkyl.

29. A compound of claim 28, wherein $R_7$ is selected from the group consisting of a piperizine, a piperidine, homopiperazine, quinuclidine, azetidine, morpholine, thiomorpholine, pyrrolidine, thiazolidine, 8-azabicyclo[3.2.1]octane and 9-azabicyclo[3.3.1]nonane.

30. A compound of claim 29, wherein $R_7$ is substituted with one or more substituents selected from the group consisting of a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

31. A compound claim 23, wherein $R_6$ is —H and $R_7$ is an optionally substituted heterocycloalkylalkyl.

32. A compound of claim 31, wherein the heterocycloalkyl portion of $R_7$ is selected from the group consisting of a piperizine, a piperidine, homopiperazine, quinuclidine, azetidine, morpholine, thiomorpholine, pyrrolidine, thiazolidine, 8-azabicyclo[3.2.1]octane and 9-azabicyclo[3.3.1]nonane.

33. A compound of claim 32, wherein the heterocycloalkyl portion of $R_7$ is substituted with one or more substituents selected from the group consisting of a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

34. A compound of claim 23, wherein $R_6$ is —H and $R_7$ is an optionally substituted heteroaryl.

35. A compound of claim 34, wherein $R_7$ is selected from the group consisting of pyridyl, imidazolyl, furyl, pyrrolyl, thienyl, oxazolyl, thiazolyl, isoxazolyl, thiadiazolyl, oxadiazolyl, pyrimidinyl, pyrazinyl, pyridazinyl, quinolyl, isoquinolyl, indazolyl, benzoxazolyl, benzofuryl, benzothiazolyl, indolizinyl, imidazopyridinyl and benzo(b)thienyl.

36. A compound of claim 35, wherein $R_7$ is substituted with one or more substituents selected from the group consisting of a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

37. A compound of claim 23, wherein $R_6$ is —H and $R_7$ is an optionally substituted heteroaralkyl.

38. A compound of claim 37, wherein the heteroaryl portion of $R_7$ is selected from the group consisting of pyridyl, imidazolyl, furyl, pyrrolyl, thienyl, oxazolyl, thiazolyl, isoxazolyl, thiadiazolyl, oxadiazolyl, pyrimidinyl, pyrazinyl, pyridazinyl, quinolyl, isoquinolyl, indazolyl, benzoxazolyl, benzofuryl, benzothiazolyl, indolizinyl, imidazopyridinyl and benzo(b)thienyl.

39. A compound of claim 20, wherein the heteroaryl portion of $R_7$ is substituted with one or more substituents selected from the group consisting of a) a lower alkyl which is optionally substituted with —$NR_4R_5$, —$OR_4$, heterocycloalkyl, or —$C(O)_2R_4$; b) hydroxyl; c) —$C(O)_2R_4$; d) —$NR_4R_5$, wherein $R_4$ and $R_5$ are each, independently, optionally substituted with —$NR_4R_5$, —$OR_4$, heterocycloalkyl or —$C(O)_2R_4$; e) heterocycloalkyl which is optionally substituted with a lower alkyl, phenyl, heteroaryl, or heterocycloalkyl which is optionally substituted by a lower alkyl; f) —$OR_4$, wherein $R_4$ is optionally substituted with a —$NR_4R_5$, —$OR_4$, heterocycloalkyl, or —$C(O)_2R_4$; g) —$COR_4$, wherein $R_4$ is optionally substituted with —$NR_4R_5$, —$OR_4$, heterocycloalkyl, or —$C(O)_2R_4$; h) —$NR_4C(O)_2R_5$; and i) —$NR_4C(O)R_5$, wherein $R_5$ is optionally substituted with —$OR_4$, —$NR_4R_5$, a heterocycloalkyl which is optionally substituted with a lower alkyl.

40. A compound of the following structural formula wherein X, $R_2$ and $R_3$ are selected from:

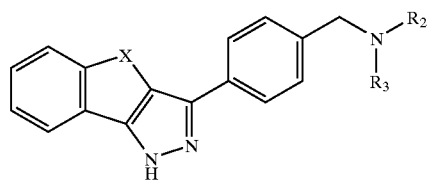

| Entry | X | $NR_2R_3$ |
|---|---|---|
| 1 | $CH_2$ | 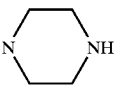 |
| 2 | $CH_2$ | 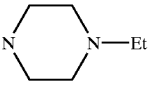 |
| 3 | $CH_2$ | 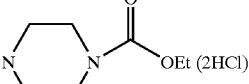 |
| 4 | $CH_2$ | 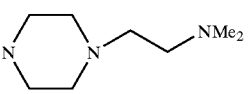 |
| 5 | $CH_2$ |  |
| 6 | $CH_2$ | 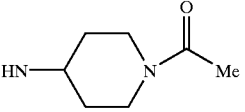 |
| 7 | $CH_2$ | 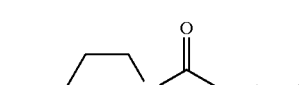 |
| 8 | $CH_2$ | 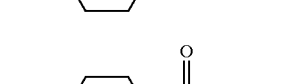 |
| 9 | $CH_2$ | 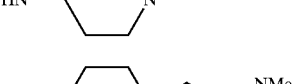 |
| 10 | $CH_2$ | 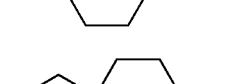 |

-continued
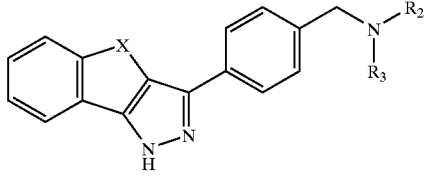
| Entry | X | NR₂R₃ |
|---|---|---|
| 11 | CH₂ | 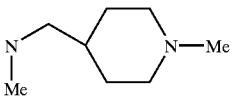 |
| 12 | CH₂ |  |
| 13 | CH₂ | 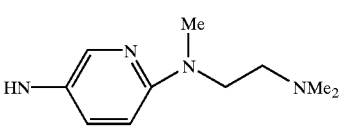 |
| 14 | CH₂ | 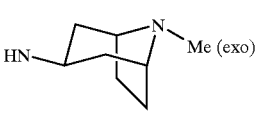 |
| 15 | S | 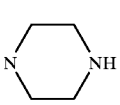 |
| 16 | S | 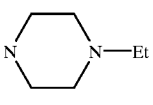 |
| 17 | S | 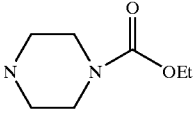 |
| 18 | S | 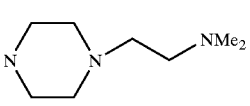 |
| 19 | S | 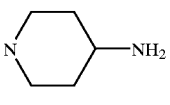 |
| 20 | S | 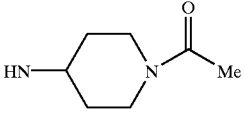 |
| 21 | S | 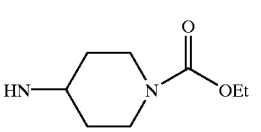 |
-continued
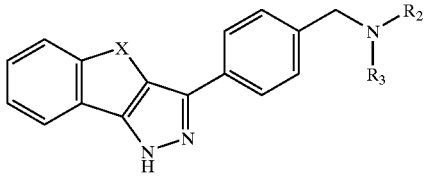
| Entry | X | NR₂R₃ |
|---|---|---|
| 22 | S | 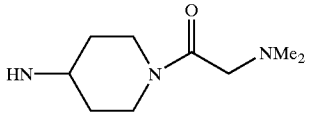 |
| 23 | S | 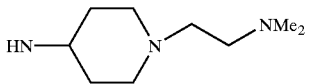 |
| 24 | S | 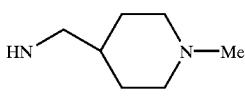 |
| 25 | S | 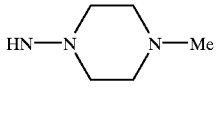 |
| 26 | S |  |
| 27 | S | 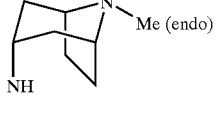 |
| 28 | S |  |
| 29 | S | 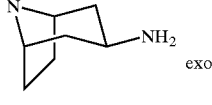 |
| 30 | S | 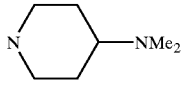 |
| 31 | S | 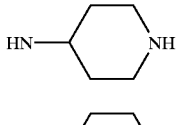 |
| 32 | S | 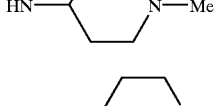 |
| 33 | S | 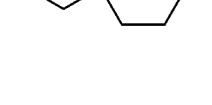 |

-continued

| Entry | X | NR₂R₃ |
|---|---|---|
| 34 | S | HN-pyridine-NH-(CH₂)₃-OMe (5-amino-2-[(3-methoxypropyl)amino]pyridine) |
| 35 | S | HN-pyridine-morpholine |
| 36 | S | HN-pyridine-(N-methylpiperazine) |
| 37 | S | HN-pyridine-NH-CH₂CH₂-NMe₂ |
| 38 | S | HN-CH₂CH₂-morpholine |
| 39 | CH₂ | piperidine |
| 40 | CH₂ | N-methylpiperazine |
| 41 | CH₂ | 2-[(2-dimethylaminoethyl)amino]-3-aminopyridine |
| 42 | CH₂ | HN-pyridine-NH-CH₂CH₂-NMe₂ |
| 43 | CH₂ | 2-piperidinyl-3-aminopyridine |

-continued

| Entry | X | NR₂R₃ |
|---|---|---|
| 44 | CH₂ | HN-pyridine-piperidine |
| 45 | CH₂ | 4-methylpiperidine |
| 46 | CH₂ | NMe₂ (2HCl) |
| 47 | CH₂ | 4-hydroxypiperidine (2HCl) |
| 48 | CH₂ | HN-CH₂-piperidine-N-CH₂CH₂F (3HCl) |
| 49 | S | 2-[(2-dimethylaminoethyl)amino]-3-aminopyridine |
| 50 | S | HN-pyridine-NH-CH₂CH₂-NMe₂ |
| 51 | S | 2-piperidinyl-3-aminopyridine |
| 52 | S | HN-pyridine-piperidine |
| 53 | S | 2-[(2-methoxyethyl)amino]-3-aminopyridine |

-continued

| Entry | X | NR₂R₃ |
|---|---|---|
| 54 | S | piperidine |
| 55 | S | NMe₂ |
| 56 | S | 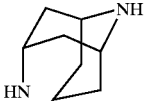 |
| 57 | S | 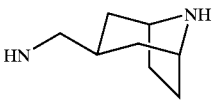 |
| 58 | CO | piperidine |
| 59 | CH₂ | NH₂ |
| 60 | CH₂ | HN-CH₂CH₂-OH |
| 61 | CH₂ |  |
| 62 | CH₂ | 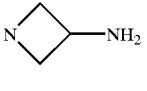 |
| 63 | CH₂ |  (3HCl) |
| 64 | CH₂ | 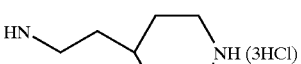 |
| 65 | CH₂ |  |
| 66 | CH₂ | 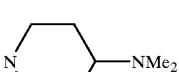 (3HCl) |
| 67 | CH₂ | 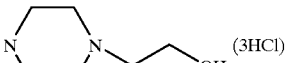 |

-continued

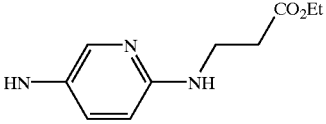

| Entry | X | NR₂R₃ |
|---|---|---|
| 68 | CH₂ | HN-pyridyl-NH-CH₂CH₂-CO₂H |
| 69 | CH₂ | HN-pyridyl-NH-CH₂CH₂CH₂-OH |
| 70 | CH₂ | HN-pyridyl-morpholine |
| 71 | CH₂ | HN-pyridyl-N-methylpiperazine |
| 72 | S | HN-piperidine |
| 73 | S | HN-piperidine-N-Me |
| 74 | S | HN-CH₂CH₂-piperidine (2HCl) |
| 75 | S | piperidine-4-NMe₂ |
| 76 | S | HN-pyridyl-NH-CH₂CH₂CH₂-OH |
| 77 | S | HN-pyridyl-morpholine |
| 78 | S | HN-pyridyl-N-methylpiperazine |
| 79 | CMe₂ | NMe₂ |

-continued

| Entry | X | NR₂R₃ |
|---|---|---|
| 80 | CMe₂ | piperidin-1-yl |
| 81 | SO₂ | HN-CH₂-(piperidin-4-yl)-NH (3HCl) |
| 82 | SO₂ | piperidin-1-yl |
| 83 | S | HN-CH₂-(piperidin-4-yl)-NH |
| 84 | CH₂ | HN-(9-azabicyclo[3.3.1]nonan-3-yl) |
| 85 | S | HN-(9-azabicyclo[3.3.1]nonan-3-yl) |
| 86 | S | HN-(9-azabicyclo[3.3.1]nonan-3-yl) |
| 87 | S | HN-CH₂-(9-azabicyclo[3.3.1]nonan-3-yl) |
| 88 | S | HN-(pyridin-2-yl)-NH-CH₂CH₂-NMe₂ (3-amino) |
| 89 | S | HN-(5-amino-pyridin-2-yl)-NH-CH₂CH₂-NMe₂ |

-continued

| Entry | X | NR₂R₃ |
|---|---|---|
| 90 | S | HN-(2-piperidin-1-yl-pyridin-3-yl) |
| 91 | S | HN-(6-piperidin-1-yl-pyridin-3-yl) |
| 92 | CH₂ | N-(piperidin-4-yl)-N(Me)-CO₂Et |
| 93 | CH₂ | N-(piperidin-4-yl)-N(Me)-CH₂CH₂OMe |
| 94 | CH₂ | N-(piperidin-4-yl)-N(Me)-C(O)-CH₂OMe |
| 95 | CH₂ | 4-(piperidin-1-yl)-piperidin-1-yl |
| 96 | CH₂ | 4-(methoxymethyl)-piperidin-1-yl |
| 97 | CH₂ | 4-(CH₂-N(Me)-CH₂CH₂-NMe₂)-piperidin-1-yl |
| 98 | CH₂ | 4-((4-methylpiperazin-1-yl)methyl)-piperidin-1-yl |
| 99 | CH₂ | 4-(N-Me-NH)-piperidin-1-yl 3HCl |

-continued
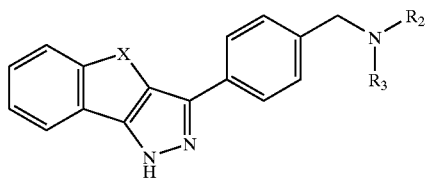
| Entry | X | NR₂R₃ |
|---|---|---|
| 100 | CH₂ | 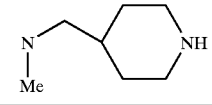 |
| 101 | CH₂ | 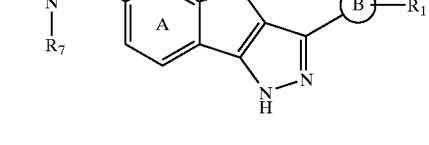 |
| 102 | CH₂ | 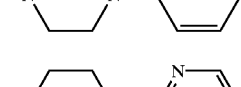 |
| 103 | CH₂ | 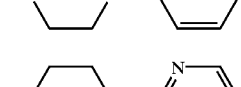 |
| 104 | CH₂ | 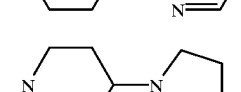 |
| 105 | S | 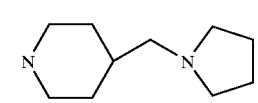 |
| 106 | S | 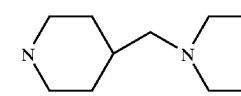 |
| 107 | S | 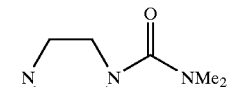 |
| 108 | S | 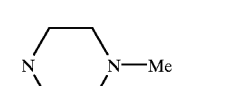 |
| 109 | S | 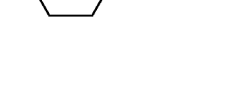 |
| 110 | S | |
-continued
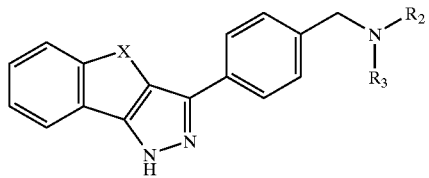
| Entry | X | NR₂R₃ |
|---|---|---|
| 111 | S | |
tautomers thereof and the pharmaceutically acceptable salts thereof.
41. A compound of the following structural formula wherein B, R₆ and R₇ are selected from:
| Entry | B with R₁ | —NR₆R₇ |
|---|---|---|
| 1 | Ph | |
| 2 | Ph | |
| 3 | Ph | |
| 4 | Ph | |
| 5 | Ph | |
| 6 | Ph | |
| 7 | Ph | |
| 8 | 4-MeO—Ph | |

-continued

| Entry | B with R₁ | —NR₆R₇ |
|---|---|---|
| 9 | 4-MeO—Ph | HN-pyridin-4-yl |
| 10 | 3-F—Ph | 4-methylpiperazin-1-yl |
| 11 | 3-F—Ph | 4-(dimethylamino)piperidin-1-yl |
| 12 | 3-F—Ph | HN-pyridin-4-yl |
| 13 | Et | 4-methylpiperazin-1-yl |
| 14 | Et | HN-pyridin-4-yl |
| 15 | cyc-Pr | 4-methylpiperazin-1-yl (2HCl) |
| 16 | cyc-Pr | 4-(dimethylamino)piperidin-1-yl (2HCl) |
| 17 | cyc-Pr | HN-pyridin-4-yl | tautomers thereof and the pharmaceutically acceptable salts thereof.

42. A compound of the following formula wherein X, R₂ and R₃ are selected from:

| Entry | X | NR₂R₃ |
|---|---|---|
| 1 | CH₂ | HN-pyridin-4-yl |
| 2 | CH₂ | HN-imidazol-2-yl |
| 3 | CH₂ | NMe₂ |
| 4 | CH₂ | piperidin-1-yl |
| 5 | CH₂ | 4-methylpiperazin-1-yl |
| 6 | S | HN-pyridin-4-yl |
| 7 | S | NMe₂ |
| 8 | S | HN-CH₂CH₂-NMe₂ |
| 9 | S | 4-methylpiperazin-1-yl |
| 10 | S | HN-CH₂-piperidin-4-yl (NH) |
| 11 | S | piperidin-1-yl | tautomers thereof and the pharmaceutically acceptable salts thereof.

43. A compound of the following formula wherein R₆, R₇ and R₈ are selected from:

| Entry | R8 | NR6R7 |
|---|---|---|
| 1 | H |  |
| 2 | H | 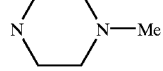 |
| 3 | H | 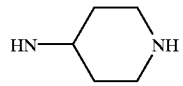 |
| 4 | H |  |
| 5 | H | 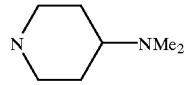 |
| 6 | H | 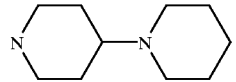 |
| 7 | H | 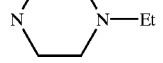 |
| 8 | H | 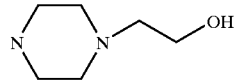 |
| 9 | H |  |
| 10 | H | 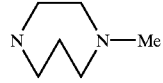 |
| 11 | F | 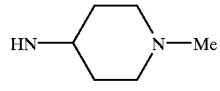 |
| 12 | F | 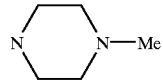 |
| 13 | F | 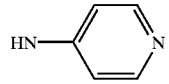 |

-continued

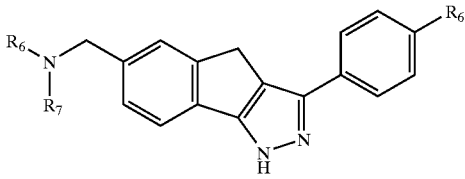

| Entry | R8 | NR6R7 |
|---|---|---|
| 14 | H | 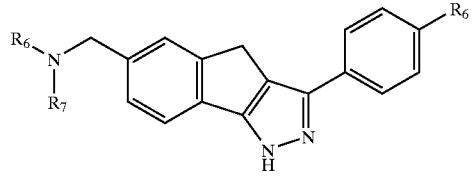 (2HCl) |
| 15 | H | 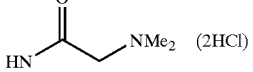 (: | tautomers thereof and the pharmaceutically acceptable salts thereof.

44. A compound represented by the following structural formula:

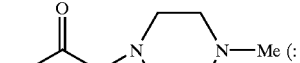

tautomers thereof and the pharmaceutically acceptable salts thereof.

45. A method of inhibiting protein kinase activity in a mammal in need thereof comprising the step of administering to said mammal a compound of formula (I):

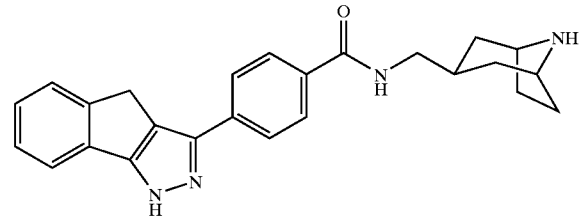

(I)

the racemic mixtures, racemic-diastereomeric mixtures, tautomers and optical isomers of said compounds and the pharmaceutically acceptable salts and the prodrugs thereof, wherein:

m is an integer from 1 to 10;

X represents a) an optionally substituted group of the formula —$(CH_2)_n$— in which n is 1, 2 or 3, b) carbonyl, c) oxygen, d) a group of the formula —C=$NOR_{10}$, in which $R_{10}$ is a $C_{1-4}$ alkyl group, e) a group of the formula $NR_{11}$, in which $R_{11}$ is —H, an optionally substituted $C_{1-4}$ alkyl group or an optionally substituted phenyl, or f) a group of formula $S(O)_p$ in which p is 0, 1 or 2;

B represents an alkyl, a cycloalkyl, an aryl, a pyridyl, a thienyl, a furyl or a pyrrolyl;

$R_1$ is —H; a halo; hydroxy; nitro; cyano; hydroxyamidino; aminomethyl; formamidomethyl; an optionally substituted alkenyloxy; an optionally substituted $C_{2-4}$ alkenyl; an optionally substituted $C_{2-4}$ alkynyl; or a group represented by the formula —Y—W; provided that when $R_1$ is —H, an unsubstituted $C_{1-6}$ alkyl, an unsubstituted $C_{1-6}$ alkoxy, a halogen, or trifluoromethyl, then ring A is substituted with at least one substituent that is not a halo, an optionally substituted $C_{1-6}$ alkyl or an optionally substituted $C_{1-6}$ alkoxy;

Y is absent or a $C_{1-6}$ alkyl, $C_{1-6}$ alkoxy, —O—, —S— or —C(O)—;

W is —H, hydroxy, optionally substituted phenyl, $C_{1-6}$ alkoxy, or —$NR_2R_3$;

provided that when B is phenyl and $R_1$ is —Y—W and W is —$NR_2R_3$, then $R_2$ and $R_3$ are each, independently, a) —H; b) a substituted $C_{1-6}$ alkyl group, provided that the substituent is not —$NR_6R_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with —$NR_9(CH_2)_{1-6}R_4$, —$NR_9(CH_2)_{1-6}CO_2R_4$, —$NR_9(CH_2)_{1-6}NR_4R_5$, or an optionally substituted heterocycloalkyl; or when B is phenyl and $R_1$ is —Y—W and W is —$NR_2R_3$, then $R_2$ and $R_3$, together with the nitrogen atom to which they are attached, can represent an optionally substituted heterocycloalkyl or an optionally substituted heteroaryl;

when B is not phenyl, then $R_2$ and $R_3$ are each, independently, —H, an optionally substituted $C_{1-6}$ alkyl group, —$NH(CH_2)_{1-6}NR_4R_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, then $R_2$ and $R_3$ together with the nitrogen atom to which they are attached represent an optionally substituted heterocycloalkyl or an optionally substituted heteroaryl;

$R_4$, $R_5$ and $R_9$ are for each occurrence, independently, —H or a $C_{1-6}$ alkyl; and ring A is optionally substituted with one or more substituents selected from the group consisting of a) a halo; b) a $C_{1-6}$ alkyl group optionally substituted with one or more substituents selected from the group consisting of hydroxy, halo, and —$NR_6R_7$; c) a $C_{1-6}$ alkoxy group optionally substituted with one or more substituents selected from the group consisting of hydroxy, halo, —$NR_6R_7$, an optionally substituted phenyl, and —$NR_{17}C(O)R_{19}$, provided that the substituents are not attached to the carbon which is attached to the oxygen of the alkoxy group; d) an optionally substituted phenoxy; e) hydroxy; f) a group of the formula —$C(O)R_{12}$ in which $R_{12}$ is a hydroxy, a $C_{1-6}$ alkoxy or —$NR_{13}R_{14}$; g) a group of the formula —$NR_{17}R_{18}$; h) a group of the formula —$NR_{17}C(O)R_{19}$; i) nitro; j) optionally substituted aralkyl; k) cyano; and l) a $C_{2-4}$ alkenyl group or a $C_{2-4}$ alkynyl group each of which is optionally substituted with one or more substituents selected from the group consisting of a $C_{1-6}$ alkyl group, a $C_{1-6}$ alkoxy group and a halo;

$R_6$ and $R_7$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_6$ and $R_7$ together with the nitrogen atom to which they are attached represent an optionally substituted heterocycloalkyl or an optionally substituted heteroaryl;

$R_{13}$ and $R_{14}$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_{13}$ and $R_{14}$ together with the nitrogen atom to which they are attached represent an optionally substituted heterocycloalkyl or an optionally substituted heteroaryl;

$R_{17}$ and $R_{18}$ are each, independently, selected from the group consisting of —H, a $C_{1-12}$ alkyl group, a $C_{3-12}$ cycloalkyl group, and phenyl; and $R_{19}$ is —H, an optionally substituted $C_{1-12}$ alkyl group, an optionally substituted $C_{3-12}$ cycloalkyl group, an optionally substituted phenyl or an optionally substituted aralkyl.

46. A method of claim 45, wherein $R_1$ is —H; a halo; hydroxy; nitro; cyano; hydroxyamidino; aminomethyl; formamidomethyl; alkenyloxy; a $C_{2-4}$ alkenyl group optionally substituted with a $C_{1-6}$ alkyl group, a $C_{1-6}$ alkoxy group or a halo; a $C_{2-4}$ alkynyl group optionally substituted with a $C_{1-6}$ alkyl group, a $C_{1-6}$ alkoxy group or a halo; or a group represented by the formula —Y—W, provided that when R is —H, an unsubstituted $C_{1-6}$ alkyl, an unsubstituted $C_{1-6}$ alkoxy or a halogen, ring A is substituted with at least one substituent that is not a halo, an optionally substituted $C_{1-6}$ alkyl or an optionally substituted $C_{1-6}$ alkoxy.

47. The method of claim 45, wherein said protein kinase is a tyrosine kinase.

48. The method of claim 47, wherein said tyrosine kinase is either a receptor tyrosine kinase or a non-receptor tyrosine kinase.

49. The method of claim 48, wherein said tyrosine kinase is selected from the group consisting of KDR, flt-1, TIE-2, Lck, Src, fyn and yes.

50. A method of affecting angiogenesis in a mammal in need thereof comprising the step of administering to said mammal a compound of formula (I):

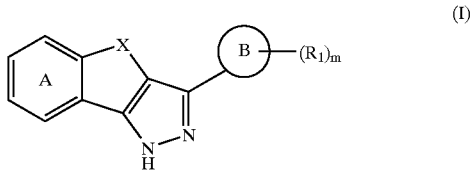

the racemic mixtures, racemic-diastereomeric mixtures, tautomers and optical isomers of said compounds and the pharmaceutically acceptable salts and the prodrugs thereof, wherein:

m is an integer from 1 to 10;

X represents a) an optionally substituted group of the formula —$(CH_2)_n$— in which n is 1, 2 or 3, b) carbonyl, c) oxygen, d) a group of the formula —C=$NOR_{10}$, in which $R_{10}$ is a $C_{1-4}$ alkyl group, e) a group of the formula $NR_{11}$, in which $R_{11}$ is —H, an optionally substituted $C_{1-4}$ alkyl group or an optionally substituted phenyl, or f) a group of formula $S(O)_p$ in which p is 0, 1 or 2;

B represents an alkyl, a cycloalkyl, an aryl, a pyridyl, a thienyl, a furyl or a pyrrolyl;

$R_1$ is —H; a halo; hydroxy; nitro; cyano; hydroxyamidino; aminomethyl; formamidomethyl; an optionally substituted alkenyloxy; an optionally substituted $C_{2-4}$ alkenyl; an optionally substituted $C_{2-4}$ alkynyl; or a group represented by the formula —Y—W; provided that when $R_1$ is —H, an unsubstituted $C_{1-6}$ alkyl, an unsubstituted $C_{1-6}$ alkoxy, a halogen, or trifluoromethyl, then ring A is substituted with at least one substituent that is not a halo, an optionally substituted $C_{1-6}$ alkyl or an optionally substituted $C_{1-6}$ alkoxy;

Y is absent or a $C_{1-6}$ alkyl, $C_{1-6}$ alkoxy, —O—, —S— or —C(O)—;

W is —H, hydroxy, optionally substituted phenyl, $C_{1-6}$ alkoxy, or —$NR_2R_3$;

provided that when B is phenyl and $R_1$ is —Y—W and W is —$NR_2R_3$, then $R_2$ and $R_3$ are each, independently, a) —H; b) a substituted $C_{1-6}$ alkyl group, provided that the substituent is not —$NR_6R_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with —$NR_9(CH_2)_{1-6}OR_4$, —$NR_9(CH_2)_{1-6}CO_2R_4$, —$NR_9(CH_2)_{1-6}NR_4R_5$, or an optionally substituted heterocycloalkyl; or when B is phenyl and $R_1$ is —Y—W and W is —$NR_2R_3$, then $R_2$ and $R_3$, together with the nitrogen atom to which they are attached, can represent an optionally substituted heterocycloalkyl or an optionally substituted heteroaryl;

when B is not phenyl, then $R_2$ and $R_3$ are each, independently, —H, an optionally substituted $C_{1-6}$ alkyl group, —$NH(CH_2)_{1-6}NR_4R_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, then $R_2$ and $R_3$ together with the nitrogen atom to which they are attached represent an optionally substituted heterocycloalkyl or an optionally substituted heteroaryl;

$R_4$, $R_5$ and $R_9$ are for each occurrence, independently, —H or a $C_{1-6}$ alkyl; and ring A is optionally substituted with one or more substituents selected from the group consisting of a) a halo; b) a $C_{1-6}$ alkyl group optionally substituted with one or more substituents selected from the group consisting of hydroxy, halo, and —$NR_6R_7$; c) a $C_{1-6}$ alkoxy group optionally substituted with one or more substituents selected from the group consisting of hydroxy, halo, —$NR_6R_7$, an optionally substituted phenyl, and —$NR_{17}C(O)R_{19}$, provided that the substituents are not attached to the carbon which is attached to the oxygen of the alkoxy group; d) an optionally substituted phenoxy; e) hydroxy; f) a group of the formula —$C(O)R_{12}$ in which $R_{12}$ is a hydroxy, a $C_{1-6}$ alkoxy or —$NR_{13}R_{14}$; g) a group of the formula —$NR_{17}R_{18}$; h) a group of the formula —$NR_{17}C(O)R_{19}$; i) nitro; j) optionally substituted aralkyl; k) cyano; and l) a $C_{2-4}$ alkenyl group or a $C_{2-4}$ alkynyl group each of which is optionally substituted with one or more substituents selected from the group consisting of a $C_{1-6}$ alkyl group, a $C_{1-6}$ alkoxy group and a halo;

$R_6$ and $R_7$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_6$ and $R_7$ together with the nitrogen atom to which they are attached represent an optionally substituted heterocycloalkyl or an optionally substituted heteroaryl;

$R_{13}$ and $R_{14}$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_{13}$ and $R_{14}$ together with the nitrogen atom to which they are attached represent an optionally substituted heterocycloalkyl or an optionally substituted heteroaryl;

$R_{17}$ and $R_{18}$ are each, independently, selected from the group consisting of —H, a $C_{1-12}$ alkyl group, a $C_{3-12}$ cycloalkyl group, and phenyl; and $R_{19}$ is —H, an optionally substituted $C_{1-12}$ alkyl group, an optionally substituted $C_{3-12}$ cycloalkyl group, an optionally substituted phenyl or an optionally substituted aralkyl.

51. The method of claim 50, wherein anti-angiogenic affect is effected.

52. A method of inhibiting the progression of a disease state in a mammal in need thereof wherein said disease is selected from the group consisting of cancer, arthritis, atherosclerosis, psoriasis, hemangioma, myocardial angiogenesis, coronary and cerebral collateral vascularization, ischemic limb angiogenesis, corneal disease, rubeosis, neovascular glaucoma, macular degeneration, retinopathy of prematurity, wound healing, ulcers, Helicobacter-caused diseases, fractures, endometriosis, diabetic retinopathy, cat scratch fever, and thyroid hyperplasia, burns, trauma, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, sepsis, adult respiratory distress syndrome, multiple-organ dysfunction syndrome, ascites and tumor-associated effusions and edema, comprising the step of administering a compound of formula (I):

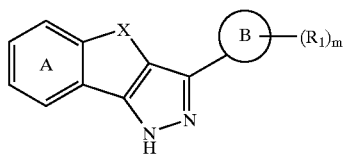 (I)

the racemic mixtures, racemic-diastereomeric mixtures, tautomers and optical isomers of said compounds and the pharmaceutically acceptable salts and the prodrugs thereof, wherein:

m is an integer from 1 to 10;

X represents a) an optionally substituted group of the formula —(CH$_2$)$_n$— in which n is 1, 2 or 3, b) carbonyl, c) oxygen, d) a group of the formula —C=NOR$_{10}$, in which R$_{10}$ is a C$_{1-4}$ alkyl group, e) a group of the formula NR$_{11}$, in which R$_{11}$ is —H, an optionally substituted C$_{1-4}$ alkyl group or an optionally substituted phenyl, or f) a group of formula S(O)$_p$ in which p is 0, 1 or 2;

B represents an alkyl, a cycloalkyl, an aryl, a pyridyl, a thienyl, a furyl or a pyrrolyl;

R$_1$ is —H; a halo; hydroxy; nitro; cyano hydroxyamidino; aminomethyl; formamidomethyl; an optionally substituted alkenyloxy; an optionally substituted C$_{2-4}$ alkenyl; an optionally substituted C$_{2-4}$ alkynyl; or a group represented by the formula —Y—W; provided that when R$_1$ is —H, an unsubstituted C$_{1-6}$ alkyl, an unsubstituted C$_{1-6}$ alkoxy, a halogen, or trifluoromethyl, then ring A is substituted with at least one substituent that is not a halo, an optionally substituted C$_{1-6}$ alkyl or an optionally substituted C$_{1-6}$ alkoxy;

Y is absent or a C$_{1-6}$ alkyl, C$_{1-6}$ alkoxy, —O—, —S— or —C(O)—;

W is —H, hydroxy, optionally substituted phenyl, C$_{1-6}$ alkoxy, or —NR$_2$R$_3$;

provided that when B is phenyl and R$_1$ is —Y—W and W is —NR$_2$R$_3$, then R$_2$ and R$_3$ are each, independently, a) —H; b) a substituted C$_{1-6}$ alkyl group, provided that the substituent is not —NR$_6$R$_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with —NR$_9$(CH$_2$)$_{1-6}$OR$_4$, —NR$_9$(CH$_2$)$_{1-6}$CO$_2$R$_4$, —NR$_9$(CH$_2$)$_{1-6}$NR$_4$R$_5$, or an optionally substituted heterocycloalkyl; or when B is phenyl and R$_1$ is —Y—W and W is —NR$_2$R$_3$, then R$_2$ and R$_3$, together with the nitrogen atom to which they are attached, can represent an optionally substituted heterocycloalkyl or an optionally substituted heteroaryl;

when B is not phenyl, then R$_2$ and R$_3$ are each, independently, —H, an optionally substituted C$_{1-6}$ alkyl group, —NH(CH$_2$)$_{1-6}$NR$_4$R$_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, then R$_2$ and R$_3$ together with the nitrogen atom to which they are attached represent an optionally substituted heterocycloalkyl or an optionally substituted heteroaryl;

R$_4$, R$_5$ and R$_9$ are for each occurrence, independently, —H or a C$_{1-6}$ alkyl; and ring A is optionally substituted with one or more substituents selected from the group consisting of a) a halo; b) a C$_{1-6}$ alkyl group optionally substituted with one or more substituents selected from the group consisting of hydroxy, halo, and —NR$_6$R$_7$; c) a C$_{1-6}$ alkoxy group optionally substituted with one or more substituents selected from the group consisting of hydroxy, halo, —NR$_6$R$_7$, an optionally substituted phenyl, and —NR$_{17}$C(O)R$_{19}$, provided that the substituents are not attached to the carbon which is attached to the oxygen of the alkoxy group; d) an optionally substituted phenoxy; e) hydroxy; f) a group of the formula —C(O)R$_{12}$ in which R$_{12}$ is a hydroxy, a C$_{1-6}$ alkoxy or —NR$_{13}$R$_{14}$; g) a group of the formula —NR$_{17}$R$_{18}$; h) a group of the formula —NR$_{17}$C(O)R$_{19}$; i) nitro; j) optionally substituted aralkyl; k) cyano; and l) a C$_{2-4}$ alkenyl group or a C$_{2-4}$ alkynyl group each of which is optionally substituted with one or more substituents selected from the group consisting of a C$_{1-6}$ alkyl group, a C$_{1-6}$ alkoxy group and a halo;

R$_6$ and R$_7$ are each, independently, —H, an optionally substituted C$_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or R$_6$ and R$_7$ together with the nitrogen atom to which they are attached represent an optionally substituted heterocycloalkyl or an optionally substituted heteroaryl;

R$_{13}$ and R$_{14}$ are each, independently, —H, an optionally substituted C$_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or R$_{13}$ and R$_{14}$ together with the nitrogen atom to which they are attached represent an optionally substituted heterocycloalkyl or an optionally substituted heteroaryl;

R$_{17}$ and R$_{18}$ are each, independently, selected from the group consisting of —H, a C$_{12}$ alkyl group, a C$_{3-12}$ cycloalkyl group, and phenyl; and R$_{19}$ is —H, an optionally substituted C$_{1-12}$ alkyl group, an optionally substituted C$_{3-12}$ cycloalkyl group, an optionally substituted phenyl or an optionally substituted aralkyl.

53. A method of inhibiting vascular hyperpermeability or the production of edema in a mammal in need thereof comprising the step of administering to said mammal a compound of formula (I):

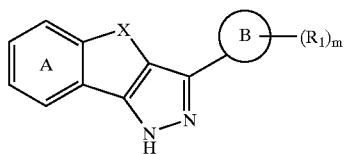

(I)

the racemic mixtures, racemic-diastereomeric mixtures, tautomers and optical isomers of said compounds and the pharmaceutically acceptable salts and the prodrugs thereof, wherein:

m is an integer from 1 to 10;

X represents a) an optionally substituted group of the formula $-(CH_2)_n-$ in which n is 1, 2 or 3, b) carbonyl, c) oxygen, d) a group of the formula $-C=NOR_{10}$, in which $R_{10}$ is a $C_{1-4}$ alkyl group, e) a group of the formula $NR_{11}$, in which $R_{11}$ is $-H$, an optionally substituted $C_{1-4}$ alkyl group or an optionally substituted phenyl, or f) a group of formula $S(O)_p$ in which p is 0, 1 or 2;

B represents an alkyl, a cycloalkyl, an aryl, a pyridyl, a thienyl, a furyl or a pyrrolyl;

$R_1$ is $-H$; a halo; hydroxy; nitro; cyano; hydroxyamidino; aminomethyl; formamidomethyl; an optionally substituted alkenyloxy; an optionally substituted $C_{2-4}$ alkenyl; an optionally substituted $C_{2-4}$ alkynyl; or a group represented by the formula $-Y-W$; provided that when $R_1$ is $-H$, an unsubstituted $C_{1-6}$ alkyl, an unsubstituted $C_{1-6}$ alkoxy, a halogen, or trifluoromethyl, then ring A is substituted with at least one substituent that is not a halo, an optionally substituted $C_{1-6}$ alkyl or an optionally substituted $C_{1-6}$ alkoxy;

Y is absent or a $C_{1-6}$ alkyl, $C_{1-6}$ alkoxy, $-O-$, $-S-$ or $-C(O)-$;

W is $-H$, hydroxy, optionally substituted phenyl, $C_{1-6}$ alkoxy, or $-NR_2R_3$;

provided that when B is phenyl and $R_1$ is $-Y-W$ and W is $-NR_2R_3$, then $R_2$ and $R_3$ are each, independently, a) $-H$; b) a substituted $C_{1-6}$ alkyl group, provided that the substituent is not $-NR_6R_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with $-NR_9(CH_2)_{1-6}OR_4$, $-NR_9(CH_2)_{1-6}CO_2R_4$, $-NR_9(CH_2)_{1-6}NR_4R_5$, or an optionally substituted heterocycloalkyl; or when B is phenyl and $R_1$ is $-Y-W$ and W is $-NR_2R_3$, then $R_2$ and $R_3$, together with the nitrogen atom to which they are attached, can represent an optionally substituted heterocycloalkyl or an optionally substituted heteroaryl;

when B is not phenyl, then $R_2$ and $R_3$ are each, independently, $-H$, an optionally substituted $C_{1-6}$ alkyl group, $-NH(CH_2)_{1-6}NR_4R_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, then $R_2$ and $R_3$ together with the nitrogen atom to which they are attached represent an optionally substituted heterocycloalkyl or an optionally substituted heteroaryl;

$R_4$, $R_5$ and $R_9$ are for each occurrence, independently, $-H$ or a $C_{1-6}$ alkyl; and ring A is optionally substituted with one or more substituents selected from the group consisting of a) a halo; b) a $C_{1-6}$ alkyl group optionally substituted with one or more substituents selected from the group consisting of hydroxy, halo, and $-NR_6R_7$; c) a $C_{1-6}$ alkoxy group optionally substituted with one or more substituents selected from the group consisting of hydroxy, halo, $-NR_6R_7$, an optionally substituted phenyl, and $-NR_{17}C(O)R_{19}$, provided that the substituents are not attached to the carbon which is attached to the oxygen of the alkoxy group; d) an optionally substituted phenoxy; e) hydroxy; f) a group of the formula $-C(O)R_{12}$ in which $R_{12}$ is a hydroxy, a $C_{1-6}$ alkoxy or $-NR_{13}R_{14}$; g) a group of the formula $-NR_{17}R_{18}$; h) a group of the formula $-NR_{17}C(O)R_{19}$; i) nitro; j) optionally substituted aralkyl; k) cyano; and l) a $C_{2-4}$ alkenyl: group or a $C_{2-4}$ alkynyl group each of which is optionally substituted with one or more substituents selected from the group consisting of a $C_{1-6}$ alkyl group, a $C_{1-6}$ alkoxy group and a halo;

$R_6$ and $R_7$ are each, independently, $-H$, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_6$ and $R_7$ together with the nitrogen atom to which they are attached represent an optionally substituted heterocycloalkyl or an optionally substituted heteroaryl;

$R_{13}$ and $R_{14}$ are each, independently, $-H$, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_{13}$ and $R_{14}$ together with the nitrogen atom to which they are attached represent an optionally substituted heterocycloalkyl or an optionally substituted heteroaryl;

$R_{17}$ and $R_{18}$ are each, independently, selected from the group consisting of $-H$, a $C_{1-12}$ alkyl group, a $C_{3-12}$ cycloalkyl group, and phenyl; and $R_{19}$ is $-H$, an optionally substituted $C_{1-12}$ alkyl group, an optionally substituted $C_{3-12}$ cycloalkyl group, an optionally substituted phenyl or an optionally substituted aralkyl.

54. A method of inhibiting fertility or inducing abortifacient effects in a mammal in need thereof, comprising the step of administering to said mammal a compound of formula (I):

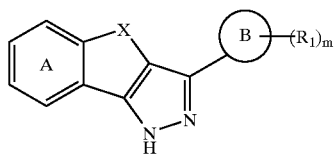
(I)

the racemic mixtures, racemic-diastereomeric mixtures, tautomers and optical isomers of said compounds and the pharmaceutically acceptable salts arid the prodrugs thereof, wherein:

m is an integer from 1 to 10;

X represents a) an optionally substituted group of the formula —$(CH_2)_n$— in which n is 1, 2 or 3, b) carbonyl, c) oxygen d) a group of the formula —C=$NOR_{10}$, in which $R_{10}$ is a $C_{1-4}$ alkyl group, e) a group of the formula $NR_{11}$, in which $R_{11}$ is —H, an optionally substituted $C_{1-4}$ alkyl group or an optionally substituted phenyl, or f) a group of formula $S(O)_p$ in which p is 0, 1 or 2;

B represents an alkyl, a cycloalkyl, an aryl, a pyridyl, a thienyl, a furyl or a pyrrolyl;

$R_1$ is —H; a halo; hydroxy; nitro; cyano; hydroxyamidino; aminomethyl; formamidomethyl; an optionally substituted alkenyloxy; an optionally substituted $C_{2-4}$ alkenyl; an optionally substituted $C_{2-4}$ alkynyl; or a group represented by the formula —Y—W, provided that when $R_1$ is —H, an unsubstituted $C_{1-6}$ alkyl, an unsubstituted $C_{1-6}$ alkoxy, a halogen, or trifluoromethyl, then ring A is substituted with at least one substituent that is not a halo, an optionally substituted $C_{1-6}$ alkyl or an optionally substituted $C_{1-6}$ alkoxy;

Y is absent or a $C_{1-6}$ alkyl, $C_{1-6}$ alkoxy, —O—, —S— or —C(O)—;

W is —H, hydroxy, optionally substituted phenyl, $C_{1-6}$ alkoxy, or —$NR_2R_3$;

provided that when B is phenyl and $R_1$ is —Y—W and W is —$NR_2R_3$, then $R_2$ and $R_3$ are each, independently, a) —H; b) a substituted $C_{1-6}$ alkyl group, provided that the substituent is not —$NR_6R_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with —$NR_9(CH_2)_{1-6}OR_4$, —$NR_9(CH_2)_{1-6}CO_2R_4$, —$NR_9(CH_2)_{1-6}NR_4R_5$, or an optionally substituted heterocycloalkyl; or when B is phenyl, then $R_2$ and $R_3$, together with the nitrogen atom to which they are attached, can represent an optionally substituted heterocycloalkyl or an optionally substituted heteroaryl;

when B is not phenyl, then $R_2$ and $R_3$ are each, independently, —H, an optionally substituted $C_{1-6}$ alkyl group, —NH$(CH_2)_{1-6}NR_4R_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, then $R_2$ and $R_3$ together with the nitrogen atom to which they are attached represent an optionally substituted heterocycloalkyl or an optionally substituted heteroaryl;

$R_4$, $R_5$ and $R_9$ are for each occurrence, independently, —H or a $C_{1-6}$ alkyl; and ring A is optionally substituted with one or more substituents selected from the group consisting of a) a halo; b) a $C_{1-6}$ alkyl group optionally substituted with one or more substituents selected from the group consisting of hydroxy, halo, and —$NR_6R_7$; c) a $C_{1-6}$ alkoxy group optionally substituted with one or more substituents selected from the group consisting of hydroxy, halo, —$NR_6R_7$, an optionally substituted phenyl, and —$NR_{17}C(O)R_{19}$, provided that the substituents are not attached to the carbon which is attached to the oxygen of the alkoxy group; d) an optionally substituted phenoxy; e) hydroxy; f) a group of the formula —$C(O)R_{12}$ in which $R_{12}$ is a hydroxy, a $C_{1-6}$ alkoxy or —$NR_{13}R_{14}$; g) a group of the formula —$NR_{17}R_{18}$; h) a group of the formula —$NR_{17}C(O)R_{19}$; i) nitro; j) optionally substituted aralkyl; k) cyano; and l) a $C_{2-4}$ alkenyl group or a $C_{2-4}$ alkynyl group each of which is optionally substituted with one or more substituents selected from the group consisting of a $C_{1-6}$ alkyl group, a $C_{1-6}$ alkoxy group and a halo;

$R_6$ and $R_7$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_6$ and $R_7$ together with the nitrogen atom to which they are attached represent an optionally substituted heterocycloalkyl or an optionally substituted heteroaryl;

$R_{13}$ and $R_{14}$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_{13}$ and $R_{14}$ together with the nitrogen atom to which they are attached represent an optionally substituted heterocycloalkyl or an optionally substituted heteroaryl;

$R_{17}$ and $R_{18}$ are each, independently, selected from the group consisting of —H, a $C_{1-12}$ alkyl group, a $C_{3-12}$ cycloalkyl group, and phenyl; and $R_{19}$ is —H, an optionally substituted $C_{1-12}$ alkyl group, an optionally substituted $C_{3-12}$ cycloalkyl group, an optionally substituted phenyl or an optionally substituted aralkyl.

55. A method of inhibiting the progression of a disease state in a mammal in need thereof wherein said disease is selected from the group consisting of corneal disease, macular degeneration, endometriosis, thyroid hyperplasia, burns, trauma, chronic lung disease, stroke, polyps, cysts, synovitis, chronic and allergic inflammation, ovarian hyperstimulation syndrome, keloid, fibrosis, cirrhosis, carpal tunnel syndrome, sepsis, adult respiratory distress syndrome, and multiple-organ dysfunction syndrome, comprising the step of administering a compound of formula (I):

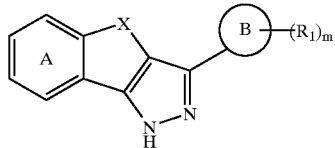
(I)

the racemic mixtures, racemic-diastereomeric mixtures, tautomers and optical isomers of said compounds and the pharmaceutically acceptable salts and the prodrugs thereof, wherein:

m is an integer from 1 to 10;

X represents a) an optionally substituted group of the formula —$(CH_2)_n$— in which n is 1, 2 or 3, b) carbonyl, c) oxygen, d) a group of the formula —C=$NOR_{10}$, in which $R_{10}$ is a $C_{1-4}$ alkyl group, e) a group of the formula $NR_{11}$, in which $R_{11}$ is —H, an optionally substituted $C_{1-4}$ alkyl group or an optionally substituted phenyl, or f) a. group of formula $S(O)_p$ in which p is 0, 1 or 2;

B represents an alkyl, a cycloalkyl, an aryl, a pyridyl, a thienyl, a furyl or a pyrrolyl;

$R_1$ is —H; a halo; hydroxy; nitro; cyano; hydroxyamidino; aminomethyl; formamidomethyl; an optionally substituted alkenyloxy; an optionally substituted $C_{2-4}$ alkenyl; an optionally substituted $C_{2-4}$ alkynyl; or a group represented by the formula —Y—W;

Y is absent or a $C_{1-6}$ alkyl, $C_{1-6}$ alkoxy, —O—, —S— or —C(O)—;

W is —H, hydroxy, optionally substituted phenyl, $C_{1-6}$ alkoxy, or —$NR_2R_3$;

provided that when B is phenyl and $R_1$ is —Y—W and W is —$NR_2R_3$, then $R_2$ and $R_3$ are each, independently, a) —H; b) a substituted $C_{1-6}$ alkyl group, provided that the substituent is not —$NR_6R_7$; c) an optionally substituted cycloalkyl; d) an optionally substituted heterocycloalkyl; e) an optionally substituted cycloalkylalkyl; f) an optionally substituted heterocycloalkylalkyl; g) a substituted heteroaryl or a substituted heteroaralkyl, provided that the heteroaryl or heteroaralkyl are substituted with —$NR_9(CH_2)_{1-6}OR_4$, —$NR_9(CH_2)_{1-6}CO_2R_4$, —$NR_9(CH_2)_{1-6}NR_4R_5$, or an optionally substituted heterocycloalkyl; or when B is phenyl and $R_1$ is —Y—W and W is —$NR_2R_3$, then $R_2$ and $R_3$, together with the nitrogen atom to which they are attached, can represent an optionally substituted heterocycloalkyl or an optionally substituted heteroaryl;

when B is not phenyl, then $R_2$ and $R_3$ are each, independently, —H, an optionally substituted $C_{1-6}$ alkyl group, —$NH(CH_2)_{1-6}NR_4R_5$, an optionally substituted cycloalkyl, an optionally substituted heterocycloalkyl, an optionally substituted aryl, an optionally substituted heteroaryl, an optionally substituted cycloalkylalkyl, an optionally substituted heterocycloalkylalkyl, an optionally substituted aralkyl, or an optionally substituted heteroaralkyl; or when B is not phenyl, then $R_2$ and $R_3$ together with the nitrogen atom to which they are attached represent an optionally substituted heterocycloalkyl or an optionally substituted heteroaryl;

$R_4$, $R_5$ and $R_9$ are for each occurrence, independently, —H or a $C_{1-6}$ alkyl; and ring A is optionally substituted with one or more substituents selected from the group consisting of a) a halo; b) a $C_{1-6}$ alkyl group optionally substituted with one or more substituents selected from the group consisting of hydroxy, halo, and —$NR_6R_7$; c) a $C_{1-6}$ alkoxy group optionally substituted with one or more substituents selected from the group consisting of hydroxy, halo, —$NR_6R_7$, an optionally substituted phenyl, and —$NR_{17}C(O)R_{19}$, provided that the substituents are not attached to the carbon which is attached to the oxygen of the alkoxy group; d) an optionally substituted phenoxy; e) hydroxy; f) a group of the formula $C(O)R_{12}$ in which $R_{12}$ is a hydroxy, a $C_{1-6}$ alkoxy or —$NR_{13}R_{14}$; g) a group of the formula —$NR_{17}R_{18}$; h) a group of the formula —$NR_{17}C(O)R_{19}$; i) nitro; j) optionally substituted aralkyl; k) cyano; and l) a $C_{2-4}$ alkenyl group or a $C_{2-4}$ alkynyl group each of which is optionally substituted with one or more substituents selected from the group consisting of a $C_{1-6}$ alkyl group, a $C_{1-6}$ alkoxy group and a halo;

$R_6$ and $R_7$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_6$ and $R_7$ together with the nitrogen atom to which they are attached represent an optionally substituted heterocycloalkyl or an optionally substituted heteroaryl;

$R_{13}$ and $R_{14}$ are each, independently, —H, an optionally substituted $C_{1-6}$ alkyl group, an optionally substituted cycloalkyl, an optionally substituted aryl, an optionally substituted heteroaryl, an optionally substituted heterocycloalkyl, an optionally substituted cycloalkylalkyl, an optionally substituted aralkyl, an optionally substituted heteroaralkyl, or an optionally substituted heterocycloalkylalkyl; or $R_{13}$ and $R_{14}$ together with the nitrogen atom to which they are attached represent an optionally substituted heterocycloalkyl or an optionally substituted heteroaryl;

$R_{17}$ and $R_{18}$ are each, independently, selected from the group consisting of —H, a $C_{1-12}$ alkyl group, a $C_{3-12}$ cycloalkyl group, and phenyl; and $R_{19}$ is —H, an optionally substituted $C_{1-12}$ alkyl group, an optionally substituted $C_{3-12}$ cycloalkyl group, an optionally substituted phenyl or an optionally substituted aralkyl.

* * * * *